(12) United States Patent
Bissantz et al.

(10) Patent No.: US 7,781,436 B2
(45) Date of Patent: Aug. 24, 2010

(54) INDOL-3-Y-CARBONYL-PIPERIDIN AND PIPERAZIN-DERIVATIVES

(75) Inventors: Caterina Bissantz, Village Neuf (FR); Christophe Grundschober, Rodersdorf (CH); Hasane Ratni, Habsheim (FR); Mark Rogers-Evans, Binningen (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 27 days.

(21) Appl. No.: 11/492,312

(22) Filed: Jul. 25, 2006

(65) Prior Publication Data
US 2007/0027163 A1 Feb. 1, 2007

(30) Foreign Application Priority Data

| Jul. 29, 2005 | (EP) | ................. 05107044 |
| Nov. 22, 2005 | (EP) | ................. 05111072 |

(51) Int. Cl.

| A61K 31/4985 | (2006.01) |
| A61K 31/454 | (2006.01) |
| A61K 31/497 | (2006.01) |
| A61K 31/506 | (2006.01) |
| C07D 401/06 | (2006.01) |
| C07D 401/14 | (2006.01) |
| C07D 405/14 | (2006.01) |
| C07D 487/04 | (2006.01) |
| C07D 209/42 | (2006.01) |
| C07D 209/22 | (2006.01) |

(52) U.S. Cl. ............ 514/249; 514/316; 514/318; 514/323; 514/339; 514/254.09; 514/344; 514/364; 514/405; 514/357; 514/362; 514/369; 514/373; 514/333; 546/191; 546/194; 546/198; 546/201; 546/278.1

(58) Field of Classification Search ............ None
See application file for complete search history.

(56) References Cited

U.S. PATENT DOCUMENTS

| 5,434,169 A * | 7/1995 | Jegham et al. ............ 514/322 |
| 5,567,711 A | 10/1996 | Sheppard et al. |
| 2005/0154024 A1 | 7/2005 | Bryans et al. |

FOREIGN PATENT DOCUMENTS

| DE | 2557342 | 6/1997 |
| EP | 0496692 | 7/1992 |
| EP | 059027 | 4/1994 |
| EP | 1243268 | 9/2002 |
| EP | 1452525 | 9/2004 |
| EP | 1553084 A1 | 7/2005 |
| ES | 2027898 | 6/1992 |
| GB | 1566307 | 12/1975 |
| JP | 03/0161470 | 7/1991 |
| WO | WO 95/25443 A1 | 9/1995 |
| WO | WO 98/06715 | 2/1998 |
| WO | 98/28292 * | 7/1998 |
| WO | WO 01/43746 | 6/2001 |
| WO | WO 02/085301 | 10/2002 |
| WO | WO 03/037862 | 5/2003 |
| WO | WO 2004/048330 | 6/2004 |
| WO | WO 2004/089470 | 10/2004 |
| WO | WO 2005/068466 A1 | 7/2005 |

OTHER PUBLICATIONS

Breteche et al., Journal of Enzyme Inhibition & Medicinal Chemistry (2002) vol. 17(6) pp. 415-424.
Germain et al., Journal of Heterocyclic Chemistry (1976), vol. 13(6) pp. 1209-1218 (English Summary provided at end of document).
Hirose et al., New Synthetic Method for 2-phenylindole Derivatives from 1-phenacylpyridinium Bromide (1961), vol. 81, pp. 1353-1356 (English abstract).
Wormser et al., Journal of Pharmaceutical Sciences (1961) vol. 50 pp. 976-977.
Golubev et al., (1981), Synthesis and Pharmacological Properties of Some 1-(2-Quinoly1)-4-(Indo1-3-alkyl)Piperazines vol. 15(2) pp. 88-90.
Ebner et al., Eur. J. Neurosci. vol. 15(2) pp. 384-388 (2002).
Liebsch et al., Regul. Pept. vol. 59(2) pp. 229-239 (1995).
Michelini et al., Ann. Ny Acad. Sci. vol. 897 pp. 198-211 (1999).
Van Kerckhoven et al., Eur. J. Pharmacol. vol. 449, pp. 135- 141 (2002).
Abstract corresponding to B10 (JP 03/161470).

* cited by examiner

Primary Examiner—Emily Bernhardt
(74) Attorney, Agent, or Firm—George W. Johnston; Patricia S. Rocha-Tramaloni; Kimberly J. Prior

(57) ABSTRACT

The present invention relates to indol-3-yl-carbonyl-piperidin and piperazin derivatives which act as V1a receptor antagonists and which are represented by Formula I:

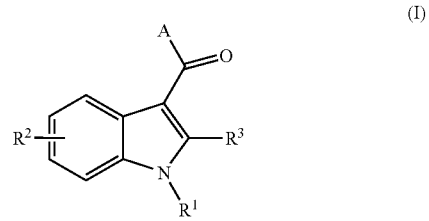

(I)

wherein the residues $R^1$ to $R^3$ are as defined herein. The invention also relates to pharmaceutical compositions containing such compounds, and methods for preparation of the compounds and compositions. The invention further relates to methods for treating dysmenorrhea, hypertension, chronic heart failure, inappropriate secretion of vasopressin, liver cirrhosis, nephrotic syndrome, obsessive compulsive disorder, anxiety and depressive disorders.

8 Claims, No Drawings

INDOL-3-Y-CARBONYL-PIPERIDIN AND PIPERAZIN-DERIVATIVES

PRIORITY TO RELATED APPLICATIONS

This application claims the benefit of European Application No. 05107044.9, filed Jul. 29, 2005, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." *Eur J Neurosci* 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxiety behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." *Neuropsychopharmacology*). The downregulation of the V1a receptor using antisense oligonucleotide injection in the septum also causes a reduction in anxiety behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." *Regul Pept* 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." *Ann N Y Acad Sci* 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." *Eur J Pharmacol* 449(1-2): 135-41).

Thus, vasopressin receptor antagonists are useful as therapeutics in the conditions of dysmenorrhea, hypertension, chronic heart failure, inappropriate secretion of vasopressin, liver cirrhosis, nephrotic syndrome, obsessive compulsive disorder, anxiety and depressive disorders.

SUMMARY OF THE INVENTION

The present invention provides compounds of formula (I)

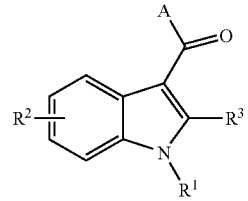

wherein
R$^1$ is H,
  C$_{1-6}$-alkyl substituted by CN, C$_{1-6}$-alkoxy, OH, halo, or NR$^i$R$^{ii}$, C$_{2-6}$-alkyl,
  aryl, 5 or 6 membered heteroaryl or sulfonylaryl each of which is optionally substituted by one or more B,
  —(CH$_2$)$_m$—R$^a$ wherein R$^a$ is:
    CN,
    OR$^i$,
    NR$^i$R$^{ii}$, or
    C$_{3-6}$-cycloalkyl, 4 to 7 membered-heterocycloalkyl, aryl, or 5 or 6 membered heteroaryl each of which is optionally substituted by one or more B,
  or —(CH$_2$)$_n$—(CO)—R$^b$ or —(CH$_2$)$_n$—(SO$_2$)—R$^b$, wherein R$^b$ is:
    C$_{1-6}$-alkyl,
    C$_{1-6}$-alkoxy,
    C$_{3-6}$-cycloalkyl,
    —(CH$_2$)$_m$—NR$^{iii}$R$^{iv}$,
    NR$^i$R$^{ii}$, or
    C$_{3-6}$-cycloalkyl, 4 to 7 membered-heterocycloalkyl, aryl, or 5 or 6 membered heteroaryl each of which is optionally substituted by one or more B,
  or R$^1$ and R$^3$ together with the indole ring to which they are attached form a 5 or 6 membered heterocycloalkyl which is optionally substituted by =O, C(O)O—C$_{1-6}$-alkyl or C$_{1-6}$-alkyl;
there is one or more R$^2$, wherein each R$^2$ is the same or different,
R$^2$ is one or more H, OH, halo, CN, nitro, C$_{1-6}$-alkoxy, —O—CH$_2$—C$_{2-6}$-alkenyl, benzyloxy, C$_{1-6}$-haloalkoxy, or C$_{1-6}$-alkyl optionally substituted by —NR$^{iii}$R$^{iv}$ or halo,
  or two R$^2$ together with the indole ring to which they are attached form an oxo or dioxo bridge;
R$^3$ is H,
  F,
  —(CO)—R$^c$, wherein R$^c$ is:
    C$_{1-6}$-alkyl,
    —(CH$_2$)$_n$—NR$^i$R$^{ii}$,
    —(CH$_2$)$_n$—NR$^{iii}$R$^{iv}$, or
    5 or 6 membered heterocycloalkyl optionally substituted by C$_{1-6}$-alkyl,
  or C$_{1-6}$-alkyl which is optionally substituted by
    halo,
    NR$^i$R$^{ii}$,
    NR$^{iii}$R$^{iv}$,
    —O(CO)—C$_{1-6}$-alkyl, or —NH(CO)R$^d$, wherein R$^d$ is C$_{1-6}$-alkyl optionally substituted by halo or nitro, or R$^d$ is aryl or a 5 or 6 membered heteroaryl, each of which is optionally substituted by halo, nitro, C$_{1-6}$-alkyl or C$_{1-6}$-haloalkyl;

A is selected from the group consisting of (a), (a'), (b), (c) and (d):

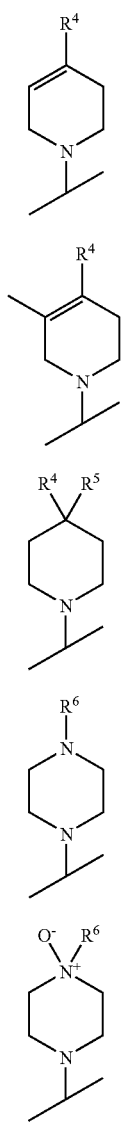

wherein

R$^4$ is —NH(CO)R$^e$, wherein R$^e$ is
- C$_{1-6}$-alkoxy or aryl each of which is optionally substituted by halo,
- C$_{1-6}$-alkoxy, or
- CN,
- or aryl, 5 or 6 membered heteroaryl, benzyl, aryloxy or a 9 or 10-membered bicyclic heteroaryl ring, each of which is optionally substituted by CN, halo, C$_{1-6}$-alkyl, C$_{1-6}$-alkoxy, C$_{1-6}$-haloalkyl, nitro, hydroxyl, NR$^i$R$^{ii}$, NR$^{iii}$R$^{iv}$, C$_{1-6}$-alkoxy-C$_{1-6}$-alkylene, S(O)$_2$—C$_{1-6}$-alkyl, or C$_{1-6}$-haloalkoxy, or by an oxo or dioxo bridge;

R$^5$ is H, OH, CN, COOR$^{iii}$ or CONR$^{iii}$R$^{iv}$;

R$^6$ is C$_{2-6}$-alkyl,
- —C(O)—R$^f$ wherein R$^f$ is an aryl group substituted by halo, C$_{1-6}$-alkoxy, or CN, aryl, 5 or 6 membered heteroaryl, or a 9 or 10-membered bicyclic heteroaryl ring each of which is optionally substituted by halo, C$_{1-6}$-alkyl, C$_{1-6}$-alkoxy, C$_{1-6}$-haloalkyl, CN, nitro, NR$^i$R$^{ii}$, NR$^{iii}$R$^{iv}$, C$_{1-6}$-alkoxy-C$_{1-6}$-alkylene, COOH, S(O)$_2$—C$_{1-6}$-alkyl, hydroxyl, or C$_{1-6}$-haloalkoxy, or by an oxo or dioxo bridge,
- or benzyl substituted by halo, C$_{1-6}$-alkyl, or C$_{1-6}$-haloalkyl or by an oxo- or dioxo bridge;

B is halo,
CN,
NR$^i$R$^{ii}$,
C$_{1-6}$-alkyl optionally substituted by CN, halo or C$_{1-6}$-alkoxy,
C$_{1-6}$-haloalkyl,
C$_{1-6}$-alkoxy,
C$_{1-6}$-haloalkoxy,
C$_{3-6}$-cycloalkyl,
—C(O)O—C$_{1-6}$-alkyl,
—C(O)NR$^i$R$^{ii}$,
—C(O)—C$_{1-6}$-alkyl,
—S(O)$_2$—C$_{1-6}$-alkyl,
—S(O)$_2$—NR$^i$R$^{ii}$, or
(CR$^{iii}$R$^{iv}$)$_n$-phenyl or (CR$^{iii}$R$^{iv}$)$_n$-5 or 6 membered heteroaryl wherein the phenyl or 5 or 6 membered heteroaryl moiety is optionally substituted by one or more substituent(s) selected from the group consisting of:
halo, CN, NR$^i$R$^{ii}$, C$_{1-6}$-alkyl optionally substituted by CN or C$_{1-6}$-alkoxy, C$_{1-6}$-alkoxy, C$_{1-6}$-haloalkoxy, C$_{3-6}$-cycloalkyl, —C(O)O—C$_{1-6}$-alkyl, —C(O)—NR$^i$R$^{ii}$, —C(O)—C$_{1-6}$-alkyl, —S(O)$_2$—C$_{1-6}$-alkyl, and —S(O)$_2$—NR$^i$R$^{ii}$;

R$^i$ and R$^{ii}$ are each independently H, C$_{1-6}$-alkyl, C$_{1-6}$-alkyl-NR$^{iii}$R$^{iv}$, —(CO)O—C$_{1-6}$-alkyl, —C(O)—NR$^{iii}$R$^{iv}$, —C(O)—C$_{1-6}$-alkyl, —S(O)$_2$—C$_{1-6}$-alkyl or —S(O)$_2$—NR$^{iii}$R$^{iv}$;

R$^{iii}$ and R$^{iv}$ are each independently H or C$_{1-6}$-alkyl;

m is 1 to 6; and n is 0 to 4;

and pharmaceutically acceptable salts thereof.

The compounds of formula (I) can contain asymmetric carbon atoms. Accordingly, the present invention includes all stereoisomeric forms of the compounds of formula I, including each of the individual enantiomers and mixtures thereof.

Compounds of formula (I) have good activity on the V1a receptor. Therefore, the invention provides pharmaceutical compositions comprising a therapeutically effective amount of a compound of formula (I) or a pharmaceutically acceptable salt thereof. The invention further provides a method for treating dysmenorrhea, hypertension, chronic heart failure, inappropriate secretion of vasopressin, liver cirrhosis, nephrotic syndrome, obsessive compulsive disorder, anxiety and depressive disorders by administering a compound of formula (I) or a pharmaceutically acceptable salt thereof.

The preferred indications with regard to the present invention are the treatment of anxiety and depressive disorders.

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "aryl" means a monovalent cyclic aromatic hydrocarbon moiety consisting of a mono-, bi- or tricyclic aromatic ring. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, and diphenylisopropylidenyl, as well as those specifically illustrated by the examples herein below. Substituents for aryl include, but are not limited to, halogen, $C_{1-6}$-alkyl, and $C_{1-6}$-alkoxy. Preferred aryl are phenyl and naphthyl, and still more preferably phenyl. The aryl moieties of the invention further can be ortho substituted by two substituents which together with the carbons of the aryl moiety form a fused, saturated or partially saturated, 5- to 6-membered ring containing one or two heteroatoms selected from O and N. Preferably the additional ring is a 5- to 6-membered ring containing two oxygen atoms. Examples of such substituted aryl moieties include, but are not limited to, benzodioxanyl, dihydro-benzofuranyl, benzodioxolyl, benzopyranyl, benzoxazinyl, benzoxazinonyl, benzopiperidinyl, benzopiperazinyl, benzopyrrolidinyl, benzomorpholinyl, methylenedioxyphenyl, ethylenedioxyphenyl, as well as those specifically illustrated by the examples herein below.

The term "aryloxy" denotes a group wherein the aryl residue is as defined hereinabove, which is attached via an oxygen atom. The preferred aryloxy group is phenyloxy, optionally substituted by halo, e.g. F, as well as those specifically illustrated by the examples herein below.

The term "$C_{1-6}$-alkyl" denotes a saturated straight- or branched-chain hydrocarbon group containing from 1 to 6 carbon atoms, for example, methyl, ethyl, propyl, isopropyl, n-butyl, i-butyl, 2-butyl, t-butyl as well as those specifically illustrated by the examples herein below. Preferred $C_{1-6}$-alkyl groups are $C_{1-4}$-groups, i.e. with 1-4 carbon atoms.

The term "$C_{1-6}$-alkoxy" denotes a group wherein the alkyl residues are as defined above, which is attached via an oxygen atom. Preferred $C_{1-6}$-alkoxy groups are methoxy and ethoxy as well as those specifically illustrated by the examples herein below.

The term "$C_{2-6}$-alkenyl" denotes a carbon chain of 2 to 6 carbon atoms comprising a double bond in its chain. $C_{2-6}$-alkenyl groups include ethenyl, propen-1-yl, propen-2-yl, buten-1-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "benzyloxy" denotes a benzyl group attached via an oxygen atom.

The term "halogen" or "halo" denotes chlorine (Cl), iodine (I), fluorine (F) and bromine (Br).

The term "$C_{1-6}$-haloalkyl" denotes a $C_{1-6}$-alkyl group as defined above which is substituted by one or more halogen atom. Examples of $C_{1-6}$-haloalkyl include, but are not limited to, methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred $C_{1-6}$-haloalkyl are difluoro- or trifluoro-methyl or ethyl.

"$C_{1-6}$-haloalkoxy" denotes a $C_{1-6}$-alkoxy group as defined above which is substituted by one or more halogen atoms. Examples of $C_{1-6}$-haloalkoxy include, but are not limited to, methoxy or ethoxy, substituted by one or more Cl, F, Br or I atom(s) as well as those groups specifically illustrated by the examples herein below. Preferred $C_{1-6}$-haloalkoxy are difluoro- or trifluoro-methoxy or ethoxy.

The term "$C_{3-6}$-cycloalkyl" denotes a monovalent or divalent saturated carbocyclic moiety consisting of a monocyclic ring. Cycloalkyl can optionally be substituted with one, two, three or four substituents, wherein each substituent is independently hydroxy, $C_{1-6}$-alkyl, $C_{1-6}$-alkoxy, halogen, or amino, unless otherwise specifically indicated. Examples of cycloalkyl moieties include optionally substituted cyclopropyl, optionally substituted cyclobutyl, optionally substituted cyclopentyl and optionally substituted cyclohexyl as well as those specifically illustrated by the examples herein below.

The term "4 to 7 membered heterocycloalkyl" means a monovalent saturated moiety, consisting of one ring of 4 to 7 atoms as ring members, including one, two, or three heteroatoms chosen from nitrogen, oxygen or sulfur, the rest being carbon atoms. 4 to 7 membered heterocycloalkyl can optionally be substituted with one, two, three or four substituents, wherein each substituent is independently hydroxy, $C_{1-6}$-alkyl, $C_{1-6}$-alkoxy, $C_{1-6}$-thioalkyl, halo, $C_{1-6}$-haloalkyl, $C_{1-6}$-hydroxyalkyl, alkoxycarbonyl, amino, $C_{1-6}$-alkylamino, di($C_{1-6}$)alkylamino, aminocarbonyl, or carbonylamino, unless otherwise specifically indicated. Examples of heterocyclic moieties include, but are not limited to, optionally substituted oxetane, optionally substituted tetrahydro-furanyl, optionally substituted piperidinyl, optionally substituted pyrrolidinyl, optionally substituted morpholinyl, optionally substituted piperazinyl, and the like or those which are specifically exemplified herein. Substituents can be selected from $C_{1-6}$-alkyl, $C_{1-6}$-alkoxy, $C_{1-6}$-haloalkyl, halo, CN, OH, and $NH_2$, as well as those substituents which are specifically illustrated in the examples hereinafter. Preferred 4 to 7 membered heterocycloalkyl are 5 to 6 membered heterocycloalkyl.

The term "5 or 6 membered heteroaryl" means an aromatic ring of 5 or 6 ring atoms as ring members containing one, two, or three ring heteroatoms selected from N, O, or S, the rest being carbon atoms. 5 or 6 heteroaryl can optionally be substituted with one, two, three or four substituents, wherein each substituent is independently hydroxy, $C_{1-6}$-alkyl, $C_{1-6}$-alkoxy, $C_{1-6}$-thioalkyl, halo, $C_{1-6}$-haloalkyl, $C_{1-6}$-hydroxyalkyl, alkoxycarbonyl, amino, $C_{1-6}$-alkylamino, di($C_{1-6}$)alkylamino, aminocarbonyl, or carbonylamino, unless otherwise specifically indicated. Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyrazinyl, optionally substituted pyridinyl, optionally substituted pyrimidinyl, optionally substituted furanyl, and those which are specifically exemplified herein.

The term "sulfonylaryl" denotes an aryl group as defined hereinabove which is attached via a sulfonyl group.

The term "9 or 10 membered bicyclic heteroaryl" means an aromatic bicyclic ring of 9 or 10 ring atoms as ring members containing one, two, or three ring heteroatoms selected from N, O, or S, the rest being carbon atoms. 9 or 10 membered bicyclic heteroaryl can optionally be substituted with one, two, three or four substituents, wherein each substituent is independently hydroxy, —C(O), $C_{1-6}$-alkyl, $C_{1-6}$-alkoxy, $C_{1-6}$-thioalkyl, halo, $C_{1-6}$-haloalkyl, $C_{1-6}$-hydroxyalkyl, alkoxycarbonyl, amino, $C_{1-6}$-alkylamino, di($C_{1-6}$)alkylamino, aminocarbonyl, or carbonylamino, unless otherwise specifically indicated. Examples of 9 membered bicyclic heteroaryl moieties include, but are not limited to, optionally substituted indolyl, optionally substituted thieno[2,3-c]pyridinyl, thieno[3,2-c]pyridinyl, benzoxazolyl, benzisoxazolyl as well as those 9 membered bicyclic heteroaryl which are specifically exemplified herein.

The expression "two $R^2$ together with the indole ring to which they are attached form an oxo or dioxo bridge" denotes an oxo or dioxo bridge of the following formulae:

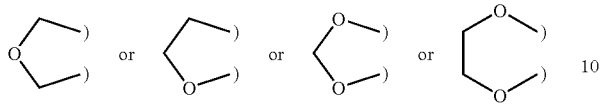

which bind two adjacent carbon atoms of the phenyl or indole ring of the compound of formula (I) to which $R^2$ is binding.

Analogously, the expression "oxo or dioxo bridge" denotes an oxo or dioxo bridge of the following formulae:

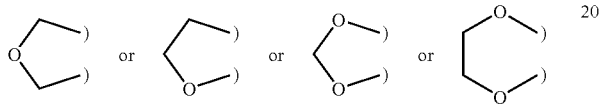

Examples of group illustrating the expression "$R^1$ and $R^3$ together with the indole ring to which they are attached form a 5 or 6 membered heterocycloalkyl which is optionally substituted by =O" are:

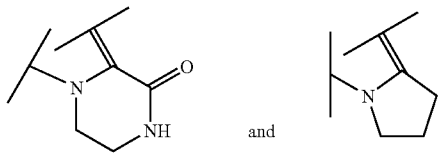

as well as those specifically illustrated by the examples.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid, as well as those specifically illustrated by the examples herein below.

"Therapeutically effective amount" means an amount that is effective to prevent, alleviate or ameliorate symptoms of disease or prolong the survival of the subject being treated.

The present invention provides compounds of formula (I)

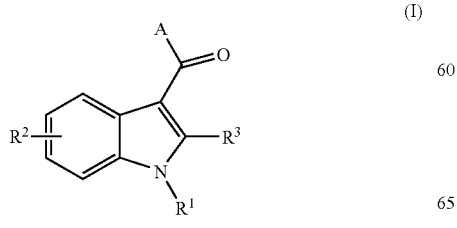

(I)

wherein
$R^1$ is H,
  $C_{1-6}$-alkyl substituted by CN, $C_{1-6}$-alkoxy, OH, halo, or $NR^i R^{ii}$,
  $C_{2-6}$-alkyl,
  aryl, 5 or 6 membered heteroaryl or sulfonylaryl each of which is optionally substituted by one or more B,
  —$(CH_2)_m$—$R^a$ wherein $R^a$ is:
    CN,
    $OR^i$,
    $NR^i R^{ii}$, or
    $C_{3-6}$-cycloalkyl, 4 to 7 membered-heterocycloalkyl, aryl, or 5 or 6 membered heteroaryl each of which is optionally substituted by one or more B,
  or —$(CH_2)_n$—(CO)—$R^b$ or —$(CH_2)_n$—$(SO_2)$—$R^b$, wherein $R^b$ is:
    $C_{1-6}$-alkyl,
    $C_{1-6}$-alkoxy,
    $C_{3-6}$-cycloalkyl,
    —$(CH_2)_m$—$NR^{iii} R^{iv}$,
    $NR^i R^{ii}$, or
    $C_{3-6}$-cycloalkyl, 4 to 7 membered-heterocycloalkyl, aryl, or 5 or 6 membered heteroaryl each of which is optionally substituted by one or more B,
  or $R^1$ and $R^3$ together with the indole ring to which they are attached form a 5 or 6 membered heterocycloalkyl which is optionally substituted by =O, C(O)O—$C_{1-6}$-alkyl or $C_{1-6}$-alkyl;

there is one or more $R^2$, wherein each $R^2$ is the same or different,
$R^2$ is one or more H, OH, halo, CN, nitro, $C_{1-6}$-alkoxy, —O—$CH_2$—$C_{2-6}$-alkenyl, benzyloxy, $C_{1-6}$-haloalkoxy, or $C_{1-6}$-alkyl optionally substituted by —$NR^{iii} R^{iv}$ or halo,
  or two $R^2$ together with the indole ring to which they are attached form an oxo or dioxo bridge;

$R^3$ is H,
  F,
  —(CO)—$R^c$, wherein $R^c$ is:
    $C_{1-6}$-alkyl,
    —$(CH_2)_n$—$NR^i R^{ii}$,
    —$(CH_2)_n$—$NR^{iii} R^{iv}$, or
    5 or 6 membered heterocycloalkyl optionally substituted by $C_{1-6}$-alkyl,
  or $C_{1-6}$-alkyl which is optionally substituted by
    halo,
    $NR^i R^{ii}$,
    $NR^{iii} R^{iv}$,
    —O(CO)—$C_{1-6}$-alkyl, or
    —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

A is selected from the group consisting of (a), (a'), (b), (c) and (d):

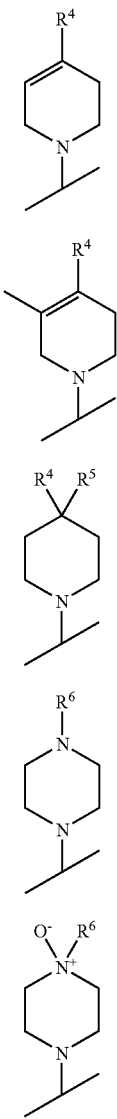

wherein
R⁴ is —NH(CO)Rᵉ, wherein Rᵉ is
  $C_{1-6}$-alkoxy or aryl each of which is optionally substituted by halo,
  $C_{1-6}$-alkoxy, or
  CN,
  or aryl, 5 or 6 membered heteroaryl, benzyl, aryloxy or a 9 or 10-membered bicyclic heteroaryl ring, each of which is optionally substituted by CN, halo, $C_{1-6}$-alkyl, $C_{1-6}$-alkoxy, $C_{1-6}$-haloalkyl, nitro, hydroxyl, $NR^iR^{ii}$, $NR^{iii}R^{iv}$, $C_{1-6}$-alkoxy-$C_{1-6}$-alkylene, $S(O)_2$—$C_{1-6}$-alkyl, or $C_{1-6}$-haloalkoxy, or by an oxo or dioxo bridge;
R⁵ is H, OH, CN, $COOR^{iii}$ or $CONR^{iii}R^{iv}$;
R⁶ is $C_{2-6}$-alkyl,
  —C(O)—$R^f$ wherein $R^f$ is an aryl group substituted by halo, $C_{1-6}$-alkoxy, or CN, aryl, 5 or 6 membered heteroaryl, or a 9 or 10-membered bicyclic heteroaryl ring each of which is optionally substituted by halo, $C_{1-6}$-alkyl, $C_{1-6}$-alkoxy, $C_{1-6}$-haloalkyl, CN, nitro, $NR^iR^{ii}$, $NR^{iii}R^{iv}$, $C_{1-6}$-alkoxy-$C_{1-6}$-alkylene, COOH, $S(O)_2$—$C_{1-6}$-alkyl, hydroxyl, or $C_{1-6}$-haloalkoxy, or by an oxo or dioxo bridge,
  or benzyl substituted by halo, $C_{1-6}$-alkyl, or $C_{1-6}$-haloalkyl or by an oxo- or dioxo bridge;
B is halo,
  CN,
  $NR^iR^{ii}$,
  $C_{1-6}$-alkyl optionally substituted by CN, halo or $C_{1-6}$-alkoxy,
  $C_{1-6}$-haloalkyl,
  $C_{1-6}$-alkoxy,
  $C_{1-6}$-haloalkoxy,
  $C_{3-6}$-cycloalkyl,
  —C(O)O—$C_{1-6}$-alkyl,
  —C(O)$NR^iR^{ii}$,
  —C(O)—$C_{1-6}$-alkyl,
  —S(O)$_2$—$C_{1-6}$-alkyl,
  —S(O)$_2$—$NR^iR^{ii}$, or
  $(CR^{iii}R^{iv})_n$-phenyl or $(CR^{iii}R^{iv})_n$-5 or 6 membered heteroaryl wherein the phenyl or 5 or 6 membered heteroaryl moiety is optionally substituted by one or more substituent(s) selected from the group consisting of:
    halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—$NR^iR^{ii}$, —C(O)—$C_{1-6}$-alkyl, —S(O)$_2$—$C_{1-6}$-alkyl, and —S(O)$_2$—$NR^iR^{ii}$;
$R^i$ and $R^{ii}$ are each independently H, $C_{1-6}$-alkyl, $C_{1-6}$-alkyl-$NR^{iii}R^{iv}$, —(CO)O—$C_{1-6}$-alkyl, —C(O)—$NR^{iii}R^{iv}$, —C(O)—$C_{1-6}$-alkyl, —S(O)$_2$—$C_{1-6}$-alkyl or —S(O)$_2$—$NR^{iii}R^{iv}$;
$R^{iii}$ and $R^{iv}$ are each independently H or $C_{1-6}$-alkyl;
m is 1 to 6; and
n is 0 to 4;
and pharmaceutically acceptable salts thereof.

In certain embodiments of the invention, the compounds of formula (I) are those compounds wherein:
R¹ is H,
  $C_{1-6}$-alkyl optionally substituted by CN or $C_{1-6}$-alkoxy, aryl, 5 or 6 membered heteroaryl or sulfonylaryl each of which is optionally substituted by one or more B,
  —(CH$_2$)$_m$—$R^a$ wherein $R^a$ is:
    CN,
    $OR^i$,
    $NR^iR^{ii}$, or
    $C_{3-6}$-cycloalkyl, 4 to 7 membered-heterocycloalkyl, aryl, or 5 or 6 membered heteroaryl each of which is optionally substituted by one or more B,
  or —(CH$_2$)$_n$—(CO)—$R^b$ or —(CH$_2$)$_n$—(SO$_2$)—$R^b$, wherein $R^b$ is:
    $C_{1-6}$-alkyl,
    $C_{1-6}$-alkoxy,
    $C_{3-6}$-cycloalkyl,
    —(CH$_2$)$_m$—$NR^{iii}R^{iv}$,
    $NR^iR^{ii}$, or
    $C_{3-6}$-cycloalkyl, 4 to 7 membered-heterocycloalkyl, aryl, or 5 or 6 membered heteroaryl each of which is optionally substituted by one or more B,
  or R¹ and R³ together with the indole ring to which they are attached form a 5 or 6 membered heterocycloalkyl which is optionally substituted by (CO);
there is one or more R², wherein each R² is the same or different, $R^2$ is one or more H, OH, halo, CN, nitro, $C_{1-6}$-alkyl optionally substituted by $-NR^{iii}R^{iv}$, $C_{1-6}$-alkoxy, $-O-CH_2-C_{2-6}$-alkenyl, or benzyloxy, or two $R^2$ together with the indole ring to which they are attached form an oxo or dioxo bridge;

$R^3$ is H,
halo,
$-(CO)-R^c$, wherein $R^c$ is:
$C_{1-6}$-alkyl,
$-(CH_2)_n-NR^iR^{ii}$,
$-(CH_2)_n-NR^{iii}R^{iv}$, or
5 or 6 membered heterocycloalkyl optionally substituted by $C_{1-6}$-alkyl,
or $C_{1-6}$-alkyl or aryl, each of which is optionally substituted by
halo,
$-O(CO)-C_{1-6}$-alkyl, or
$-NH(CO)R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

A is selected from the group consisting of (a), (b), (c) and (d):

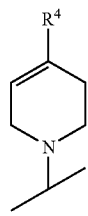 (a)

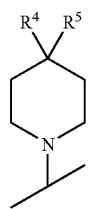 (b)

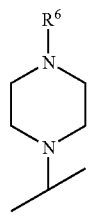 (c)

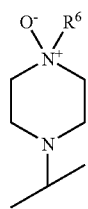 (d)

wherein
$R^4$ is $-NH(CO)R^e$, wherein $R^e$ is $C_{1-6}$-alkoxy or aryl optionally substituted by halo,
$C_{1-6}$-alkoxy, or
CN, or aryl, 5 or 6 membered heteroaryl, benzyl, aryloxy or a 9 or 10-membered bicyclic heteroaryl ring each of which is optionally substituted by CN, halo, $C_{1-6}$-alkyl, $C_{1-6}$-alkoxy, or $C_{1-6}$-haloalkyl, or by a dioxo bridge;

$R^5$ is H, OH, CN, $COOR^{iii}$ or $CONR^{iii}R^{iv}$;

$R^6$ is $C_{1-6}$-alkyl,
$-C(O)-R^f$ wherein $R^f$ is an aryl group optionally substituted by halo, $C_{1-6}$-alkoxy,
or CN,
or aryl, 5 or 6 membered heteroaryl, benzyl, or a 9 or 10-membered bicyclic heteroaryl ring each of which is optionally substituted by halo, $C_{1-6}$-alkyl, $C_{1-6}$-alkoxy, $C_{1-6}$-haloalkyl, or CN or by a dioxo bridge;

B is halo,
CN,
$NR^iR^{ii}$,
$C_{1-6}$-alkyl optionally substituted by CN, halo or $C_{1-6}$-alkoxy,
$C_{1-6}$-alkoxy,
$C_{1-6}$-haloalkoxy,
$C_{3-6}$-cycloalkyl,
$-C(O)O-C_{1-6}$-alkyl,
$-C(O)NR^iR^{ii}$,
$-C(O)-C_{1-6}$-alkyl,
$-S(O)_2-C_{1-6}$-alkyl,
$-S(O)_2-NR^iR^{ii}$,
$(CR^{iii}R^{iv})_n$-phenyl, or $(CR^{iii}R^{iv})_n$-5 or 6 membered heteroaryl wherein the phenyl or 5 or 6 membered heteroaryl moiety is optionally substituted by one or more substituent(s) selected from the group consisting of:
halo, CN, $NR^iR^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, $-C(O)O-C_{1-6}$-alkyl, $-C(O)-NR^iR^{ii}$, $-C(O)-C_{1-6}$-alkyl, $-S(O)_2-C_{1-6}$-alkyl, and $-S(O)_2-NR^iR^{ii}$;

$R^i$ and $R^{ii}$ are each independently H, $C_{1-6}$-alkyl, $C_{1-6}$-alkyl-$NR^{iii}R^{iv}$, $-(CO)O-C_{1-6}$-alkyl, $-C(O)-NR^{iii}R^{iv}$, $-C(O)-C_{1-6}$-alkyl, $-S(O)_2-C_{1-6}$-alkyl or $-S(O)_2-NR^{iii}R^{iv}$;

$R^{iii}$ and $R^{iv}$ are each independently H or $C_{1-6}$-alkyl;

m is 1 to 6; and n is 0 to 4;

and pharmaceutically acceptable salts thereof.

In certain embodiments of the invention, the compounds of formula (I) are those compounds wherein:

$R^1$ is H,
$C_{1-6}$-alkyl optionally substituted by CN or $C_{1-6}$-alkoxy,
aryl,
5 or 6 membered heteroaryl,
sulfonylaryl,
$-(CH_2)_m-R^a$ wherein $R^a$ is $C_{3-6}$-cycloalkyl, 5 or 6 membered-heterocycloalkyl, aryl, or 5 or 6 membered heteroaryl each of which is optionally substituted by one or more substituents selected from the group consisting of:
halo, CN, $C_{1-6}$-alkyl, $C_{1-6}$-alkoxy, $C_{1-6}$-haloalkoxy, $-C(O)O-C_{1-6}$-alkyl and phenyl optionally substituted by halo, $C_{1-6}$-alkyl, $C_{1-6}$-haloalkyl or $C_{1-6}$-alkoxy,
$-(CH_2)_m-NR^iR^{ii}$,
or $-(CH_2)_n-(CO)-R^b$, wherein $R^b$ is aryl or 5 or 6 membered-heterocycloalkyl;

there is one or more $R^2$, wherein each $R^2$ is the same or different, $R^2$ is one or more H, halo, CN, nitro, $C_{1-6}$-alkyl, $C_{1-6}$-alkoxy, —O—$CH_2$—$C_{2-6}$-alkenyl, or benzyloxy, or two $R^2$ together with the indole ring to which they are attached form an oxo or dioxo bridge;

$R^3$ is H,
halo,
—(CO)—$R^c$, wherein $R^c$ is $C_{1-6}$-alkyl, 5 or 6 membered heterocycloalkyl optionally substituted by $C_{1-6}$-alkyl, or $R^c$ is —$(CH_2)_n$—$NR^iR^{ii}$,
or $C_{1-6}$-alkyl or aryl, each of which is optionally substituted by
—O(CO)—$C_{1-6}$-alkyl or —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;

$R^i$ and $R^{ii}$ are each independently selected from H, $C_{1-6}$-alkyl and —(CO)O—$C_{1-6}$-alkyl;

m is 1 to 6; and
n is 0 to 4;

A is selected from the group consisting of (a), (b), (c) and (d):

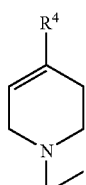

(a)

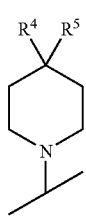

(b)

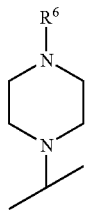

(c)

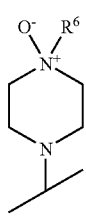

(d)

wherein
$R^4$ is —NH(CO)$R^e$, wherein $R^e$ is $C_{1-6}$-alkoxy, or aryl optionally substituted by halo,
or is aryl, benzyl, aryloxy or a 9 or 10-membered bicyclic heteroaryl ring each of which is optionally substituted by halo, $C_{1-6}$-alkyl, $C_{1-6}$-alkoxy, or $C_{1-6}$-haloalkyl, or by a dioxo bridge;

$R^5$ is H, OH or CN;
$R^6$ is $C_{1-6}$-alkyl,
—C(O)—$R^f$ wherein $R^f$ is an aryl group optionally substituted by halo, or aryl, benzyl, or a 9 or 10-membered bicyclic heteroaryl ring each of which is optionally substituted by halo, $C_{1-6}$-alkyl, $C_{1-6}$-alkoxy, or $C_{1-6}$-haloalkyl, or by a dioxo bridge;

and pharmaceutically acceptable salts thereof.

In certain embodiments of the invention, the compounds of formula (I) are those compounds wherein:

$R^1$ is H,
$C_{1-6}$-alkyl substituted by $NR^iR^{ii}$,
—$(CH_2)_m$—$R^a$ wherein $R^a$ is:
$NR^iR^{ii}$ or
5 to 6 membered-heterocycloalkyl, aryl, or 5 or 6 membered heteroaryl each of which is optionally substituted by one or more B,
or —$(CH_2)_n$—(CO)—$R^b$ or —$(CH_2)_n$—($SO_2$)—$R^b$, wherein $R^b$ is:
$C_{1-6}$-alkyl,
$C_{1-6}$-alkoxy,
$NR^iR^{ii}$, or
5 to 6 membered-heterocycloalkyl, aryl, or 5 or 6 membered heteroaryl which are optionally substituted by one or more B, or $R^1$ and $R^3$ together with the indole ring to which they are attached form a 5 or 6 membered heterocycloalkyl which is optionally substituted by =O, C(O)O—$C_{1-6}$-alkyl or $C_{1-6}$-alkyl;

there is one or more $R^2$, wherein each $R^2$ is the same or different, $R^2$ is one or more H, halo, or $C_{1-6}$-alkyl;
$R^3$ is H or $C_{1-6}$-alkyl;

A is selected from the group consisting of (a), (a'), (b), (c) and (d):

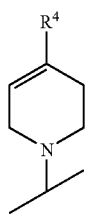

(a)

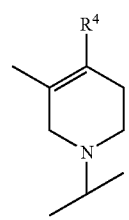

(a')

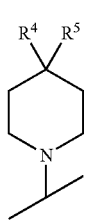

(b)

-continued

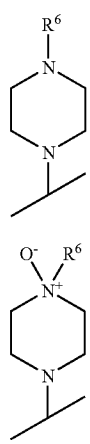

(c)

(d)

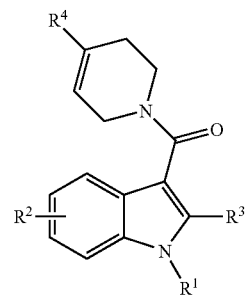

(I-a)

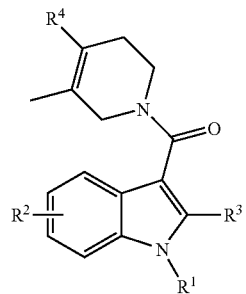

(I-a')

wherein
R$^4$ is —NH(CO)R$^e$, wherein R$^e$ is C$_{1-6}$-alkoxy, or aryl optionally substituted by halo, or is aryl, 5 or 6 membered heteroaryl, benzyl, aryloxy or a 9 or 10-membered bicyclic heteroaryl ring, each of which is optionally substituted by halo, C$_{1-6}$-alkyl, C$_{1-6}$-alkoxy, C$_{1-6}$-haloalkyl, nitro, hydroxyl, or C$_{1-6}$-haloalkoxy, or by an oxo or dioxo bridge; and R$^5$ is H, OH, or CN;

R$^6$ is aryl, 5 or 6 membered heteroaryl, or a 9 or 10-membered bicyclic heteroaryl ring each of which is optionally substituted by halo, C$_{1-6}$-alkyl, C$_{1-6}$-alkoxy, C$_{1-6}$-haloalkyl, CN, nitro, NR$^i$R$^{ii}$, NR$^{iii}$R$^{iv}$, C$_{1-6}$-alkoxy-C$_{1-6}$-alkylene, COOH, or S(O)$_2$—C$_{1-6}$-alkyl, or by an oxo or dioxo bridge;

B is halo, C$_{1-6}$-alkyl optionally substituted by CN, halo or C$_{1-6}$-alkoxy, or C$_{1-6}$-alkoxy;

R$^i$ and R$^{ii}$ are each independently H, C$_{1-6}$-alkyl, C$_{1-6}$-alkyl-NR$^{iii}$R$^{iv}$, —C(O)—C$_{1-6}$-alkyl or —S(O)$_2$—C$_{1-6}$-alkyl;

R$^{iii}$ and R$^{iv}$ are each independently H or C$_{1-6}$-alkyl;

m is 1 to 6; and n is 0 to 4;

and pharmaceutically acceptable salts thereof.

Preferably, the invention encompasses compounds according to the general formula (I) as described herein, with the proviso that R$^1$, R$^2$ and R$^3$ are not simultaneously H, as well as pharmaceutical acceptable salts thereof.

Preferably, the invention encompasses compounds according to the general formula (I) as described herein, with the proviso that R$^4$ is not a 1H-benzimidazole derivative:

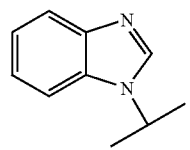

optionally substituted by CN, halo, C$_{1-6}$-alkyl, C$_{1-6}$-alkoxy, C$_{1-6}$-haloalkyl, nitro, hydroxyl, NR$^i$R$^{ii}$, NR$^{iii}$R$^{iv}$, C$_{1-6}$-alkoxy-C$_{1-6}$-alkylene, S(O)$_2$—C$_{1-6}$-alkyl, or C$_{1-6}$-haloalkoxy, or by an oxo or dioxo bridge.

Also encompassed by the compounds of formula (I) are the following compounds of formula (I-a) or (I-a') according to the invention:

wherein R$^1$ to R$^4$ are as defined hereinabove for formula (I).

Preferred compounds of formula (I-a) are those compounds wherein,

R$^1$ is H or —(CH$_2$)$_m$—R$^a$ wherein R$^a$ is aryl and m is 1 to 6;

there is one or more R$^2$, wherein each R$^2$ is the same or different,

R$^2$ is one or more H or halo;

R$^3$ is H or C$_{1-6}$-alkyl;

R$^4$ is aryl which is optionally substituted by halo or C$_{1-6}$-alkoxy;

and pharmaceutically acceptable salts thereof.

Again, it is preferred that R$^1$, R$^2$ and R$^3$ are not simultaneously H.

Examples of compounds according to the invention are:

Benzyl-2-methyl-1H-indol-3-yl)-[4-(4-fluoro-phenyl)-3,6-dihydro-2H-pyridin-1-yl]-methanone;

Benzyl-2-methyl-1H-indol-3-yl)-(4-phenyl-3,6-dihydro-2H-pyridin-1-yl)-methanone;

Benzyl-2-methyl-1H-indol-3-yl)-[4-(2-methoxy-phenyl)-3,6-dihydro-2H-pyridin-1-yl]-methanone;

(6-Chloro-1H-indol-3-yl)-(4-phenyl-3,6-dihydro-2H-pyridin-1-yl)-methanone;

(6-Chloro-1H-indol-3-yl)-[4-(4-fluoro-phenyl)-3,6-dihydro-2H-pyridin-1-yl]-methanone;

(6-Chloro-1H-indol-3-yl)-(4-phenyl-3,6-dihydro-2H-pyridin-1-yl)-methanone;

(6-Chloro-1H-indol-3-yl)-[4-(4-fluoro-phenyl)-3,6-dihydro-2H-pyridin-1-yl]-methanone;

(6-Chloro-1H-indol-3-yl)-[4-(4-chloro-phenyl)-3,6-dihydro-2H-pyridin-1-yl]-methanone; and Benzyl-2-methyl-1H-indol-3-yl)-(5-methyl-4-phenyl-3,6-dihydro-2H-pyridin-1-yl)-methanone.

Also encompassed by the compounds of formula (I) are the following compounds of formula (I-b) according to the invention:

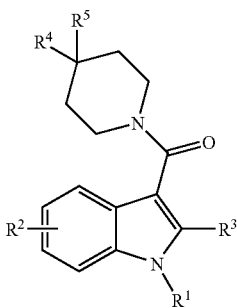

(I-b)

wherein $R^1$ to $R^5$ are as defined hereinabove for formula (I).

Preferred compounds of formula (I-b) are those compounds wherein, $R^1$ is H,
—$(CH_2)_m$—$R^a$ wherein $R^a$ is:
$NR^iR^{ii}$, or
aryl, or 5 or 6 membered heteroaryl each of which is optionally substituted by one or more halo, $C_{1-6}$-alkyl, $C_{1-6}$-alkoxy,
or —$(CH_2)_n$—(CO)—$R^b$ or —$(CH_2)_n$—$(SO_2)$—$R^b$, wherein $R^b$ is:
$C_{1-6}$-alkyl,
$C_{1-6}$-alkoxy,
$NR^iR^{ii}$, or
5 to 6 membered-heterocycloalkyl, or 5 or 6 membered heteroaryl each of which is optionally substituted by one or more halo, $C_{1-6}$-alkyl, or $C_{1-6}$-alkoxy, or $R^1$ and $R^3$ together with the indole ring to which they are attached form a 5 or 6 membered heterocycloalkyl which is optionally substituted by C(O)O—$C_{1-6}$-alkyl or $C_{1-6}$-alkyl;

there is one or more $R^2$, wherein each $R^2$ is the same or different, $R^2$ is one or more H, halo or $C_{1-6}$-alkyl;

$R^3$ is H or $C_{1-6}$-alkyl;

$R^4$ is —NH(CO)$R^e$, wherein $R^e$ is $C_{1-6}$-alkoxy or aryl which is optionally substituted by halo,
or is aryl, benzyl, aryloxy or a 9 or 10-membered bicyclic heteroaryl ring each of which is optionally substituted by halo, $C_{1-6}$-alkyl, $C_{1-6}$-alkoxy, $C_{1-6}$-haloalkyl, nitro, hydroxyl, or $C_{1-6}$-haloalkoxy or by an oxo or dioxo bridge; and $R^5$ is H, OH or CN;

$R^i$ and $R^{ii}$ are each independently H, $C_{1-6}$-alkyl, or $C_{1-6}$-alkyl-$NR^{iii}R^{iv}$;

$R^{iii}$ and $R^{iv}$ are each independently H or $C_{1-6}$-alkyl;

m is 1 to 6; and n is 0 to 4;

and pharmaceutically acceptable salts thereof.

Again, it is preferred that $R^1$, $R^2$ and $R^3$ are not simultaneously H.

Moreover, it is preferred that $R^4$ is not an 1H-benzimidazole derivative as described hereinabove.

Examples of compounds of formula (I-b) according to the invention are:

(4-Benzyl-4-hydroxy-piperidin-1-yl)-(1-benzyl-2-methyl-1H-indol-3-yl)-methanone;
(4-Benzyl-4-hydroxy-piperidin-1-yl)-[1-(2-chloro-benzyl)-2-methyl-1H-indol-3-yl]-methanone;
Benzyl-5-chloro-2-methyl-1H-indol-3-yl)-(4-benzyl-4-hydroxy-piperidin-1-yl)-methanone;
(4-Benzyl-4-hydroxy-piperidin-1-yl)-[5-chloro-1-(3-methoxy-benzyl)-2-methyl-1H-indol-3-yl]-methanone;
(4-Benzyl-4-hydroxy-piperidin-1-yl)-[1-(2-methoxy-benzyl)-2-methyl-1H-indol-3-yl]-methanone;
Benzyl-2-methyl-1H-indol-3-yl)-[4-(3-fluoro-phenoxy)-piperidin-1-yl]-methanone;
Benzyl-2-methyl-1H-indol-3-yl)-(4-hydroxy-4-phenyl-piperidin-1-yl)-methanone;
Benzyl-2-methyl-1H-indol-3-yl)-[4-(4-fluoro-phenyl)-4-hydroxy-piperidin-1-yl]-methanone;
Benzyl-2-methyl-1H-indol-3-yl)-[4-(4-chloro-3-trifluoromethyl-phenyl)-4-hydroxy-piperidin-1-yl]-methanone;
(4-Benzo[1,3]dioxol-5-yl-4-hydroxy-piperidin-1-yl)-(1-benzyl-2-methyl-1H-indol-3-yl)-methanone;
Benzyl-2-methyl-1H-indol-3-yl)-(4-hydroxy-4-p-tolyl-piperidin-1-yl)-methanone;
Benzyl-2-methyl-1H-indol-3-yl)-[4-hydroxy-4-(3-trifluoromethyl-phenyl)-piperidin-1-yl]-methanone;
(6-Chloro-1H-indol-3-yl)-[4-hydroxy-4-(3-trifluoromethyl-phenyl)-piperidin-1-yl]-methanone;
1-(6-Chloro-1H-indole-3-carbonyl)-4-phenyl-piperidine-4-carbonitrile;
(6-Chloro-1H-indol-3-yl)-(4-hydroxy-4-p-tolyl-piperidin-1-yl)-methanone;
(6-Chloro-1H-indol-3-yl)-[4-(4-chloro-phenyl)-4-hydroxy-piperidin-1-yl]-methanone;
(6-Chloro-1H-indol-3-yl)-[4-(4-chloro-3-trifluoromethyl-phenyl)-4-hydroxy-piperidin-1-yl]-methanone;
[4-(4-Bromo-phenyl)-4-hydroxy-piperidin-1-yl]-(6-chloro-1H-indol-3-yl)-methanone;
[1-(6-Chloro-1H-indole-3-carbonyl)-piperidin-4-yl]-carbamic acid tert-butyl ester;
N-[1-(6-Chloro-1H-indole-3-carbonyl)-piperidin-4-yl]-2-fluoro-benzamide;
(6-Chloro-1H-indol-3-yl)-[4-(4-chloro-phenyl)-4-hydroxy-piperidin-1-yl]-methanone;
(6-Chloro-1H-indol-3-yl)-[4-(4-nitro-phenyl)-piperidin-1-yl]-methanone;
(6-Chloro-1H-indol-3-yl)-(4-methoxy-4-phenyl-piperidin-1-yl)-methanone;
(6-Chloro-1H-indol-3-yl)-[4-(2-methoxy-phenyl)-piperidin-1-yl]-methanone;
(6-Chloro-1H-indol-3-yl)-[4-(2,3-dihydro-benzofuran-7-yl)-piperidin-1-yl]-methanone;
N-(2-Amino-ethyl)-2-{6-chloro-3-[4-(2,3-dihydro-benzofuran-7-yl)-piperidine-1-carbonyl]-indol-1-yl}-acetamide;
2-{6-Chloro-3-[4-(2,3-dihydro-benzofuran-7-yl)-piperidine-1-carbonyl]-indol-1-yl}-N-(2-methylamino-ethyl)-acetamide;
(6-Chloro-1H-indol-3-yl)-[4-(2-trifluoromethoxy-phenyl)-piperidin-1-yl]-methanone;
(6-Chloro-1H-indol-3-yl)-[4-(2-trifluoromethyl-phenyl)-piperidin-1-yl]-methanone;
2-{6-Chloro-3-[4-(2-trifluoromethoxy-phenyl)-piperidine-1-carbonyl]-indol-1-yl}-N-(2-dimethylamino-ethyl)-acetamide;
2-{6-Chloro-3-[4-(2-trifluoromethoxy-phenyl)-piperidine-1-carbonyl]-indol-1-yl}-acetamide;
2-{6-Chloro-3-[4-(2-trifluoromethoxy-phenyl)-piperidine-1-carbonyl]-indol-1-yl}-N-(2-methylamino-ethyl)-acetamide;
N-(2-Amino-ethyl)-2-{6-chloro-3-[4-(2-trifluoromethoxy-phenyl)-piperidine-1-carbonyl]-indol-1-yl}-acetamide;
2-{6-Chloro-3-[4-(2-trifluoromethyl-phenyl)-piperidine-1-carbonyl]-indol-1-yl}-acetamide;

2-{6-Chloro-3-[4-(2-trifluoromethyl-phenyl)-piperidine-1-carbonyl]-indol-1-yl}-N-(2-methylamino-ethyl)-acetamide or hydrochloride salt thereof;
N-(2-Amino-ethyl)-2-{6-chloro-3-[4-(2-trifluoromethyl-phenyl)-piperidine-1-carbonyl]-indol-1-yl}-acetamide or hydrochloride salt thereof;
2-{6-Chloro-3-[4-(2-trifluoromethyl-phenyl)-piperidine-1-carbonyl]-indol-1-yl}-N-(2-dimethylamino-ethyl)-acetamide;
[1-(2-Amino-ethyl)-6-chloro-1H-indol-3-yl]-[4-(2,3-dihydro-benzofuran-7-yl)-piperidin-1-yl]-methanone;
[1-(2-Amino-ethyl)-6-chloro-1H-indol-3-yl]-[4-(2-trifluoromethoxy-phenyl)-piperidin-1-yl]-methanone;
[1-(2-Amino-ethyl)-6-chloro-1H-indol-3-yl]-[4-(2-methoxy-phenyl)-piperidin-1-yl]-methanone;
[1-(2-Amino-ethyl)-6-chloro-1H-indol-3-yl]-[4-(2-fluoro-phenyl)-piperidin-1-yl]-methanone;
2-{6-Chloro-3-[4-(2-fluoro-phenyl)-piperidine-1-carbonyl]-indol-1-yl}-acetamide;
(6-Chloro-1H-indol-3-yl)-(3,4,5,6-tetrahydro-2H-[4,4']bipyridinyl-1-yl)-methanone;
(6-Chloro-2-methyl-1H-indol-3-yl)-[4-(2-methoxy-phenyl)-piperidin-1-yl]-methanone;
(6-Chloro-1-methanesulfonyl-1H-indol-3-yl)-[4-(2-methoxy-phenyl)-piperidin-1-yl]-methanone;
10-[4-(2-Methoxy-phenyl)-piperidine-1-carbonyl]-3,4-dihydro-1H-pyrazino[1,2-a]indole-2-carboxylic acid tert-butyl ester;
[4-(2-Methoxy-phenyl)-piperidin-1-yl]-(1,2,3,4-tetrahydro-pyrazino[1,2-a]indol-10-yl)-methanone or hydrochloride salt thereof; and
[4-(2-Methoxy-phenyl)-piperidin-1-yl]-(2-methyl-1,2,3,4-tetrahydro-pyrazino[1,2-a]indol-10-yl)-methanone.

Preferred examples of compounds of formula (I-b) according to the invention are:
Benzyl-2-methyl-1H-indol-3-yl)-[4-(4-chloro-phenyl)-4-hydroxy-piperidin-1-yl]-methanone;
Benzyl-2-methyl-1H-indol-3-yl)-[4-(4-bromo-phenyl)-4-hydroxy-piperidin-1-yl]-methanone;
(6-Chloro-1H-indol-3-yl)-(4-phenyl-piperidin-1-yl)-methanone;
(4-Benzo[1,3]dioxol-5-yl-4-hydroxy-piperidin-1-yl)-(6-chloro-1H-indol-3-yl)-methanone;
Benzyl-2-methyl-1H-indol-3-yl)-[4-(4-fluoro-phenyl)-piperidin-1-yl]-methanone;
(6-Chloro-1H-indol-3-yl)-[4-(3-chloro-phenyl)-piperidin-1-yl]-methanone;
(6-Chloro-1H-indol-3-yl)-[4-(2-hydroxy-phenyl)-piperidin-1-yl]-methanone;
(6-Chloro-1H-indol-3-yl)-[4-(4-fluoro-phenyl)-piperidin-1-yl]-methanone;
(6-Chloro-1H-indol-3-yl)-[4-(2-isopropoxy-phenyl)-piperidin-1-yl]-methanone;
2-{3-[4-(2,6-Dimethoxy-phenyl)-piperidine-1-carbonyl]-indol-1-yl}-1-(4-methyl-piperazin-1-yl)-ethanone;
2-{6-Chloro-3-[4-(2,6-dimethoxy-phenyl)-piperidine-1-carbonyl]-indol-1-yl}-N-(2-dimethylamino-ethyl)-acetamide;
2-{6-Chloro-3-[4-(2-methoxy-phenyl)-piperidine-1-carbonyl]-indol-1-yl}-1-piperazin-1-yl-ethanone;
2-{6-Chloro-3-[4-(2,3-dihydro-benzofuran-7-yl)-piperidine-1-carbonyl]-indol-1-yl}-N-(2-dimethylamino-ethyl)-acetamide;
2-{6-Chloro-3-[4-(2,3-dihydro-benzofuran-7-yl)-piperidine-1-carbonyl]-indol-1-yl}-1-piperazin-1-yl-ethanone;
2-{6-Chloro-3-[4-(2-methoxy-phenyl)-piperidine-1-carbonyl]-5-methyl-indol-1-yl}-N,N-dimethyl-acetamide;
2-{6-Chloro-3-[4-(2,3-dihydro-benzofuran-7-yl)-piperidine-1-carbonyl]-indol-1-yl}-acetamide;
2-{6-Chloro-3-[4-(2,6-dimethoxy-phenyl)-piperidine-1-carbonyl]-indol-1-yl}-N-(2-methylamino-ethyl)-acetamide;
2-{6-Chloro-3-[4-(2-trifluoromethoxy-phenyl)-piperidine-1-carbonyl]-indol-1-yl}-1-piperazin-1-yl-ethanone;
2-{6-Chloro-3-[4-(2-trifluoromethyl-phenyl)-piperidine-1-carbonyl]-indol-1-yl}-1-piperazin-1-yl-ethanone or hydrochloride salt thereof;
[6-Chloro-1-(2-methylamino-ethyl)-1H-indol-3-yl]-[4-(2-methoxy-phenyl)-piperidin-1-yl]-methanone;
2-{6-Chloro-3-[4-(2-fluoro-phenyl)-piperidine-1-carbonyl]-indol-1-yl}-N-(2-dimethylamino-ethyl)-acetamide;
2-{6-Chloro-3-[4-(2-fluoro-phenyl)-piperidine-1-carbonyl]-indol-1-yl}-N-(2-methylamino-ethyl)-acetamide or hydrochloride salt thereof;
N-(2-Amino-ethyl)-2-{6-chloro-3-[4-(2-fluoro-phenyl)-piperidine-1-carbonyl]-indol-1-yl}-acetamide or hydrochloride salt thereof;
2-{6-Chloro-3-[4-(5-fluoro-benzo[d]isoxazol-3-yl)-piperidine-1-carbonyl]-indol-1-yl}-N-methyl-acetamide;
2-{6-Chloro-3-[4-(2-fluoro-phenyl)-4-hydroxy-piperidine-1-carbonyl]-indol-1-yl}-N-methyl-acetamide; and
2-[6-Chloro-3-(3,4,5,6-tetrahydro-2H-[4,4']bipyridinyl-1-carbonyl)-indol-1-yl]-N-methyl-acetamide.

Particularly preferred examples of compounds of formula (I-b) according to the invention are:
Benzyl-2-methyl-1H-indol-3-yl)-(4-phenyl-piperidin-1-yl)-methanone;
(6-Chloro-1H-indol-3-yl)-[4-(2,6-dimethoxy-phenyl)-piperidin-1-yl]-methanone;
2-{6-Chloro-3-[4-(2,6-dimethoxy-phenyl)-piperidine-1-carbonyl]-indol-1-yl}-N,N-dimethyl-acetamide;
2-{6-Chloro-3-[4-(2,6-dimethoxy-phenyl)-piperidine-1-carbonyl]-indol-1-yl}-1-pyridin-2-yl-ethanone;
(6-Chloro-1-pyridin-4-ylmethyl-1H-indol-3-yl)-[4-(2,6-dimethoxy-phenyl)-piperidin-1-yl]-methanone;
(6-Chloro-1-pyridin-3-ylmethyl-1H-indol-3-yl)-[4-(2,6-dimethoxy-phenyl)-piperidin-1-yl]-methanone;
(6-Chloro-1-pyridin-2-ylmethyl-1H-indol-3-yl)-[4-(2,6-dimethoxy-phenyl)-piperidin-1-yl]-methanone;
[6-Chloro-1-(6-chloro-pyridin-3-ylmethyl)-1H-indol-3-yl]-[4-(2,6-dimethoxy-phenyl)-piperidin-1-yl]-methanone;
{6-Chloro-3-[4-(2,6-dimethoxy-phenyl)-piperidine-1-carbonyl]-indol-1-yl}-acetic acid tert-butyl ester;
(6-Chloro-1-pyrazin-2-ylmethyl-1H-indol-3-yl)-[4-(2,6-dimethoxy-phenyl)-piperidin-1-yl]-methanone;
[6-Chloro-1-(3,5-difluoro-benzyl)-1H-indol-3-yl]-[4-(2,6-dimethoxy-phenyl)-piperidin-1-yl]-methanone;
[6-Chloro-1-(2-dimethylamino-ethyl)-1H-indol-3-yl]-[4-(2,6-dimethoxy-phenyl)-piperidin-1-yl]-methanone;
2-{6-Chloro-3-[4-(2,6-dimethoxy-phenyl)-piperidine-1-carbonyl]-indol-1-yl}-1-(4-methyl-piperazin-1-yl)-ethanone;
[6-Chloro-1-(3,5-difluoro-benzyl)-1H-indol-3-yl]-[4-(2-methoxy-phenyl)-piperidin-1-yl]-methanone;
2-{6-Chloro-3-[4-(2-methoxy-phenyl)-piperidine-1-carbonyl]-indol-1-yl}-N,N-dimethyl-acetamide;
2-{6-Chloro-3-[4-(2-methoxy-phenyl)-piperidine-1-carbonyl]-indol-1-yl}-1-(4-methyl-piperazin-1-yl)-ethanone;
{6-Chloro-3-[4-(2-methoxy-phenyl)-piperidine-1-carbonyl]-indol-1-yl}-acetic acid tert-butyl ester;
2-{6-Chloro-3-[4-cyano-4-(2-methoxy-phenyl)-piperidine-1-carbonyl]-indol-1-yl}-N,N-dimethyl-acetamide;
2-{6-Chloro-3-[4-cyano-4-(2-fluoro-phenyl)-piperidine-1-carbonyl]-indol-1-yl}-N,N,-dimethyl-acetamide;

2-{3-[4-(2,6-Dimethoxy-phenyl)-piperidine-1-carbonyl]-indol-1-yl}-N,N-dimethyl-acetamide;
[6-Chloro-1-(2-methyl-pyridin-4-ylmethyl)-1H-indol-3-yl]-[4-(2,6-dimethoxy-phenyl)-piperidin-1-yl]-methanone;
2-{6-Chloro-3-[4-(2-isopropoxy-phenyl)-piperidine-1-carbonyl]-indol-1-yl}-N,N-dimethyl-acetamide;
2-{6-Chloro-3-[4-(2-isopropoxy-phenyl)-piperidine-1-carbonyl]-indol-1-yl}-1-(4-methyl-piperazin-1-yl)-ethanone;
2-{6-Chloro-3-[4-(2,6-dimethoxy-phenyl)-piperidine-1-carbonyl]-indol-1-yl}-1-piperazin-1-yl-ethanone;
2-{6-Chloro-3-[4-(2,3-dihydro-benzofuran-7-yl)-piperidine-1-carbonyl]-indol-1-yl}-1-(4-methyl-piperazin-1-yl)-ethanone;
2-{6-Chloro-3-[4-(2,3-dihydro-benzofuran-7-yl)-piperidine-1-carbonyl]-indol-1-yl}-N,N-dimethyl-acetamide;
2-{6-Chloro-3-[4-(2,3-dihydro-benzofuran-7-yl)-piperidine-1-carbonyl]-indol-1-yl}-N-methyl-acetamide;
2-{5,6-Dichloro-3-[4-(2-methoxy-phenyl)-piperidine-1-carbonyl]-indol-1-yl}-N,N-dimethyl-acetamide;
2-{6-Chloro-3-[4-(2,6-dimethoxy-phenyl)-piperidine-1-carbonyl]-indol-1-yl}-acetamide;
2-{6-Chloro-3-[4-(2,6-dimethoxy-phenyl)-piperidine-1-carbonyl]-indol-1-yl}-N-methyl-acetamide;
N-(2-Amino-ethyl)-2-{6-chloro-3-[4-(2,6-dimethoxy-phenyl)-piperidine-1-carbonyl]-indol-1-yl}-acetamide;
[6-Chloro-1-(2-dimethylamino-ethyl)-1H-indol-3-yl]-[4-(2,3-dihydro-benzofuran-7-yl)-piperidin-1-yl]-methanone;
2-{6-Chloro-3-[4-(2-trifluoromethoxy-phenyl)-piperidine-1-carbonyl]-indol-1-yl}-1-(4-methyl-piperazin-1-yl)-ethanone;
2-{6-Chloro-3-[4-(2-trifluoromethoxy-phenyl)-piperidine-1-carbonyl]-indol-1-yl}-N-methyl-acetamide;
2-{6-Chloro-3-[4-(2-trifluoromethoxy-phenyl)-piperidine-1-carbonyl]-indol-1-yl}-N,N-dimethyl-acetamide;
2-{6-Chloro-3-[4-(2-trifluoromethyl-phenyl)-piperidine-1-carbonyl]-indol-1-yl}-N-methyl-acetamide;
2-{6-Chloro-3-[4-(2-trifluoromethyl-phenyl)-piperidine-1-carbonyl]-indol-1-yl}-1-(4-methyl-piperazin-1-yl)-ethanone;
2-{6-Chloro-3-[4-(2-trifluoromethyl-phenyl)-piperidine-1-carbonyl]-indol-1-yl}-N,N-dimethyl-acetamide;
2-{6-Chloro-3-[4-(2-methoxy-phenyl)-piperidine-1-carbonyl]-indol-1-yl}-N-methyl-acetamide;
[6-Chloro-1-(2-methylamino-ethyl)-1H-indol-3-yl]-[4-(2,3-dihydro-benzofuran-7-yl)-piperidin-1-yl]-methanone;
[6-Chloro-1-(2-dimethylamino-ethyl)-1H-indol-3-yl]-[4-(2-methoxy-phenyl)-piperidin-1-yl]-methanone;
2-{6-Chloro-3-[4-(2-fluoro-phenyl)-piperidine-1-carbonyl]-indol-1-yl}-N-methyl-acetamide;
2-{6-Chloro-3-[4-(2-fluoro-phenyl)-piperidine-1-carbonyl]-indol-1-yl}-N,N-dimethyl-acetamide;
[6-Chloro-1-(2-dimethylamino-ethyl)-1H-indol-3-yl]-[4-(2-fluoro-phenyl)-piperidin-1-yl]-methanone;
2-{6-Chloro-3-[4-(2-fluoro-phenyl)-piperidine-1-carbonyl]-indol-1-yl}-1-(4-methyl-piperazin-1-yl)-ethanone;
2-{6-Chloro-3-[4-(2-fluoro-phenyl)-piperidine-1-carbonyl]-indol-1-yl}-1-piperazin-1-yl-ethanone or hydrochloride salt thereof; and
2-[6-Chloro-3-(3,4,5,6-tetrahydro-2H-[4,4']bipyridinyl-1-carbonyl)-indol-1-yl]-N,N-dimethyl-acetamide.

Also encompassed by the compounds of formula (I) are the following compounds of formula (I-c) according to the invention:

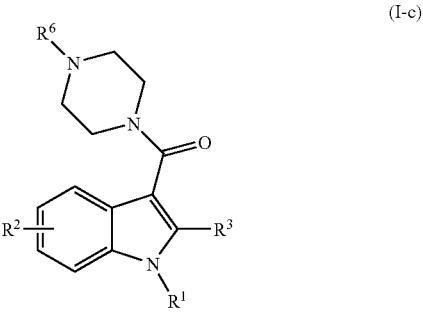

(I-c)

wherein $R^1$ to $R^3$ and $R^6$ are as defined hereinabove for formula (I).

Preferred compounds of formula (I-c) are those compounds wherein, $R^1$ is H or
or is $C_{1-6}$-alkyl substituted by $NR^iR^{ii}$,
or is $—(CH_2)_m—R^a$ wherein $R^a$ is:
$NR^iR^{ii}$,
5 to 6 membered-heterocycloalkyl, aryl, or 5 or 6 membered heteroaryl which are optionally substituted by one or more $C_{1-6}$-alkyl,
or is $—(CH_2)_n—(CO)—R^b$, wherein $R^b$ is:
$NR^iR^{ii}$,
5 to 7 membered-heterocycloalkyl which is optionally substituted by one or more $C_{1-6}$-alkyl;
$R^2$ is one or more of H, halo or $C_{1-6}$-alkyl;
$R^3$ is H or $C_{1-6}$-alkyl;
$R^6$ is aryl, 5 or 6 membered heteroaryl, or a 9 or 10-membered bicyclic heteroaryl ring which are optionally substituted by halo, $C_{1-6}$-alkyl, $C_{1-6}$-alkoxy, $C_{1-6}$-haloalkyl, CN, nitro, $NR^iR^{ii}$, $NR^{iii}R^{iv}$, $C_{1-6}$-alkoxy-$C_{1-6}$-alkylene, COOH, $S(O)_2—C_{1-6}$-alkyl, or by an oxo or dioxo bridge;
$R^i$ and $R^{ii}$ are each independently H, $C_{1-6}$-alkyl, $C_{1-6}$-alkyl-$NR^{iii}R^{iv}$, $—C(O)—C_{1-6}$-alkyl, or $—S(O)_2—C_{1-6}$-alkyl;
$R^{iii}$ and $R^{iv}$ are each independently H or $C_{1-6}$-alkyl;
m is 1 to 6; and
n is 0 to 4;
and pharmaceutically acceptable salts thereof.

It is preferred that $R^1$, $R^2$ and $R^3$ are not simultaneously H.

Examples of compounds of formula (I-c) according to the invention are:

Benzyl-2-methyl-1H-indol-3-yl)-(4-phenyl-piperazin-1-yl)-methanone;
Benzyl-2-methyl-1H-indol-3-yl)-[4-(2-methoxy-phenyl)-piperazin-1-yl]-methanone;
Benzyl-2-methyl-1H-indol-3-yl)-[4-(4-methoxy-phenyl)-piperazin-1-yl]-methanone;
Benzyl-2-methyl-1H-indol-3-yl)-[4-(2-chloro-phenyl)-piperazin-1-yl]-methanone;
Benzyl-2-methyl-1H-indol-3-yl)-[4-(4-chloro-phenyl)-piperazin-1-yl]-methanone;
(6-Chloro-1H-indol-3-yl)-(4-phenyl-piperazin-1-yl)-methanone;
(6-Chloro-1H-indol-3-yl)-[4-(2-chloro-6-nitro-phenyl)-piperazin-1-yl]-methanone;
(6-Chloro-1H-indol-3-yl)-[4-(2,6-dichloro-phenyl)-piperazin-1-yl]-methanone;
(6-Chloro-1H-indol-3-yl)-[4-(2,3-dihydro-benzo[1,4]dioxin-5-yl)-piperazin-1-yl]-methanone;

(6-Chloro-1H-indol-3-yl)-[4-(2-nitro-4-trifluoromethyl-phenyl)-piperazin-1-yl]-methanone;
(6-Chloro-1H-indol-3-yl)-[4-(2-chloro-phenyl)-piperazin-1-yl]-methanone;
[4-(2-Amino-6-chloro-phenyl)-piperazin-1-yl]-(6-chloro-1H-indol-3-yl)-methanone;
(6-Chloro-1H-indol-3-yl)-[4-(4-methoxy-phenyl)-piperazin-1-yl]-methanone;
(6-Chloro-1H-indol-3-yl)-[4-(3-methoxy-phenyl)-piperazin-1-yl]-methanone;
(6-Chloro-1H-indol-3-yl)-[4-(2-nitro-phenyl)-piperazin-1-yl]-methanone;
(6-Chloro-1H-indol-3-yl)-[4-(2-methoxy-phenyl)-piperazin-1-yl]-methanone;
(6-Chloro-1H-indol-3-yl)-[4-(4-fluoro-phenyl)-piperazin-1-yl]-methanone;
(6-Chloro-1H-indol-3-yl)-[4-(3-fluoro-phenyl)-piperazin-1-yl]-methanone;
3-Chloro-4-[4-(6-chloro-1H-indole-3-carbonyl)-piperazin-1-yl]-benzonitrile;
(6-Chloro-1H-indol-3-yl)-[4-(2-ethoxy-phenyl)-piperazin-1-yl]-methanone;
2-{6-Chloro-3-[4-(2-ethoxy-phenyl)-piperazine-1-carbonyl]-indol-1-yl}-1-(4-methyl-piperazin-1-yl)-ethanone;
2-{6-Chloro-3-[4-(2-methoxy-phenyl)-piperazine-1-carbonyl]-indol-1-yl}-N-(2-dimethylamino-ethyl)-acetamide;
2-{6-Chloro-3-[4-(2-ethoxy-phenyl)-piperazine-1-carbonyl]-indol-1-yl}-N-(2-dimethylamino-ethyl)-acetamide;
2-{6-Chloro-3-[4-(2-methoxy-phenyl)-piperazine-1-carbonyl]-indol-1-yl}-acetamide;
2-{6-Chloro-3-[4-(2-methoxy-phenyl)-piperazine-1-carbonyl]-5-methyl-indol-1-yl}-N,N-dimethyl-acetamide;
2-{6-Chloro-3-[4-(2-methoxy-phenyl)-piperazine-1-carbonyl]-indol-1-yl}-1-piperazin-1-yl-ethanone or hydrochloride salt thereof;
2-{6-Chloro-3-[4-(2-methoxy-phenyl)-piperazine-1-carbonyl]-indol-1-yl}-N-(2-methylamino-ethyl)-acetamide or hydrochloride salt thereof;
N-(2-Amino-ethyl)-2-{6-chloro-3-[4-(2-methoxy-phenyl)-piperazine-1-carbonyl]-indol-1-yl}-acetamide or hydrochloride salt thereof;
[1-(2-Amino-ethyl)-6-chloro-1H-indol-3-yl]-[4-(2-methoxy-phenyl)-piperazin-1-yl]-methanone;
[6-Chloro-1-(2-methylamino-ethyl)-1H-indol-3-yl]-[4-(2-methoxy-phenyl)-piperazin-1-yl]-methanone;
[6-Chloro-1-(2-methylamino-ethyl)-1H-indol-3-yl]-[4-(2-ethoxy-phenyl)-piperazin-1-yl]-methanone;
2-{6-Chloro-3-[4-(2-ethoxy-phenyl)-piperazine-1-carbonyl]-indol-1-yl}-N-(2-methylamino-ethyl)-acetamide;
[6-Chloro-1-(2-dimethylamino-ethyl)-1H-indol-3-yl]-[4-(2-ethoxy-phenyl)-piperazin-1-yl]-methanone;
(6-Chloro-1H-indol-3-yl)-[4-(2-fluoro-phenyl)-piperazin-1-yl]-methanone;
[1-(2-Amino-ethyl)-6-chloro-1H-indol-3-yl]-[4-(2-fluoro-phenyl)-piperazin-1-yl]-methanone;
2-{6-Chloro-3-[4-(2-fluoro-phenyl)-piperazine-1-carbonyl]-indol-1-yl}-N-(2-dimethylamino-ethyl)-acetamide;
2-{6-Chloro-3-[4-(2-fluoro-phenyl)-piperazine-1-carbonyl]-indol-1-yl}-N-(2-methylamino-ethyl)-acetamide;
N-(2-Amino-ethyl)-2-{6-chloro-3-[4-(2-fluoro-phenyl)-piperazine-1-carbonyl]-indol-1-yl}-acetamide;
2-{6-Chloro-3-[4-(2-methoxymethyl-phenyl)-piperazine-1-carbonyl]-indol-1-yl}-N-(2-dimethylamino-ethyl)-acetamide;
2-{6-Chloro-3-[4-(2-trifluoromethyl-phenyl)-piperazine-1-carbonyl]-indol-1-yl}-N-(2-dimethylamino-ethyl)-acetamide;
2-[6-Chloro-3-(4-pyridin-2-yl-piperazine-1-carbonyl)-indol-1-yl]-N-(2-dimethylamino-ethyl)-acetamide;
(6-Chloro-1H-indol-3-yl)-[4-(2,4-difluoro-phenyl)-piperazin-1-yl]-methanone;
(6-Chloro-1H-indol-3-yl)-[4-(3-methyl-pyridin-2-yl)-piperazin-1-yl]-methanone;
(6-Chloro-1H-indol-3-yl)-[4-(3,5-dichloro-pyridin-4-yl)-piperazin-1-yl]-methanone;
(6-Chloro-1H-indol-3-yl)-[4-(3-trifluoromethyl-pyridin-2-yl)-piperazin-1-yl]-methanone;
2-[4-(6-Chloro-1H-indole-3-carbonyl)-piperazin-1-yl]-nicotinonitrile;
(6-Chloro-1H-indol-3-yl)-(4-pyridin-2-yl-piperazin-1-yl)-methanone;
(6-Chloro-1H-indol-3-yl)-(4-thiazol-2-yl-piperazin-1-yl)-methanone;
2-[6-Chloro-3-(2,3,5,6-tetrahydro-[1,2']bipyrazinyl-4-carbonyl)-indol-1-yl]-N-methyl-acetamide;
2-{6-Chloro-3-[4-(3-methyl-pyridin-2-yl)-piperazine-1-carbonyl]-indol-1-yl}-N-methyl-acetamide;
2-{6-Chloro-3-[4-(3,5-dichloro-pyridin-4-yl)-piperazine-1-carbonyl]-indol-1-yl}-N-methyl-acetamide;
2-[6-Chloro-3-(4-pyridin-2-yl-piperazine-1-carbonyl)-indol-1-yl]-N-methyl-acetamide;
2-[6-Chloro-3-(4-thiazol-2-yl-piperazine-1-carbonyl)-indol-1-yl]-N-methyl-acetamide;
2-{6-Chloro-3-[4-(3-cyano-pyridin-2-yl)-piperazine-1-carbonyl]-indol-1-yl}-N-methyl-acetamide;
(6-Chloro-1-(S)-1-piperidin-3-ylmethyl-1H-indol-3-yl)-[4-(2-fluoro-phenyl)-piperazin-1-yl]-methanone;
(6-Chloro-1-(RS)-1-pyrrolidin-3-ylmethyl-1H-indol-3-yl)-[4-(2-fluoro-phenyl)-piperazin-1-yl]-methanone;
[6-Chloro-1-((S)-1-methyl-piperidin-3-ylmethyl)-1H-indol-3-yl]-[4-(2-fluoro-phenyl)-piperazin-1-yl]-methanone;
[6-Chloro-1-((RS)-1-methyl-pyrrolidin-3-ylmethyl)-1H-indol-3-yl]-[4-(2-fluoro-phenyl)-piperazin-1-yl]-methanone;
2-[6-Chloro-3-(2,3,5,6-tetrahydro-[1,2']bipyrazinyl-4-carbonyl)-indol-1-yl]-N,N-dimethyl-acetamide;
2-{6-Chloro-3-[4-(3-methyl-pyridin-2-yl)-piperazine-1-carbonyl]-indol-1-yl}-N,N-dimethyl-acetamide;
2-{6-Chloro-3-[4-(3,5-dichloro-pyridin-4-yl)-piperazine-1-carbonyl]-indol-1-yl}-N,N-dimethyl-acetamide;
2-[6-Chloro-3-(4-pyridin-2-yl-piperazine-1-carbonyl)-indol-1-yl]-N,N-dimethyl-acetamide;
2-[6-Chloro-3-(4-thiazol-2-yl-piperazine-1-carbonyl)-indol-1-yl]-N,N-dimethyl-acetamide;
2-{6-Chloro-3-[4-(3-cyano-pyridin-2-yl)-piperazine-1-carbonyl]-indol-1-yl}-N,N-dimethyl-acetamide;
2-[6-Chloro-3-(4-pyrimidin-2-yl-piperazine-1-carbonyl)-indol-1-yl]-N,N-dimethyl-acetamide;
(6-Chloro-2-methyl-1H-indol-3-yl)-[4-(2-methoxy-phenyl)-piperazin-1-yl]-methanone;
2-{6-Chloro-3-[4-(6-chloro-pyridin-2-yl)-piperazine-1-carbonyl]-indol-1-yl}-N-methyl-acetamide;
2-{6-Chloro-3-[4-(5-trifluoromethyl-pyridin-2-yl)-piperazine-1-carbonyl]-indol-1-yl}-N-methyl-acetamide;
2-[6-Chloro-3-(4-thieno[2,3-c]pyridin-7-yl-piperazine-1-carbonyl)-indol-1-yl]-N-methyl-acetamide;
2-{6-Chloro-3-[4-(3-chloro-5-trifluoromethyl-pyridin-2-yl)-piperazine-1-carbonyl]-indol-1-yl}-N-methyl-acetamide;
2-[4-(6-Chloro-1-methylcarbamoylmethyl-1H-indole-3-carbonyl)-piperazin-1-yl]-nicotinic acid;
2-{6-Chloro-3-[4-(2,4-difluoro-phenyl)-piperazine-1-carbonyl]-indol-1-yl}-N-(2-dimethylamino-ethyl)-acetamide; and 2-{6-Chloro-3-[4-(4-fluoro-2-methanesulfonyl-phenyl)-piperazine-1-carbonyl]-indol-1-yl}-N-methyl-acetamide.

Preferred examples of compounds of formula (I-c) according to the invention are:

2-{6-Chloro-3-[4-(2-methoxy-phenyl)-piperazine-1-carbonyl]-indol-1-yl}-N,N-dimethyl-acetamide;
2-{6-Chloro-3-[4-(2-ethoxy-phenyl)-piperazine-1-carbonyl]-indol-1-yl}-N,N-dimethyl-acetamide;
2-{6-Chloro-3-[4-(2-methoxy-phenyl)-piperazine-1-carbonyl]-indol-1-yl}-1-(4-piperazin-1-yl)-ethanone;
2-{6-Chloro-3-[4-(2-methoxy-phenyl)-piperazine-1-carbonyl]-indol-1-yl}-N-methyl-acetamide;
[6-Chloro-1-(2-dimethylamino-ethyl)-1H-indol-3-yl]-[4-(2-methoxy-phenyl)-piperazin-1-yl]-methanone;
[6-Chloro-1-(2-dimethylamino-ethyl)-1H-indol-3-yl]-[4-(2-fluoro-phenyl)-piperazin-1-yl]-methanone;
2-{6-Chloro-3-[4-(2-fluoro-phenyl)-piperazine-1-carbonyl]-indol-1-yl}-1-(4-methyl-piperazin-1-yl)-ethanone;
2-{6-Chloro-3-[4-(2-fluoro-phenyl)-piperazine-1-carbonyl]-indol-1-yl}-N,N-dimethyl-acetamide;
2-{6-Chloro-3-[4-(2-fluoro-phenyl)-piperazine-1-carbonyl]-indol-1-yl}-acetamide;
2-{6-Chloro-3-[4-(2-fluoro-phenyl)-piperazine-1-carbonyl]-indol-1-yl}-N-methyl-acetamide;
2-{6-Chloro-3-[4-(2-fluoro-phenyl)-piperazine-1-carbonyl]-indol-1-yl}-1-piperazin-1-yl-ethanone;
2-{6-Chloro-3-[4-(2,4-difluoro-phenyl)-piperazine-1-carbonyl]-indol-1-yl}-N-methyl-acetamide;
2-{6-Chloro-3-[4-(3-trifluoromethyl-pyridin-2-yl)-piperazine-1-carbonyl]-indol-1-yl}-N-methyl-acetamide;
[1-((S)-2-Amino-propyl)-6-chloro-1H-indol-3-yl]-[4-(2-fluoro-phenyl)-piperazin-1-yl]-methanone;
(6-Chloro-1-(S)-1-pyrrolidin-2-ylmethyl-1H-indol-3-yl)-[4-(2-fluoro-phenyl)-piperazin-1-yl]-methanone;
[6-Chloro-1-((S)-1-methyl-pyrrolidin-2-ylmethyl)-1H-indol-3-yl]-[4-(2-fluoro-phenyl)-piperazin-1-yl]-methanone;
2-{6-Chloro-3-[4-(2,4-difluoro-phenyl)-piperazine-1-carbonyl]-indol-1-yl}-N,N-dimethyl-acetamide;
2-{6-Chloro-3-[4-(3-trifluoromethyl-pyridin-2-yl)-piperazine-1-carbonyl]-indol-1-yl}-N,N-dimethyl-acetamide;
(6-Chloro-1-(R)-1-pyrrolidin-2-ylmethyl-1H-indol-3-yl)-[4-(2-fluoro-phenyl)-piperazin-1-yl]-methanone;
[6-Chloro-1-((R)-1-methyl-pyrrolidin-2-ylmethyl)-1H-indol-3-yl]-[4-(2-fluoro-phenyl)-piperazin-1-yl]-methanone;
N-(2-{6-Chloro-3-[4-(2-fluoro-phenyl)-piperazine-1-carbonyl]-indol-1-yl}-ethyl)-acetamide;
N-(2-{6-Chloro-3-[4-(2-fluoro-phenyl)-piperazine-1-carbonyl]-indol-1-yl}-ethyl)-methanesulfonamide;
N-(2-{6-Chloro-3-[4-(2-fluoro-phenyl)-piperazine-1-carbonyl]-indol-1-yl}-ethyl)-N-methyl-acetamide;
N-(2-{6-Chloro-3-[4-(2-fluoro-phenyl)-piperazine-1-carbonyl]-indol-1-yl}-ethyl)-N-methyl-methanesulfonamide;
2-[6-Chloro-3-(4-thieno[3,2-c]pyridin-4-yl-piperazine-1-carbonyl)-indol-1-yl]-N-methyl-acetamide; and
2-{6-Chloro-3-[4-(3-iodo-pyridin-2-yl)-piperazine-1-carbonyl]-indol-1-yl}-N-methyl-acetamide.

Also encompassed by the compounds of formula (I) are the following compounds of formula (I-d) according to the invention:

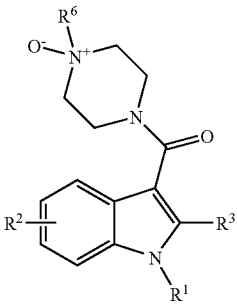

(I-d)

wherein $R^1$ to $R^3$ and $R^6$ are as defined hereinabove for formula (I).

Again, it is preferred that $R^1$, $R^2$ and $R^3$ are not simultaneously H.

Preferred compounds of formula (I-d) are those compounds wherein the substitution pattern is analogous to that of the preferred compounds of formula (I-c), and further preferred are those compounds wherein $R^1$ is H;
$R^2$ is one or more halo;
$R^3$ is H;
$R^6$ is aryl substituted by $C_{1-6}$-alkoxy,
and pharmaceutically acceptable salts thereof.

As an example, (6-chloro-1H-indol-3-yl)-[4-(2-methoxy-phenyl)-4-oxy-piperazin-1-yl]-methanone is mentioned.

The combinations of the substitution patterns provided herein for compounds of formula (I), (I-a), (I-a'), (I-b), (I-c) and (I-d) for each of the embodiments provided are also encompassed by the invention.

The invention also encompasses methods for the treatment of dysmenorrhea, hypertension, chronic heart failure, inappropriate secretion of vasopressin, liver cirrhosis, nephrotic syndrome, obsessive compulsive disorder, anxiety or depressive disorders which comprise administering a compound of formulae (I), (I-a), (I-a'), (I-b), (I-c) or (I-d).

The invention also encompasses a pharmaceutical composition comprising a therapeutically effective amount of a compound of formula (I), (I-a), (I-a'), (I-b), (I-c) or (I-d) and a pharmaceutically acceptable carrier. Such pharmaceutical compositions are useful for treating dysmenorrhea, hypertension, chronic heart failure, inappropriate secretion of vasopressin, liver cirrhosis, nephrotic syndrome, obsessive compulsive disorder, anxiety and depressive disorders.

In a certain embodiment, the compounds of formula (I) of the invention can be manufactured according to a process comprising reacting a compound of formula (II):

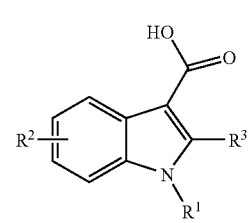

II with a compound of formula A-H, to obtain a compound of formula (I) wherein A, $R^1$, $R^2$ and $R^3$ are as defined hereinabove for formula (I).

In another embodiment, the compounds of formula (I) of the invention can be manufactured according to a process comprising reacting a compound of formula (I-1), wherein $R^1$ is H:

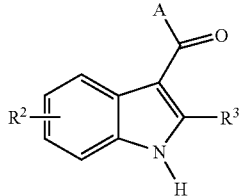

with a compound of formula $R^1$—X, to obtain a compound of formula (I) wherein A, $R^1$, $R^2$ and $R^3$ are as defined hereinabove for formula (I) and X is halo.

In another embodiment, the compounds of formula (I) of the invention can be manufactured according to a process comprising hydrolyzing a compound of formula (V):

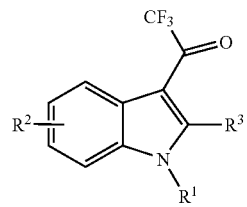

to obtain a compound of formula (II):

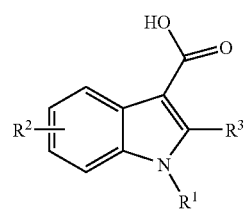

and then reacting the compound of formula (II) with a compound of formula A-H, to obtain a compound of formula (I) wherein $R^1$, $R^2$ and $R^3$ are as defined hereinabove for formula (I).

These processes are described more in details with the following general schemes and procedures A to C.

General scheme A

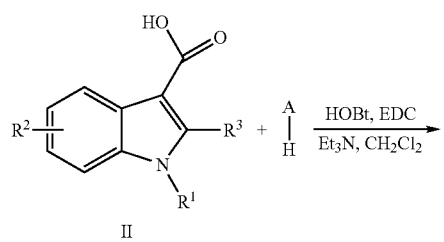

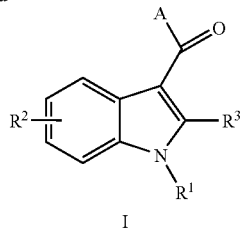

General Scheme A

Compounds of formula (I) can be prepared via an amide coupling between an indole 3-carboxylic acid (II) and a compound of formula (A-H), wherein A is defined as hereinabove. The usual reagents and protocols known in the art can be used to effect the amide coupling. Indole 3-carboxylic acids (II) are either commercially available or readily prepared using a procedure described in *J. Med. Chem.* 1991, 34, 140. Alternatively, they can be prepared following the general scheme C as described hereinafter. The compounds of formula (A-H) are either commercially available or prepared using methods known in the art starting from commercially available materials. General scheme A is hereinafter further illustrated with general procedure I.

General scheme B

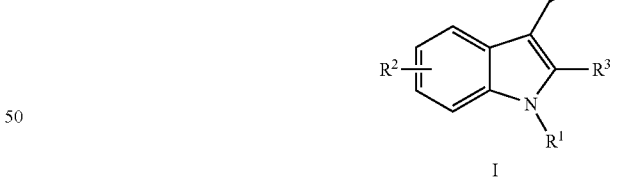

General Procedure B

Compounds of formula (I) with $R^1$ different from H can be prepared using methods known in the art, e.g. by N-deprotonation of a compound of formula (I-1) (compounds of formula (I) wherein $R^1$ is H) followed by treatment with an electrophilic reactant $R^1$—X (wherein X is a leaving group, e.g. halo) which is either commercially available or easily prepared according to methods well known in the art and commercially available starting materials. General scheme B is hereinafter further illustrated with general procedure II.

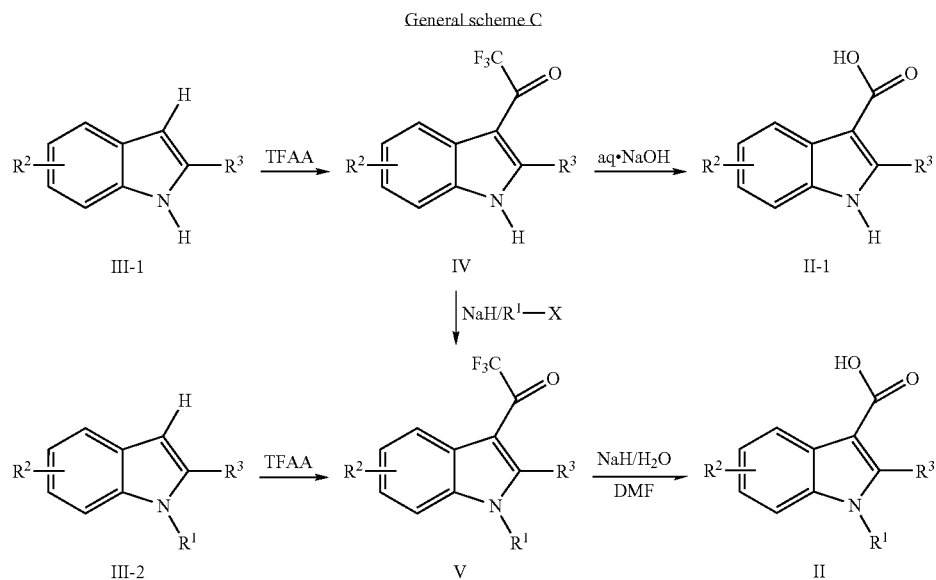

General scheme C

General Procedure C

The treatment of an indole derivative (III-1) with trifluoroacetic anhydride in DMF affords intermediate (IV) which can be hydrolyzed with an aqueous sodium hydroxide solution to give the 3-carboxylic acid indole derivative (II-1). Alternatively, (IV) could react with an electrophilic reactant $R^1$—X to give (V), which is then converted to the corresponding carboxylic acid derivative (II) with $NaH/H_2O$ in DMF (see *J. Org. Chem.*, 1993, 10, 2862). Intermediate (V) can alternatively be obtained by treatment of an indole derivative (III-2) with trifluoroacetic anhydride in a suitable solvent, e.g. DMF, dichloromethane or 1,2-dichloroethane. Addition of a suitable base may be advantageous.

V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM MgCl2 adjusted to pH=7.4+ complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43,000 g at 4° C. (19'000 rpm). The pellet is resuspended in 12.5 ml Lysis buffer+12.5 ml Sucrose 20% and homogenized using a Polytron for 1-2 min. The protein concentration is determined by the Bradford method, and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM KCl, 2 mM $CaCl_2$, 10 mM $MgCl_2$) for 15 minutes with mixing. 50 ul of bead/membrane mixture is then added to each well of a 96 well plate, followed by 50 ul of 4 nM 3H-Vasopressin (American Radiolabeled Chemicals). For total binding measurement 100 ul of binding buffer are added to the respective wells, for non-specific binding 100 ul of 8.4 mM cold vasopressin and for compound testing 100 ul of a serial dilution of each compound in 2% DMSO. The plate is incubated 1 h at room temperature, centrifuged 1 min at 1000 g and counted on a Packard Top-Count. Non-specific binding counts are subtracted from each well, and data is normalized to the maximum specific binding set at 100%. To calculate an IC 50 the curve is fitted using a non-linear regression model (XLfit) and the Ki is calculated using the Cheng-Prussoff equation.

| Ex. No. | Ki (nM) |
|---------|---------|
| 3       | 14      |
| 24      | 10      |
| 40      | 8       |
| 43      | 2       |
| 44      | 3       |
| 45      | 7       |
| 46      | 7       |
| 47      | 4       |
| 48      | 7       |
| 49      | 3       |
| 50      | 4       |
| 51      | 0       |
| 52      | 4       |
| 55      | 2       |
| 56      | 2       |
| 57      | 2       |
| 58      | 9       |
| 59      | 2       |
| 60      | 8       |
| 61      | 13      |
| 62      | 11      |
| 63      | 2       |
| 66      | 4       |
| 67      | 5       |
| 69      | 6       |

| Ex. No. | Ki (nM) |
|---|---|
| 71 | 5 |
| 72 | 3 |
| 76 | 8 |
| 80 | 6 |
| 81 | 13 |
| 82 | 2 |
| 84 | 11 |
| 87 | 4 |
| 88 | 7 |
| 90 | 8 |
| 95 | 13 |
| 96 | 11 |
| 97 | 6 |
| 102 | 7 |
| 106 | 5 |
| 107 | 12 |
| 108 | 8 |
| 111 | 7 |
| 114 | 3 |
| 115 | 11 |
| 117 | 6 |
| 118 | 12 |
| 122 | 10 |
| 151 | 14 |
| 152 | 14 |
| 153 | 23 |
| 162 | 27 |
| 163 | 22 |
| 171 | 7 |
| 172 | 10 |
| 174 | 3 |
| 175 | 32 |
| 176 | 8 |
| 177 | 8 |
| 190 | 19 |
| 196 | 26 |
| 198 | 20 |
| 200 | 21 |
| 203 | 2 |
| 205 | 10 |
| 211 | 13 |
| 214 | 16 |
| 215 | 6 |
| 217 | 21 |
| 218 | 16 |
| 219 | 15 |
| 220 | 17 |
| 224 | 27 |
| 225 | 12 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic excipients for the production of tablets, coated tablets, dragées, and hard gelatin capsules. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

Compounds of formula (I) have good activity on the V1a receptor. The invention provides methods for treating dysmenorrhea, hypertension, chronic heart failure, inappropriate secretion of vasopressin, liver cirrhosis, nephrotic syndrome, obsessive compulsive disorder, anxiety and depressive disorders by administering a compound of formula (I) or a pharmaceutically acceptable salt thereof. The preferred indications with regard to the present invention are the treatment of anxiety and depressive disorders.

The compounds and compositions of the invention can be administered in a conventional manner, for example, orally rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injectable solutions.

The dosage at which a compound of the invention can be administered can vary within wide limits and will, of course, be fitted to the individual requirements in each particular case. In general, in the case of oral administration a daily dosage of about 10 to 1000 mg per person of a compound of general formula (I), (I-a), (I-b); (I-c) or (I-d) should be appropriate, although the above upper limit can also be exceeded when necessary.

The following Examples illustrate the present invention without limiting it. All temperatures are given in degrees Celsius.

Example A

Tablets of the following composition are manufactured in the usual manner:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C.

Thereupon, the finely powdered active substance is added thereto and stirred until it has dispersed completely. The mixture is poured into suppository moulds of suitable size, left to cool; the suppositories are then removed from the moulds and packed individually in wax paper or metal foil.

Where journal references are cited in the examples, the example was performed using the starting material listed with the reactants and conditions cited in the reference. All procedures in such references are well known to those of ordinary skill in the art. All journal references cited herein are incorporated by reference.

EXAMPLES

General Procedure I: Amide Coupling

To a stirred solution of an indole-3-carboxylic acid derivative (1 mmol) in 10 ml $CH_2Cl_2$ were added (1.3 mmol) EDC, (1.3 mmol) HOBt, (1.3 mmol) $Et_3N$ and (1 mmol) of the amine derivative. The mixture was stirred overnight at RT and then poured onto water and extracted with $CH_2Cl_2$. The combined organic phases were dried over $Na_2SO_4$ and concentrated in vacuo. Flash chromatography or preparative HPLC afforded the title compound.

General Procedure II: Alkylation

To a stirred solution of (6-chloro-1H-indol-3-yl)-(4-phenyl-piperidin-1-yl)-methanone in DMF were added 2.1 eq. NaH (60% in oil). The mixture was stirred at RT for 30 min. and then the electrophilic reagent $R^1$—X (1.1 eq.) was added. The mixture was stirred an additional 14 hours at 60° C. and then poured onto water and extracted with ethyl acetate. The combined organic phases were dried over $Na_2SO_4$ and concentrated in vacuo. Purification by preparative HPLC afforded the corresponding derivatives.

Acid Intermediates of Formula II and II-1

Acid 1

6-Chloro-1H-indole-3-carboxylic acid

Using a procedure described in *J. Med. Chem.* 1991, 34, 140, from 7.0 g (0.046 mmol) of 6-chloro-1H-indole were prepared 5.80 g (64%) of 6-chloro-1H-indole-3-carboxylic acid as a light brown solid.

ES-MS m/e (%): 194 (M–$H^+$).

Acid 2

6-Chloro-1-dimethylcarbamoylmethyl-1H-indole-3-carboxylic acid 1-(6-Chloro-1H-indol-3-yl)-2,2,2-trifluoro-ethanone Using a procedure described in *J. Med. Chem.* 1991, 34, 140, from 0.50 g (0.004 mol) of 6-chloro-1H-indole were prepared 0.76 g (95%) of 1-(6-chloro-1H-indol-3-yl)-2,2,2-trifluoro-ethanone as a white solid.

2-[6-Chloro-3-(2,2,2-trifluoro-acetyl)-indol-1-yl]-N,N-dimethyl-acetamide

To a stirred solution of 1-(6-chloro-1H-indol-3-yl)-2,2,2-trifluoro-ethanone (0.75 g) in 20 ml of DMF at 0° C., were added 128 mg (1.1 eq.) of NaH (60% in oil). The mixture was stirred for 30 min. and then 0.32 ml (1.1 eq.) of dimethylamino-acetyl chloride were added. The mixture was stirred an additional hour and then poured onto water and extracted with ethyl acetate. The combined organic phases were dried over $Na_2SO_4$ and concentrated in vacuo to afford 598 mg (61%) of 2-[6-chloro-3-(2,2,2-trifluoro-acetyl)-indol-1-yl]-N,N-dimethyl-acetamide as a white solid.

6-Chloro-1-dimethylcarbamoylmethyl-1H-indole-3-carboxylic acid

Using a procedure similar to that described in *J. Med. Chem.* 1991, 34, 140, from 0.50 g of 2-[6-chloro-5-methyl-3-(2,2,2-trifluoro-acetyl)-indol-1-yl]-N,N-dimethyl-acetamide were prepared 0.38 g (76%) of 6-chloro-1-dimethylcarbamoylmethyl-1H-indole-3-carboxylic acid as a white solid Acid 3

6-Chloro-1-methylcarbamoylmethyl-1H-indole-3-carboxylic acid

2-[6-Chloro-3-(2,2,2-trifluoro-acetyl)-indol-1-yl]-N-methyl-acetamide

Following general procedure II, the alkylation of 1-(6-chloro-1H-indol-3-yl)-2,2,2-trifluoro-ethanone, with (commercially available) 2-chloro-N-methyl-acetamide gave the title compound.

ES-MS m/e (%): 319.3 (M+$H^+$).

6-Chloro-1-methylcarbamoylmethyl-1H-indole-3-carboxylic acid

2-[6-Chloro-3-(2,2,2-trifluoro-acetyl)-indol-1-yl]-N-methyl-acetamide was suspensed in DCE and treated with (2.2 eq.) of sodium trimethylsilanolate. After shaking at room temperature for 20 min, the mixture was concentrated in vacuo and purified by prep. HPLC to give the title compound in 27% yield.

ES-MS m/e (%): 265.0 (M−H$^+$).

Acid 4

6-Chloro-1-[(2-dimethylamino-ethylcarbamoyl)-methyl]-1H-indole-3-carboxylic acid

[6-Chloro-3-(2,2,2-trifluoro-acetyl)-indol-1-yl]-acetic acid methyl ester

To a stirred solution of 6.65 g (0.0265 mol, 1 eq.) of 1-(6-chloro-1H-indol-3-yl)-2,2,2-trifluoro-ethanone in 25 ml of DMF at 0° C. were added 1.23 g of NaH (55% in oil, 0.0282 mol, 1.05 eq). After 30 minutes, 4.31 g (0.0282 mol, 1.05 eq.) of bromo-acetic acid methyl ester were added and the temperature raised to RT, and stirring was continued overnight. The reaction was quenched by the addition of aq.HCl 0.1 M, and the product was extracted with EtOAc and the combined organic phases dried over Na$_2$SO$_4$. Recrystallisation in Et$_2$O/Heptane afforded 6.90 g (80%) of [6-chloro-3-(2,2,2-trifluoro-acetyl)-indol-1-yl]-acetic acid methyl ester as white crystals.

[6-Chloro-3-(2,2,2-trifluoro-acetyl)-indol-1-yl]-acetic acid

To as stirred solution of 2 g (6.3 mmol) of [6-chloro-3-(2,2,2-trifluoro-acetyl)-indol-1-yl]-acetic acid methyl ester in 45 ml of THF/MeOH/H$_2$O 1/1/1, at 40° C., were added 0.79 g (18.9 mmol, 3 eq.) of LiOH.H$_2$O. After 1 hour, the reaction mixture was diluted in EtOAc, acidified with aq.HCl 1M. The organic phase were dried over Na$_2$SO$_4$, and concentrated under vacuo to afford 1.9 g (99%) of [6-chloro-3-(2,2,2-trifluoro-acetyl)-indol-1-yl]-acetic acid as a white solid.

2-[6-Chloro-3-(2,2,2-trifluoro-acetyl)-indol-1-yl]-N-(2-dimethylamino-ethyl)-acetamide An amide coupling between 0.99 g of [6-Chloro-3-(2,2,2-trifluoro-acetyl)-indol-1-yl]-acetic and N1,N1-dimethyl-ethane-1,2-diamine according to the general procedure I, afforded 78 mg (6%) of 2-[6-chloro-3-(2,2,2-trifluoro-acetyl)-indol-1-yl]-N-(2-dimethylamino-ethyl)-acetamide as a white solid.

6-Chloro-1-[(2-dimethylamino-ethylcarbamoyl)-methyl]-1H-indole-3-carboxylic acid Using a similar procedure described in *J. Med. Chem.* 1991, 34, 140, from 78 mg of of 2-[6-chloro-3-(2,2,2-trifluoro-acetyl)-indol-1-yl]-N-(2-dimethylamino-ethyl)-acetamide were prepared 65 mg (96%) of 6-chloro-1-[(2-dimethylamino-ethylcarbamoyl)-methyl]-1H-indole-3-carboxylic acid as a white solid.

Acid 5

6-Chloro-1-dimethylcarbamoylmethyl-5-methyl-1H-indole-3-carboxylic acid

1-(6-Chloro-5methyl-1H-indol-3-yl)-2,2,2-trifluoro-ethanone

Using a procedure described in *J. Med. Chem.* 1991, 34, 140, from 0.250 g (0.002 mol) of 6-chloro-5-methyl-1H-indole were prepared 0.38 g (96%) of 1-(6-chloro-5methyl-1H-indol-3-yl)-2,2,2-trifluoro-ethanone as a white solid.

2-[6-Chloro-5-methyl-3-(2,2,2-trifluoro-acetyl)-indol-1-yl]-N,N-dimethyl-acetamide To a stirred solution of 1-(6-chloro-5methyl-1H-indol-3-yl)-2,2,2-trifluoro-ethanone (0.38 g) in 10 ml of DMF at 0° C., were added 64 mg (1.1 eq.) of NaH (60% in oil). The mixture was stirred for 30 min. and then 0.16 ml (1.1 eq.) of dimethylamino-acetyl chloride were added. The mixture was stirred an additional hour and then poured onto water and extracted with ethyl acetate. The combined organic phases were dried over Na$_2$SO$_4$ and concentrated in vacuo to afford 300 mg (60%) of 2-[6-chloro-5-methyl-3-(2,2,2-trifluoro-acetyl)-indol-1-yl]-N,N-dimethyl-acetamide as a white solid.

6-Chloro-1-dimethylcarbamoylmethyl-5-methyl-1H-indole-3-carboxylic acid

Using a similar procedure described in *J. Med. Chem.* 1991, 34, 140, from 0.280 g of 2-[6-chloro-5-methyl-3-(2,2,2-trifluoro-acetyl)-indol-1-yl]-N,N-dimethyl-acetamide were prepared 0.18 g (76%) of 6-chloro-1-dimethylcarbamoylmethyl-5-methyl-1H-indole-3-carboxylic acid as a white solid

Acid 6

5,6-Dichloro-1-dimethylcarbamoylmethyl-1H-indole-3-carboxylic acid

1-(5,6-Dichloro-1H-indol-3-yl)-2,2,2-trifluoro-ethanone

Using a procedure described in *J. Med. Chem.* 1991, 34, 140, from 0.120 g (0.64 mmol) of 5,6-dichloro-1H-indole were prepared 0.11 g (59%) of 1-(5,6-dichloro-1H-indol-3-yl)-2,2,2-trifluoro-ethanone as a white solid.

2-[5,6-Dichloro-3-(2,2,2-trifluoro-acetyl)-indol-1-yl]-N,N-dimethyl-acetamide To a stirred solution of 1-(5,6-dichloro-1H-indol-3-yl)-2,2,2-trifluoro-ethanone (0.11 g) in 3 ml of DMF at 0° C., were added 18 mg (1.05 eq.) of NaH (60% in oil). The mixture was stirred for 30 min. and then 0.04 ml (1.0 eq.) of dimethylamino-acetyl chloride were added. The mixture was stirred an additional hour and then poured onto water and extracted with ethyl acetate. The combined organic phases were dried over $Na_2SO_4$ and concentrated in vacuo to afford 112 mg (78%) of 2-[5,6-dichloro-3-(2,2,2-trifluoro-acetyl)-indol-1-yl]-N,N-dimethyl-acetamide as a white solid.

5,6-Dichloro-1-dimethylcarbamoylmethyl-1H-indole-3-carboxylic acid

Using a similar procedure described in *J. Med. Chem.* 1991, 34, 140, from 0.112 g of 2-[5,6-dichloro-3-(2,2,2-trifluoro-acetyl)-indol-1-yl]-N,N-dimethyl-acetamide were prepared 0.047 g (49%) of 5,6-dichloro-1-dimethylcarbamoyl-methyl-1H-indole-3-carboxylic acid as a white solid.

Acid 7

6-Chloro-2-methyl-1H-indole-3-carboxylic acid (6-Chloro-1H-indol-2-yl)-methanol

To a solution of 2.00 g (8.94 mmol) 6-chlorindole-2-carboxylic acid ethyl ester in 50 ml diethyl ether were added 0.475 g (12.5 mmol) lithium aluminum hydride at 0° C. The reaction mixture was heated at reflux for 45 min and quenched by consecutive addition of 10 ml water, 10 ml aqueous 2 M sodium hydroxide solution and 10 ml water at 0° C. The aqueous layer was extracted with tert-butyl methyl ether (3×100 ml). The combined organic layers were dried over sodium sulfate and concentrated in vacuo to give the crude title compound (1.64 g; 100%) as a white solid.
MS m/e (%): 180 (M–$H^+$, 100).

6-Chloro-2-methyl-1H-indole

A solution of 1.60 g (8.81 mmol) (6-chloro-1H-indol-2-yl)-methanol in 5 ml 1,2-dichloroethane was added to a mixture of 80.0 ml trifluoroacetic acid and 32.0 ml triethylsilane at 65° C. After 5 min, the reaction mixture was cooled to room temperature and quenched with water. The pH was adjusted to 14 by the addition of aqueous sodium hydroxide solution (32%). The aqueous layer was extracted with tert-butyl methyl ether (3×200 ml). The combined organic layers were dried over sodium sulfate and concentrated in vacuo. The residue was purified by flash-chromatography (aminopropyl-modified silica gel, n-heptane/ethyl acetate) to give the title compound (0.39 g; 27%) as a white solid.
MS m/e (%): 164 (M–$H^+$, 100).

1-(6-Chloro-2-methyl-1H-indol-3-yl)-2,2,2-trifluoro-ethanone

To a solution of 0.38 g (2.3 mmol) 6-chloro-2-methyl-1H-indole in 20 ml 1,2-dichloroethane at 0° C. were added 0.35 ml (2.5 mmol) trifluoroacetic anhydride. The reaction mixture was quenched with aqueous 2 M sodium carbonate solution after 30 min and extracted with dichloromethane (3×100 ml). The combined organic layers were dried over sodium sulfate and concentrated in vacuo to give the title compound (0.57 g; 95%) as an off-white solid.
MS m/e (%): 260 (M–$H^+$, 100).

6-Chloro-2-methyl-1H-indole-3-carboxylic acid

A solution of 0.57 g (2.2 mmol) 1-(6-chloro-2-methyl-1H-indol-3-yl)-2,2,2-trifluoro-ethanone in 21.7 ml (86.8 mmol) aqueous 4 M sodium hydroxide solution was heated at reflux for 45 min. After cooling to room temperature the reaction mixture was diluted with water and extracted with tert-butyl methyl ether (2×50 ml). The aqueous layer was cooled to 0-5° C., acidified (pH 1-2) with concentrated aqueous hydrochloric acid solution and extracted with ethyl acetate (3×100 ml). The combined ethyl acetate layers were dried over sodium sulfate and concentrated in vacuo to give the title compound (0.14 g, 31%) as an off-white solid.
MS m/e (%): 208 (M–$H^+$, 100).

Acid 8

5-Chloro-2-methyl-1H-indole-3-carboxylic acid

Using a procedure described in *J. Med. Chem.* 1991, 34, 140, from the 5-chloro-2-methyl-1H-indole was prepared 5-chloro-2-methyl-1H-indole-3-carboxylic acid.

Acid 9

Benzyl-2-methyl-1H-indole-3-carboxylic acid

To a stirred solution of 0.50 g (3.1 mmol) 2-methyl-1H-indole-3-carboxylic acid (described in *J. Heterocyclic Chem.* 1977, 14, 1123) in 5 ml DMF were added 0.27 g (6.75 mmol) of NaH (60% in oil). The mixture was stirred at RT for 30 min. and then 0.39 ml (3.28 mmol) of benzyl bromid were added. The mixture was stirred an additional hour and then poured onto water and extracted with ethyl acetate. The combined organic phases were dried over $Na_2SO_4$ and concentrated in vacuo. Crystallization in $Et_2O$ afforded 0.61 g (78%) of 1-benzyl-2-methyl-1H-indole-3-carboxylic acid as a white solid.

Acid 10

3,4-Dihydro-1H-pyrazino[1,2-a]indole-2,10-dicarboxylic acid 2-tert-butyl ester 10-(2,2,2-Trifluoro-acetyl)-3,4-dihydro-1H-pyrazino[1,2-a]indole-2-carboxylic acid tert-butyl ester To a stirred solution of 0.21 ml (1.5 mmol) trifluoroacetic anhydride in 7 ml 1,2-dichloroethane was added at 0° C. a solution of 0.37 g (1.4 mmol) 3,4-dihydro-1H-pyrazino[1,2-a]indole-2-carboxylic acid tert-butyl ester and a solution of 0.23 ml (1.63 mmol) triethylamine in 3 ml 1,2-dichloroethane. After stirring for 30 min the reaction mixture was quenched with saturated aqueous sodium hydrogen carbonate solution and extracted with dichloromethane (2×100 ml). The combined organic layers were dried over sodium sulfate, concentrated in vacuo and purified by flash chromatography (n-heptane/ethyl acetate) to give the title compound (0.288 g, 58%) as a light yellow solid.
MS m/e (%): 369 (M+$H^+$, 27).

3,4-Dihydro-1H-pyrazino[1,2-a]indole-2,10-dicarboxylic acid 2-tert-butyl ester

To a solution of 0.29 g (0.77 mmol) 10-(2,2,2-trifluoro-acetyl)-3,4-dihydro-1H-pyrazino[1,2-a]indole-2-carboxylic acid tert-butyl ester in 7 ml N,N-dimethylformamide were subsequently added 0.22 g (4.6 mmol) sodium hydride (50% in oil) and a solution of 0.070 ml (3.9 mmol) water in 1 ml N,N-dimethylformamide at room temperature. The reaction mixture was diluted with tert-butyl methyl ether after 2 h and extracted with 1 M sodium hydroxide solution (2×30 ml). The combined aqueous layers were acidified (pH 1-2) with 2 M hydrochloric acid at 0° C. and extracted with tert-butyl methyl ether (3×50 ml). The combined organic layers were dried over sodium sulfate and concentrated in vacuo to give the title compound (0.21 g, 86%) as a light brown solid.

MS m/e (%): 315 (M–H$^+$, 100).

Examples of Compounds of Formula I-a and I-a'

Example 1

Benzyl-2-methyl-1H-indol-3-yl)-[4-(4-fluoro-phenyl)-3,6-dihydro-2H-pyridin-1-yl]-methanone

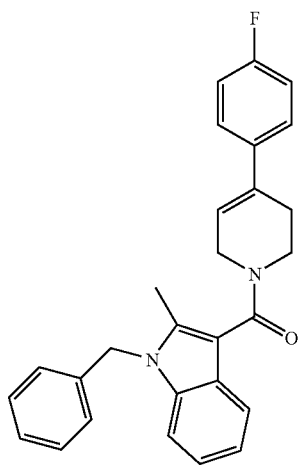

Amide coupling according to general procedure I:
Amine: 4-(4-Fluoro-phenyl)-1,2,3,6-tetrahydro-pyridine (commercially available),
Acid: 1-Benzyl-2-methyl-1H-indole-3-carboxylic acid,
ES-MS m/e (%): 425.5 (M+H$^+$).

Example 2

Benzyl-2-methyl-1H-indol-3-yl)-(4-phenyl-3,6-dihydro-2H-pyridin-1-yl)-methanone

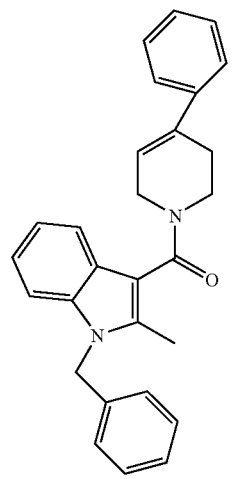

Amide coupling according to general procedure I:
Amine: 4-Phenyl-1,2,3,6-tetrahydro-pyridine (commercially available),
Acid: 1-Benzyl-2-methyl-1H-indole-3-carboxylic acid,
ES-MS m/e (%): 407.5 (M+H$^+$).

Example 3

Benzyl-2-methyl-1H-indol-3-yl)-[4-(2-methoxy-phenyl)-3,6-dihydro-2H-pyridin-1-yl]-methanone

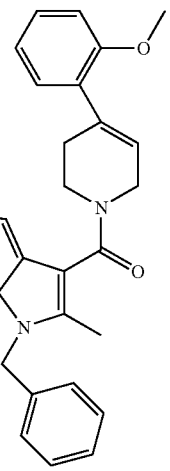

Amide coupling according to general procedure I:
Amine: 4-(2-Methoxy-phenyl)-1,2,3,6-tetrahydro-pyridine (described in U.S. Pat. No. 6,326,381),
Acid: 1-Benzyl-2-methyl-1H-indole-3-carboxylic acid,
ES-MS m/e (%): 437.6 (M+H$^+$).

Example 4

(6-Chloro-1H-indol-3-yl)-(4-phenyl-3,6-dihydro-2H-pyridin-1-yl)-methanone

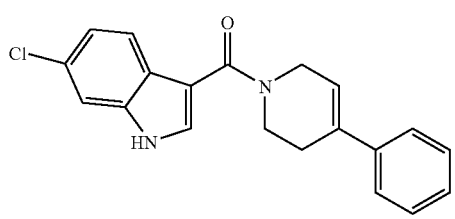

Amide coupling according to general procedure I:
Amine: 4-Phenyl-1,2,3,6-tetrahydro-pyridine (commercially available),
Acid: 6-chloro-1H-indole-3-carboxylic acid,
ES-MS m/e (%): 337.4 (M+H$^+$).

Example 5

(6-Chloro-1H-indol-3-yl)-[4-(4-fluoro-phenyl)-3,6-dihydro-2H-pyridin-1-yl]-methanone

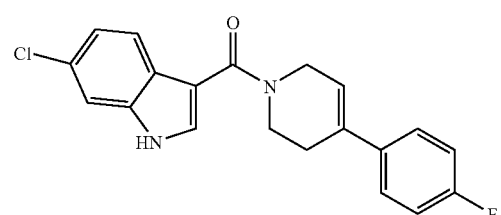

Amide coupling according to general procedure I:
Amine: 4-(4-Fluoro-phenyl)-1,2,3,6-tetrahydro-pyridine (commercially available),
Acid: 6-chloro-1H-indole-3-carboxylic acid,
ES-MS m/e (%): 355.4 (M+H⁺).

Example 6

(6-Chloro-1H-indol-3-yl)-(4-phenyl-3,6-dihydro-2H-pyridin-1-yl)-methanone

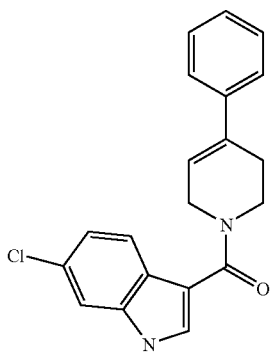

Following general procedure I, the coupling of (commercially available) 4-phenyl-1,2,3,6-tetrahydro-pyridine, with 6-chloro-1H-indole-3-carboxylic acid gave the title compound.
ES-MS m/e (%): 337.4 (M+H⁺).

Example 7

(6-Chloro-1H-indol-3-yl)-[4-(4-fluoro-phenyl)-3,6-dihydro-2H-pyridin-1-yl]-methanone

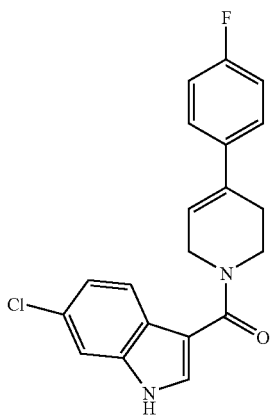

Following general procedure I, the coupling of (commercially available) 4-(4-fluoro-phenyl)-1,2,3,6-tetrahydro-pyridine with 6-chloro-1H-indole-3-carboxylic acid gave the title compound.
ES-MS m/e (%): 355.4 (M+H⁺).

Example 8

(6-Chloro-1H-indol-3-yl)-[4-(4-chloro-phenyl)-3,6-dihydro-2H-pyridin-1-yl]-methanone

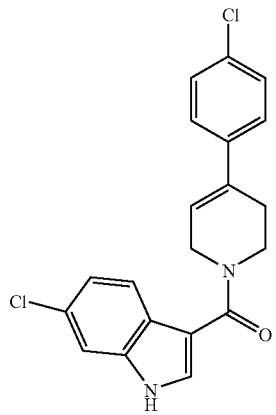

Following general procedure I, the coupling of (commercially available) 4-(4-chloro-phenyl)-1,2,3,6-tetrahydro-pyridine with 6-chloro-1H-indole-3-carboxylic acid gave the title compound.
ES-MS m/e (%): 371.4 (M+H⁺).

Example 9

Benzyl-2-methyl-1H-indol-3-yl)-(5-methyl-4-phenyl-3,6-dihydro-2H-pyridin-1-yl)-methanone

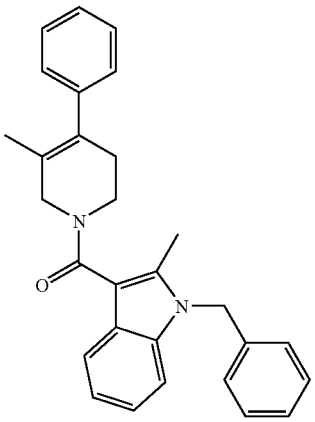

Following general procedure I, the coupling of (commercially available) 5-methyl-4-phenyl-1,2,3,6-tetrahydro-pyridine (described in WO 2005077912) with 1-benzyl-2-methyl-1H-indole-3-carboxylic acid gave the tide compound.
ES-MS m/e (%): 421.6 (M+H⁺).

Examples of Compounds of Formula I-b

Example 10

(4-Benzyl-4-hydroxy-piperidin-1-yl)-(1-benzyl-2-methyl-1H-indol-3-yl)-methanone

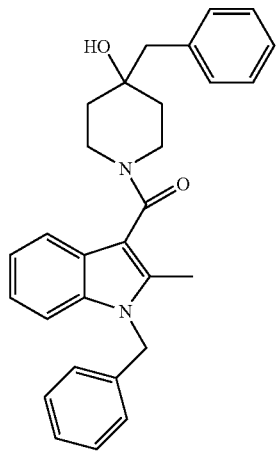

Amide coupling according to general procedure I:
Amine: 4-Benzyl-piperidin-4-ol (commercially available),
Acid: 1-Benzyl-2-methyl-1H-indole-3-carboxylic acid,
ES-MS m/e (%): 439.5 (M+H$^+$).

Example 11

(4-Benzyl-4-hydroxy-piperidin-1-yl)-[1-(2-chloro-benzyl)-2-methyl-1H-indol-3-yl]-methanone

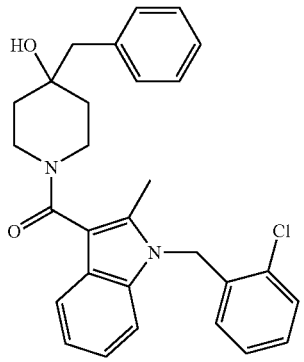

(4-Benzyl-4-hydroxy-piperidin-1-yl)-(2-methyl-1H-indol-3-yl)-methanone

To a stirred solution of 0.1 g (0.57 mmol) 2-methyl-1H-indole-3-carboxylic acid in 10 ml CH$_2$Cl$_2$ were added 0.14 g (0.73 mmol) EDC, 0.10 g (0.73 mmol) HOBt, 90 μl (0.63 mmol) Et$_3$N and 0.11 g (0.57 mmol) 4-benzyl-piperidin-4-ol. The mixture was stirred overnight at RT and then poured onto water and extracted with CH$_2$Cl$_2$. The combined organic phases were dried over Na$_2$SO$_4$ and concentrated in vacuo. Flash chromatography (ethyl acetate) afforded 0.15 g (75%) of (4-benzyl-4-hydroxy-piperidin-1-yl)-(2-methyl-1H-indol-3-yl)-methanone as a white solid.
ES-MS m/e (%): 349 (M+H$^+$).

(4-Benzyl-4-hydroxy-piperidin-1-yl)-[1-(2-chlorobenzyl)-2-methyl-1H-indol-3-yl]-methanone To a stirred solution of 40 mg (0.11 mmol) of (4-benzyl-4-hydroxy-piperidin-1-yl)-(2-methyl-1H-indol-3-yl)-methanone in 5 ml DMF were added 5 mg (0.11 mmol) NaH (60% in oil). The mixture was stirred at RT for 30 min. and then 28 mg (0.13 mmol) of 1-bromomethyl-2-chloro-benzene were added. The mixture was stirred an additional hour and then poured onto water and extracted with ethyl acetate. The combined organic phases were dried over Na$_2$SO$_4$ and concentrated in vacuo. Preparative HPLC (30% CH$_3$CN/H$_2$O) afforded 33 mg (61%) of (4-benzyl-4-hydroxy-piperidin-1-yl)-[1-(2-chloro-benzyl)-2-methyl-1H-indol-3-yl]-methanone as a white solid.
ES-MS m/e (%): 473.4 (M+H$^+$).

Example 12

Benzyl-5-chloro-2-methyl-1H-indol-3-yl)-(4-benzyl-4-hydroxy-piperidin-1-yl)-methanone

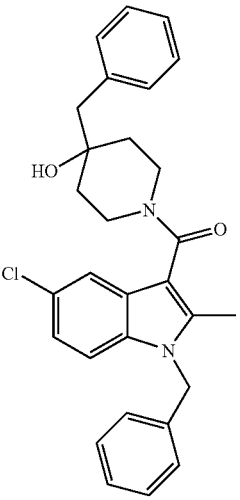

(4-benzyl-4-hydroxy-piperidin-1-yl)-(5-chloro-2-methyl-1H-indol-3-yl)-methanone

Using the procedure described for the preparation of (4-benzyl-4-hydroxy-piperidin-1-yl)-(2-methyl-1H-indol-3-yl)-methanone, from 40 mg (0.19 mmol) of 5-chloro-2-methyl-1H-indole-3-carboxylic acid and 40 mg (0.21 mmol) of 4-benzyl-piperidin-4-ol were prepared 45 mg (62%) of (4-benzyl-4-hydroxy-piperidin-1-yl)-(5-chloro-2-methyl-1H-indol-3-yl)-methanone as a white solid.
ES-MS m/e (%): 383 (M+H$^+$).

(1-benzyl-5-chloro-2-methyl-1H-indol-3-yl)-(4-benzyl-4-hydroxy-piperidin-1-yl)-methanone Using the procedure described for the preparation of (4-benzyl-4-hydroxy-piperidin-1-yl)-[1-(2-chloro-benzyl)-2-methyl-1H-indol-3-yl]-methanone, from 13 mg (0.034 mmol) of (4-benzyl-4-hydroxy-piperidin-1-yl)-(5-chloro-2-methyl-1H-indol-3-yl)-methanone and 5.8 mg (0.034 mmol) of benzyl bromide were prepared 14 mg (87%) of (1-benzyl-5-chloro-2-methyl-1H-indol-3-yl)-(4-benzyl-4-hydroxy-piperidin-1-yl)-methanone as a white solid.

ES-MS m/e (%): 473.3 (M+H$^+$).

Example 13

(4-Benzyl-4-hydroxy-piperidin-1-yl)-[5-chloro-1-(3-methoxy-benzyl)-2-methyl-1H-indol-3-yl]-methanone

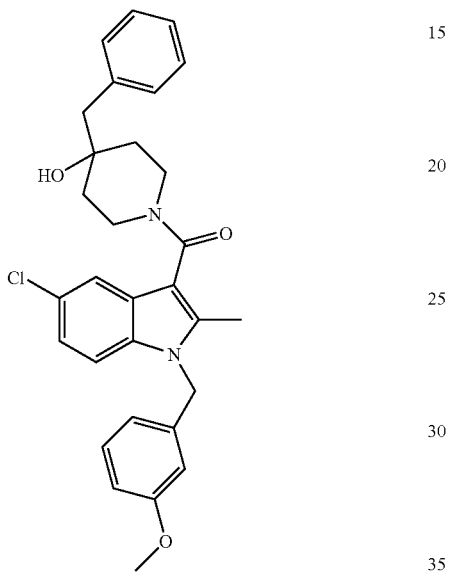

Using the procedure described for the preparation of (4-benzyl-4-hydroxy-piperidin-1-yl)-[1-(2-chloro-benzyl)-2-methyl-1H-indol-3-yl]-methanone, from 13 mg (0.034 mmol) of (4-benzyl-4-hydroxy-piperidin-1-yl)-(5-chloro-2-methyl-1H-indol-3-yl)-methanone and 6.8 mg (0.034 mmol) of 1-bromomethyl-3-methoxy-benzene were prepared 11 mg (65%) of (4-benzyl-4-hydroxy-piperidin-1-yl)-[5-chloro-1-(3-methoxy-benzyl)-2-methyl-1H-indol-3-yl]-methanone as a white solid.

ES-MS m/e (%): 503.5 (M+H$^+$).

Example 14

(4-Benzyl-4-hydroxy-piperidin-1-yl)-[1-(2-methoxy-benzyl)-2-methyl-1H-indol-3-yl]-methanone

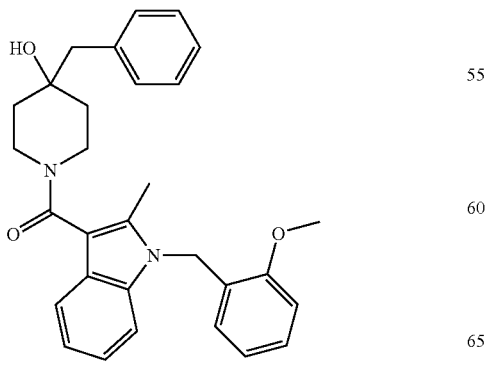

Using the procedure described for the preparation of (4-benzyl-4-hydroxy-piperidin-1-yl)-[1-(2-chloro-benzyl)-2-methyl-1H-indol-3-yl]-methanone, from 28 mg (0.080 mmol) of (4-benzyl-4-hydroxy-piperidin-1-yl)-(2-methyl-1H-indol-3-yl)-methanone and 15 mg (0.096 mmol) of 1-chloromethyl-2-methoxy-benzene were prepared 29 mg (77%) of (4-benzyl-4-hydroxy-piperidin-1-yl)-[1-(2-methoxy-benzyl)-2-methyl-1H-indol-3-yl]-methanone as a white solid.

ES-MS m/e (%): 469.6 (M+H$^+$).

Example 15

Benzyl-2-methyl-1H-indol-3-yl)-[4-(3-fluoro-phenoxy)-piperidin-1-yl]-methanone

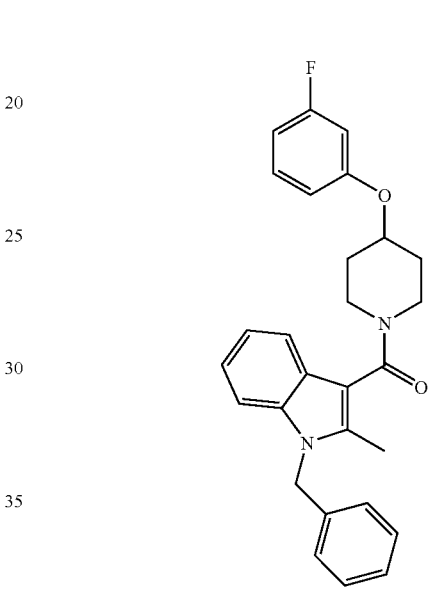

Amide coupling according to general procedure I:
Amine: 4-(3-Fluoro-phenoxy)-piperidine (described in US260294700),
Acid: 1-Benzyl-2-methyl-1H-indole-3-carboxylic acid,
ES-MS m/e (%): 443.6 (M+H$^+$).

Example 16

Benzyl-2-methyl-1H-indol-3-yl)-[4-(4-chloro-phenyl)-4-hydroxy-piperidin-1-yl]-methanone

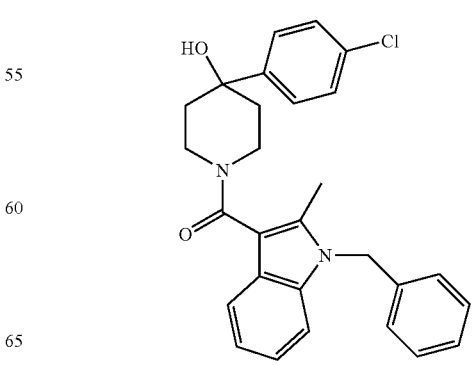

Amide coupling according to general procedure I:
Amine: 4-(4-Chloro-phenyl)-piperidin-4-ol (commercially available),
Acid: 1-Benzyl-2-methyl-1H-indole-3-carboxylic acid
ES-MS m/e (%): 459.5 (M+H+).

Example 17

Benzyl-2-methyl-1H-indol-3-yl)-[4-(4-bromo-phenyl)-4-hydroxy-piperidin-1-yl]-methanone

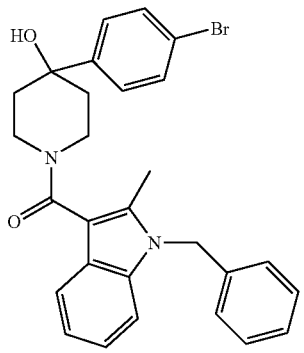

Amide coupling according to general procedure I:
Amine: 4-(4-Bromo-phenyl)-piperidin-4-ol (commercially available),
Acid: 1-Benzyl-2-methyl-1H-indole-3-carboxylic acid,
ES-MS m/e (%): 505.5 (M+H+).

Example 18

Benzyl-2-methyl-1H-indol-3-yl)-(4-hydroxy-4-phenyl-piperidin-1-yl)-methanone

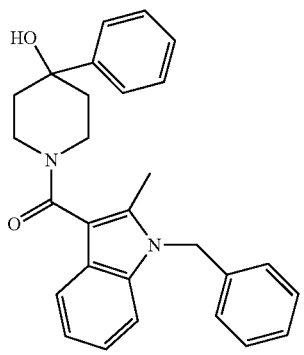

Amide coupling according to general procedure I:
Amine: 4-Phenyl-piperidin-4-ol (commercially available),
Acid: 1-Benzyl-2-methyl-1H-indole-3-carboxylic acid,
ES-MS m/e (%): 425.6 (M+H+).

Example 19

Benzyl-2-methyl-1H-indol-3-yl)-[4-(4-fluoro-phenyl)-4-hydroxy-piperidin-1-yl]-methanone

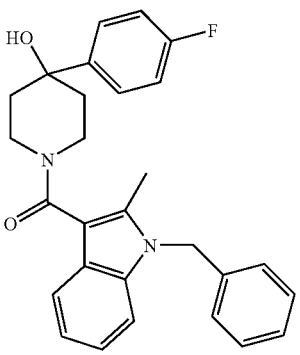

Amide coupling according to general procedure I:
Amine: 4-(4-Fluoro-phenyl)-piperidin-4-ol (commercially available),
Acid: 1-Benzyl-2-methyl-1H-indole-3-carboxylic acid,
ES-MS m/e (%): 443.6 (M+H+).

Example 20

Benzyl-2-methyl-1H-indol-3-yl)-[4-(4-chloro-3-trifluoromethyl-phenyl)-4-hydroxy-piperidin-1-yl]-methanone

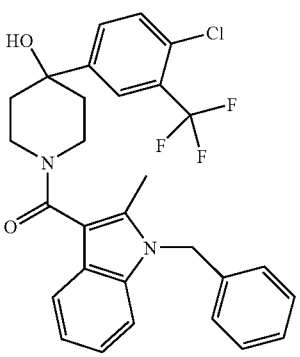

Amide coupling according to general procedure I:
Amine: 4-(4-Chloro-3-trifluoromethyl-phenyl)-piperidin-4-ol (commercially available),
Acid: 1-Benzyl-2-methyl-1H-indole-3-carboxylic acid
ES-MS m/e (%): 527.5 (M+H+).

Example 21

(4-Benzo[1,3]dioxol-5-yl-4-hydroxy-piperidin-1-yl)-(1-benzyl-2-methyl-1H-indol-3-yl)-methanone

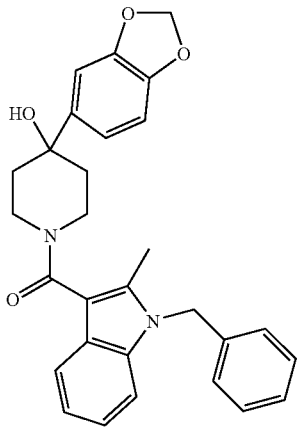

Amide coupling according to general procedure I:
Amine: 4-Benzo[1,3]dioxol-5-yl-piperidin-4-ol (described in WO9709311),
Acid: 1-Benzyl-2-methyl-1H-indole-3-carboxylic acid,
ES-MS m/e (%): 469.6 (M+H$^+$).

Example 22

Benzyl-2-methyl-1H-indol-3-yl)-(4-hydroxy-4-p-tolyl-piperidin-1-yl)-methanone

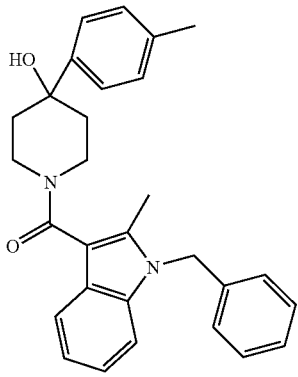

Amide coupling according to general procedure I:
Amine: 4-p-Tolyl-piperidin-4-ol (described in EP445701),
Acid: 1-Benzyl-2-methyl-1H-indole-3-carboxylic acid,
ES-MS m/e (%): 439.6 (M+H$^+$).

Example 23

Benzyl-2-methyl-1H-indol-3-yl)-[4-hydroxy-4-(3-trifluoromethyl-phenyl)-piperidin-1-yl]-methanone

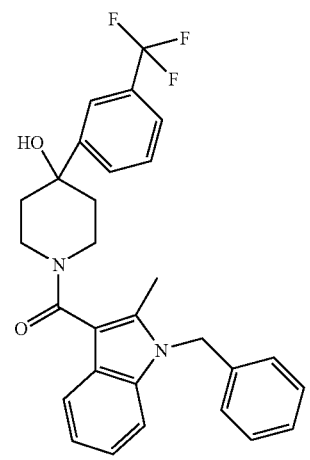

Amide coupling according to general procedure I:
Amine: 4-(3-Trifluoromethyl-phenyl)-piperidin-4-ol (commercially available),
Acid: 1-Benzyl-2-methyl-1H-indole-3-carboxylic acid,
ES-MS m/e (%): 493.6 (M+H$^+$).

Example 24

Benzyl-2-methyl-1H-indol-3-yl)-(4-phenyl-piperidin-1-yl)-methanone

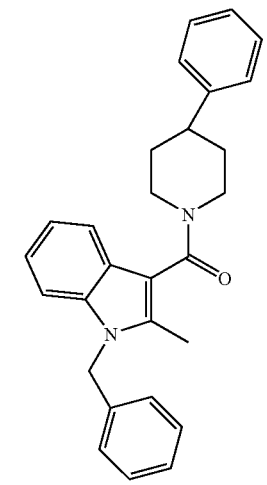

Amide coupling according to general procedure I:
Amine: 4-Phenyl-piperidine (commercially available),
Acid: 1-Benzyl-2-methyl-1H-indole-3-carboxylic acid
ES-MS m/e (%): 409.5 (M+H$^+$).

Example 25

(6-Chloro-1H-indol-3-yl)-(4-phenyl-piperidin-1-yl)-methanone

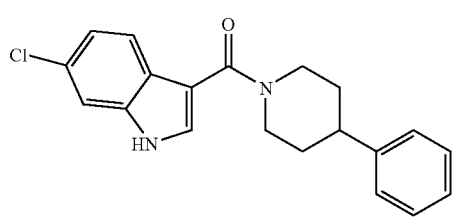

Amide coupling according to general procedure I:
Amine: 4-Phenyl-piperidine (commercially available),
Acid: 6-chloro-1H-indole-3-carboxylic acid,
ES-MS m/e (%): 339.4 (M+H$^+$).

Example 26

(6-Chloro-1H-indol-3-yl)-[4-hydroxy-4-(3-trifluoromethyl-phenyl)-piperidin-1-yl]-methanol

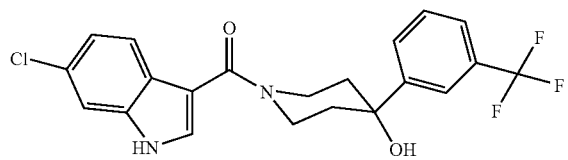

Amide coupling according to general procedure I:
Amine: 4-(3-Trifluoromethyl-phenyl)-piperidin-4-ol (commercially available),
Acid: 6-chloro-1H-indole-3-carboxylic acid,
ES-MS m/e (%): 423.4 (M+H$^+$).

Example 27

1-(6-Chloro-1H-indole-3-carbonyl)-4-phenyl-piperidine-4-carbonitrile

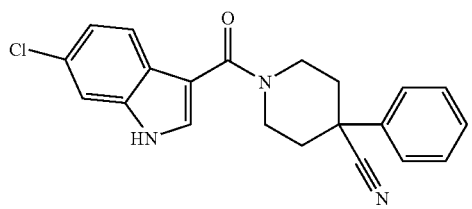

Amide coupling according to general procedure I:
Amine: 4-Phenyl-piperidine-4-carbonitrile (commercially available),
Acid: 6-chloro-1H-indole-3-carboxylic acid,
ES-MS m/e (%): 364.4 (M+H$^+$).

Example 28

(6-Chloro-1H-indol-3-yl)-(4-hydroxy-4-p-tolyl-piperidin-1-yl)-methanone

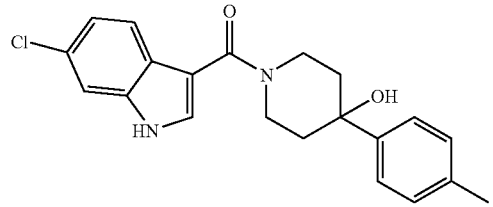

Amide coupling according to general procedure I:
Amine: 4-p-Tolyl-piperidin-4-ol (described in EP445701),
Acid: 6-chloro-1H-indole-3-carboxylic acid
ES-MS m/e (%): 369.4 (M+H$^+$).

Example 29

(6-Chloro-1H-indol-3-yl)-[4-(4-chloro-phenyl)-4-hydroxy-piperidin-1-yl]-methanone

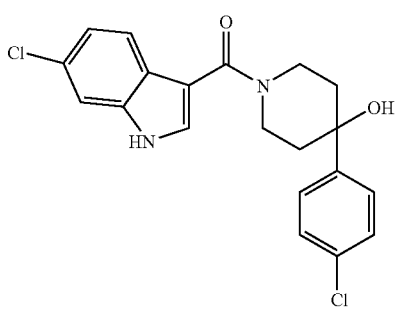

Amide coupling according to general procedure I:
Amine: 4-(4-Chloro-phenyl)-piperidin-4-ol (commercially available),
Acid: 6-chloro-1H-indole-3-carboxylic acid,
ES-MS m/e (%): 389.4 (M$^+$).

Example 30

(6-Chloro-1H-indol-3-yl)-[4-(4-chloro-3-trifluoromethyl-phenyl)-4-hydroxy-piperidin-1-yl]-methanone

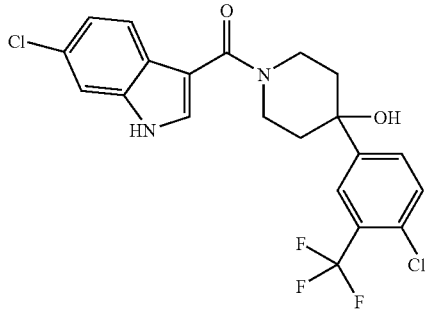

Amide coupling according to general procedure I:
Amine: 4-(4-Chloro-3-trifluoromethyl-phenyl)-piperidin-4-ol (commercially available),
Acid: 6-chloro-1H-indole-3-carboxylic acid,
ES-MS m/e (%): 457.4 (M$^+$).

Example 31

(4-Benzo[1,3]dioxol-5-yl-4-hydroxy-piperidin-1-yl)-(6-chloro-1H-indol-3-yl)-methanone

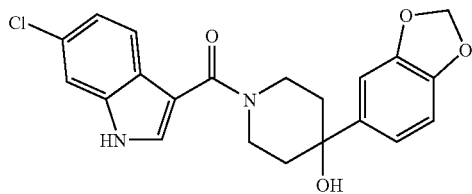

Amide coupling according to general procedure I:
Amine: 4-Benzo[1,3]dioxol-5-yl-piperidin-4-ol (described in WO9709311),
Acid: 6-chloro-1H-indole-3-carboxylic acid,
ES-MS m/e (%): 399.4 (M+H$^+$).

Example 32

[4-(4-Bromo-phenyl)-4-hydroxy-piperidin-1-yl]-(6-chloro-1H-indol-3-yl)-methanone

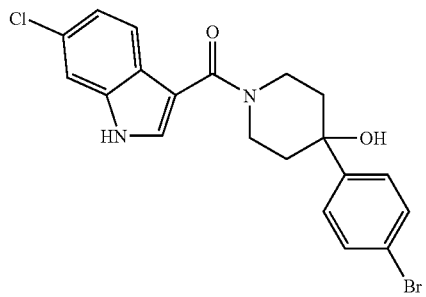

Amide coupling according to general procedure I:
Amine: 4-(4-Bromo-phenyl)-piperidin-4-ol (commercially available),
Acid: 6-chloro-1H-indole-3-carboxylic acid,
ES-MS m/e (%): 435.3 (M$^+$).

Example 33

[1-(6-chloro-1H-indole-3-carbonyl)-piperidin-4-yl]-carbamic acid tert-butyl ester

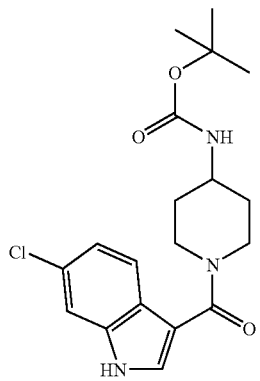

Amide coupling according to general procedure I:
Amine: Piperidin-4-yl-carbamic acid tert-butyl ester (commercially available),
Acid: 6-chloro-1H-indole-3-carboxylic acid,
ES-MS m/e (%): 378.3 (M+H$^+$).

Example 34

N-[1-(6-Chloro-1H-indole-3-carbonyl)-piperidin-4-yl]-2-fluoro-benzamide

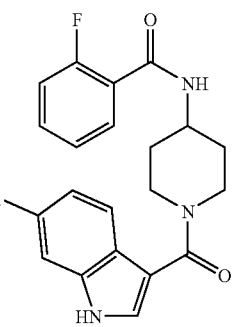

(4-Amino-piperidin-1-yl)-(6-chloro-1H-indol-3-yl)-methanone

To a stirred solution of 0.50 g (1.32 mmol) of [1-(6-chloro-1H-indole-3-carbonyl)-piperidin-4-yl]-carbamic acid tert-butyl ester (the preparation of which has been described in example 31) in CH$_2$Cl$_2$ (10 ml), were added 2 ml of TFA. The mixture was stirred 2 hours, then poured onto an aqueous solution of sat. NaHCO$_3$ and then extracted with ethyl acetate. The combined organic phases were dried over Na$_2$SO$_4$ and concentrated in vacuo, to afford 0.25 g (68%) of (4-amino-piperidin-1-yl)-(6-chloro-1H-indol-3-yl)-methanone as a light brown solid.
ES-MS m/e (%): 78.1 (M+H$^+$).

N-[1-(6-Chloro-1H-indole-3-carbonyl)-piperidin-4-yl]-2-fluoro-benzamide

To a stirred solution of 50 mg (0.36 mmol) 2-fluoro-benzoic acid in 5 ml CH$_2$Cl$_2$ were added 90 mg (0.47 mmol) EDC, 63 mg (0.47 mmol) HOBt, 60 µl (0.47 mmol) Et$_3$N and 100 mg (0.36 mmol) (4-amino-piperidin-1-yl)-(6-chloro-1H-indol-3-yl)-methanone. The mixture was stirred overnight at RT and then poured onto water and extracted with CH$_2$Cl$_2$. The combined organic phases were dried over Na$_2$SO$_4$ and concentrated in vacuo. Flash chromatography (ethyl acetate) afforded 82 mg (57%) N-[1-(6-Chloro-1H-indole-3-carbonyl)-piperidin-4-yl]-2-fluoro-benzamide of as a white solid.
ES-MS m/e (%): 400.3 (M+H$^+$).

Example 35

1-[1-(1-Cyclohexylmethyl-1H-indole-3-carbonyl)-piperidin-4-yl]-1,3-dihydro-benzoimidazol-2-one

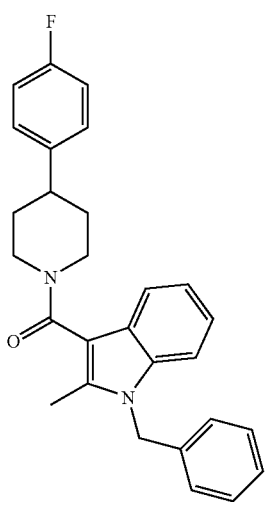

Following general procedure I, the coupling of (commercially available) 4-(4-fluoro-phenyl)-piperidine with 1-benzyl-2-methyl-1H-indole-3-carboxylic acid gave the title compound.

ES-MS m/e (%): 427.6 (M+H$^+$).

Example 36

(6-Chloro-1H-indol-3-yl)-[4-(4-chloro-phenyl)-4-hydroxy-piperidin-1-yl]-methanone

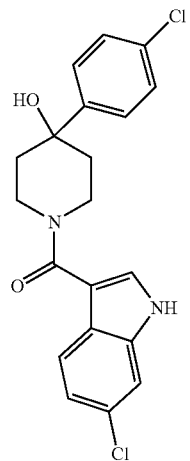

Following general procedure I, the coupling of (commercially available) 4-(4-chloro-phenyl)-piperidin-4-ol with 6-chloro-1H-indole-3-carboxylic acid gave the title compound.

ES-MS m/e (%): 389.4 (M+H$^+$).

Example 37

(6-Chloro-1H-indol-3-yl)-[4-(4-nitro-phenyl)-piperidin-1-yl]-methanone

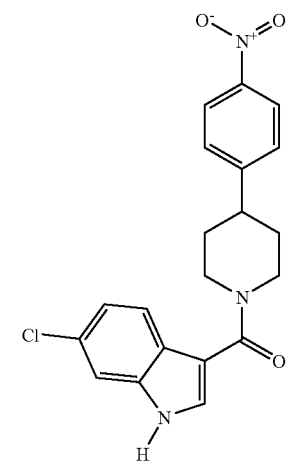

Following general procedure I, the coupling of (commercially available) 4-(4-nitro-phenyl)-piperidine with 6-chloro-1H-indole-3-carboxylic acid gave the title compound.

ES-MS m/e (%): 384.4 (M+H$^+$).

Example 38

(6-Chloro-1H-indol-3-yl)-[4-(3-chloro-phenyl)-piperidin-1-yl]-methanone

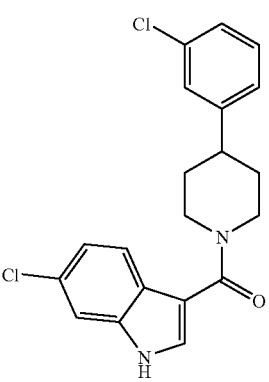

Following general procedure I, the coupling of (commercially available) 4-(3-chloro-phenyl)-piperidine with 6-chloro-1H-indole-3-carboxylic acid gave the title compound.

ES-MS m/e (%): 373.3 (M+H$^+$).

Example 39

(6-Chloro-1H-indol-3-yl)-[4-(2-hydroxy-phenyl)-piperidin-1-yl]-methanone

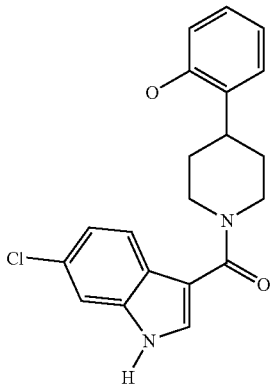

Following general procedure I, the coupling of (commercially available) 2-piperidin-4-yl-phenol with 6-chloro-1H-indole-3-carboxylic acid gave the title compound.

ES-MS m/e (%): 355.4 (M+H$^+$).

Example 40

(6-Chloro-1H-indol-3-yl)-[4-(2,6-dimethoxy-phenyl)-piperidin-1-yl]-methanone

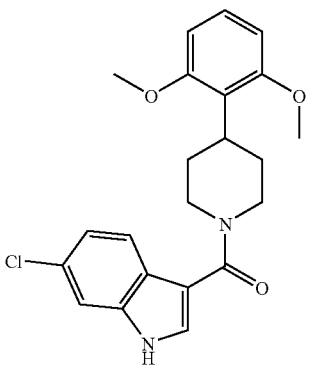

Following general procedure I, the coupling of (commercially available) 4-(2,6-dimethoxy-phenyl)-piperidine with 6-chloro-1H-indole-3-carboxylic acid gave the title compound.

ES-MS m/e (%): 399.2 (M+H$^+$).

Example 41

(6-Chloro-1H-indol-3-yl)-[4-(4-fluoro-phenyl)-piperidin-1-yl]-methanone

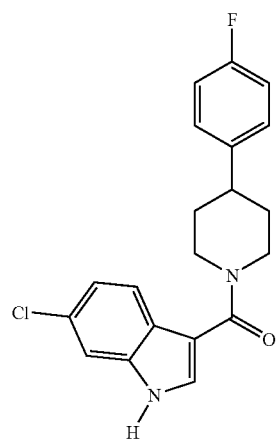

Following general procedure I, the coupling of (commercially available) 4-(4-fluoro-phenyl)-piperidine with 6-chloro-1H-indole-3-carboxylic acid gave the title compound.

ES-MS m/e (%): 357.4 (M+H$^+$).

Example 42

(6-Chloro-1H-indol-3-yl)-(4-methoxy-4-phenyl-piperidin-1-yl)-methanone

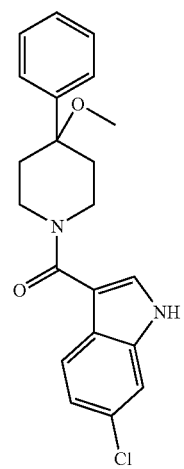

Following general procedure I, the coupling of 4-methoxy-4-phenyl-piperidine (described in WO 9800400) with 6-chloro-1H-indole-3-carboxylic acid gave the title compound.

ES-MS m/e (%): 369.4 (M+H$^+$).

Example 43

2-{6-Chloro-3-[4-(2,6-dimethoxy-phenyl)-piperidine-1-carbonyl]-indol-1-yl}-N,N-dimethyl-acetamide

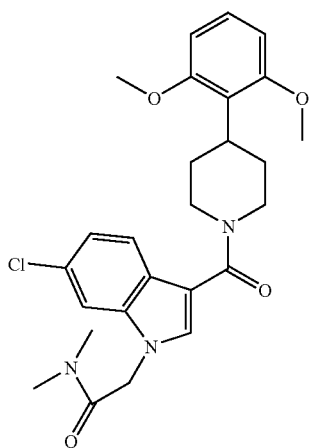

Following general procedure II, the alkylation of (6-chloro-1H-indol-3-yl)-[4-(2,6-dimethoxy-phenyl)-piperidin-1-yl]-methanone (preparation described herein), with commercially available 2-chloro-N,N-dimethyl-acetamide gave the title compound.

ES-MS m/e (%): 484.3 (M+H$^+$).

Example 44

2-{6-Chloro-3-[4-(2,6-dimethoxy-phenyl)-piperidine-1-carbonyl]-indol-1-yl}-1-pyridin-2-yl-ethanone

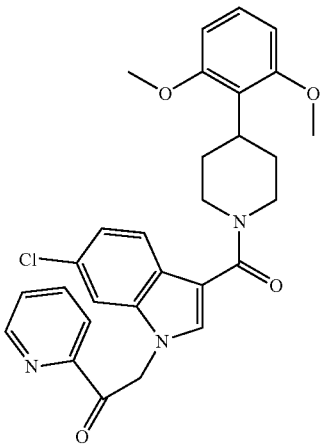

Following general procedure II, the alkylation of (6-chloro-1H-indol-3-yl)-[4-(2,6-dimethoxy-phenyl)-piperidin-1-yl]-methanone (preparation described herein), with commercially available 2-chloro-1-pyridin-2-yl-ethanone gave the title compound.

ES-MS m/e (%): 518.4 (M+H$^+$).

Example 45

(6-Chloro-1-pyridin-4-ylmethyl-1H-indol-3-yl)-[4-(2,6-dimethoxy-phenyl)-piperidin-1-yl]-methanone

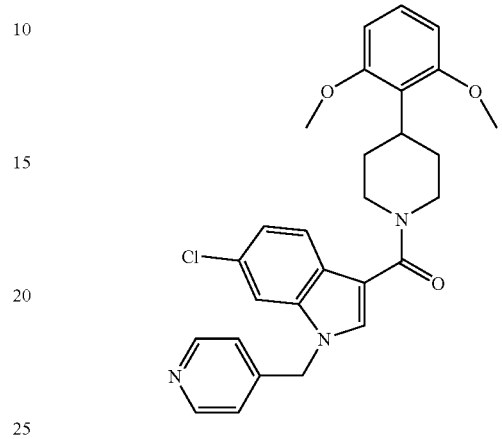

Following general procedure II, the alkylation of (6-chloro-1H-indol-3-yl)-[4-(2,6-dimethoxy-phenyl)-piperidin-1-yl]-methanone (preparation described herein), with commercially available 4-chloromethyl-pyridine gave the title compound.

ES-MS m/e (%): 490.3 (M+H$^+$).

Example 46

(6-Chloro-1-pyridin-3-ylmethyl-1H-indol-3-yl)-[4-(2,6-dimethoxy-phenyl)-piperidin-1-yl]-methanone

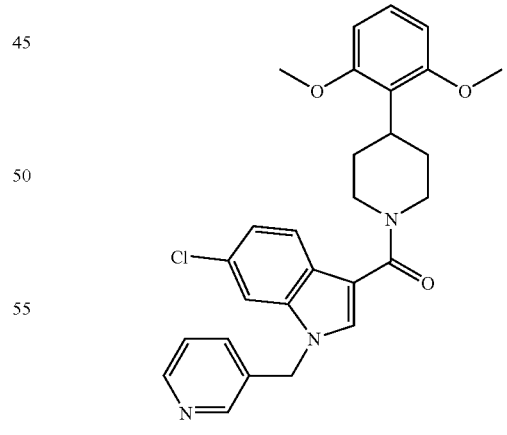

Following general procedure II, the alkylation of (6-chloro-1H-indol-3-yl)-[4-(2,6-dimethoxy-phenyl)-piperidin-1-yl]-methanone (preparation described herein), with commercially available 3-chloromethyl-pyridine gave the title compound.

ES-MS m/e (%): 490.3 (M+H$^+$).

Example 47

(6-Chloro-1-pyridin-2-ylmethyl-1H-indol-3-yl)-[4-(2,6-dimethoxy-phenyl)-piperidin-1-yl]-methanone

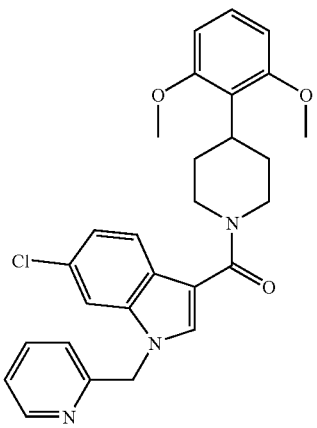

Following general procedure II, the alkylation of (6-chloro-1H-indol-3-yl)-[4-(2,6-dimethoxy-phenyl)-piperidin-1-yl]-methanone (preparation described herein), with methanesulfonic acid pyridin-2-ylmethyl ester (described in WO 9955318) gave the title compound.

ES-MS m/e (%): 490.3 (M+H$^+$).

Example 48

[6-Chloro-1-(6-chloro-pyridin-3-ylmethyl)-1H-indol-3-yl]-[4-(2,6-dimethoxy-phenyl)-piperidin-1-yl]-methanone

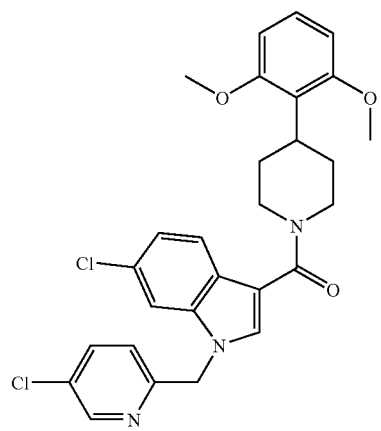

Following general procedure II, the alkylation of (6-chloro-1H-indol-3-yl)-[4-(2,6-dimethoxy-phenyl)-piperidin-1-yl]-methanone (preparation described herein), with methanesulfonic acid 6-chloro-pyridin-3-ylmethyl ester (described in Journal of Organic Chemistry (1999), 64(23), 8576-8581) gave the title compound.

ES-MS m/e (%): 524.2 (M+H$^+$).

Example 49

{6-Chloro-3-[4-(2,6-dimethoxy-phenyl)-piperidine-1-carbonyl]-indol-1-yl}-acetic acid tert-butyl ester

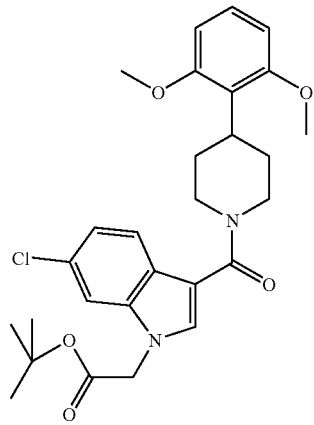

Following general procedure II, the alkylation of (6-chloro-1H-indol-3-yl)-[4-(2,6-dimethoxy-phenyl)-piperidin-1-yl]-methanone (preparation described herein), with (commercially available) bromo-acetic acid tert-butyl ester gave the title compound.

ES-MS m/e (%): 513.3 (M+H$^+$).

Example 50

6-Chloro-1-pyrazin-2-ylmethyl-1H-indol-3-yl)-[4-(2,6-dimethoxy-phenyl)-piperidin-1-yl]-methanone

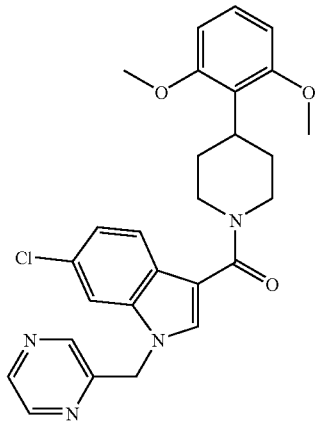

Following general procedure II, the alkylation of (6-chloro-1H-indol-3-yl)-[4-(2,6-dimethoxy-phenyl)-piperidin-1-yl]-methanone (preparation described herein), with methanesulfonic acid pyrazin-2-ylmethyl ester (described in WO 2002064574) gave the title compound.

ES-MS m/e (%): 491.1 (M+H$^+$).

Example 51

[6-Chloro-1-(3,5-difluoro-benzyl)-1H-indol-3-yl]-[4-(2,6-dimethoxy-phenyl)-piperidin-1-yl]-methanone

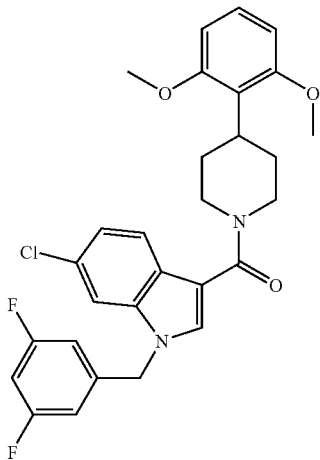

Following general procedure II, the alkylation of (6-chloro-1H-indol-3-yl)-[4-(2,6-dimethoxy-phenyl)-piperidin-1-yl]-methanone (preparation described herein), with (commercially available) 1-chloromethyl-3,5-difluoro-benzene gave the title compound.

ES-MS m/e (%): 525.3 (M+H$^+$).

Example 52

[6-Chloro-1-(2-dimethylamino-ethyl)-1H-indol-3-yl]-[4-(2,6-dimethoxy-phenyl)-piperidin-1-yl]-methanone

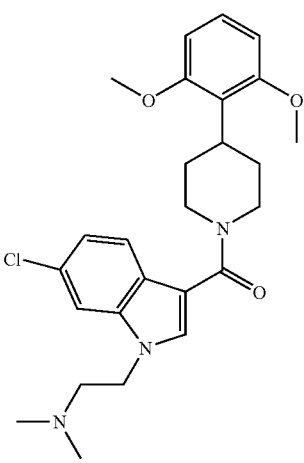

Following general procedure II, the alkylation of (6-chloro-1H-indol-3-yl)-[4-(2,6-dimethoxy-phenyl)-piperidin-1-yl]-methanone (preparation described herein), with (commercially available) (2-chloro-ethyl)-dimethyl-amine gave the title compound.

ES-MS m/e (%): 470.5 (M+H$^+$).

Example 53

(6-Chloro-1H-indol-3-yl)-[4-(2-isopropoxy-phenyl)-piperidin-1-yl]-methanone

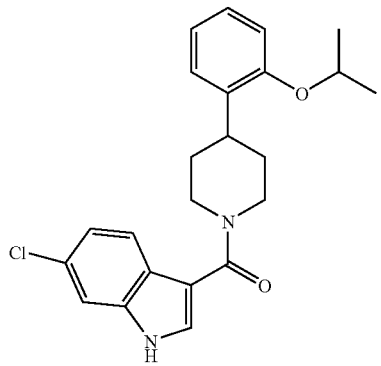

Following general procedure I, the coupling of 4-(2-isopropoxy-phenyl)-piperidine (described in Journal of Medicinal Chemistry (1998), 41(12), 1997-2009) with 6-chloro-1H-indole-3-carboxylic acid gave the title compound.

ES-MS m/e (%): 397.1 (M+H$^+$).

Example 54

(6-Chloro-1H-indol-3-yl)-[4-(2-methoxy-phenyl)-piperidin-1-yl]-methanone

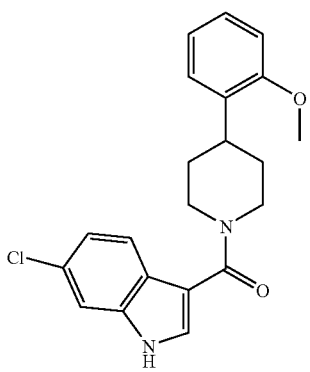

Following general procedure I, the coupling of (commercially available) 4-(2-methoxy-phenyl)-piperidine with 6-chloro-1H-indole-3-carboxylic acid gave the title compound.

ES-MS m/e (%): 367.0 (M+H$^+$).

Example 55

2-{6-Chloro-3-[4-(2,6-dimethoxy-phenyl)-piperidine-1-carbonyl]-indol-1-yl}-1-(4-methyl-piperazin-1-yl)-ethanone

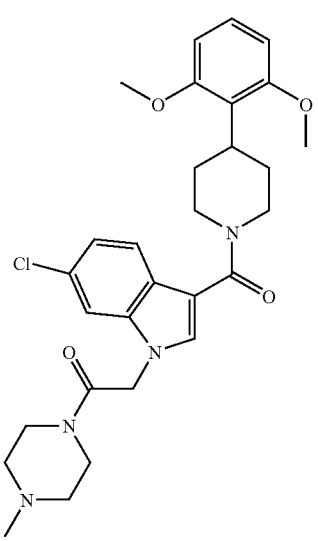

Following general procedure II, the alkylation of (6-chloro-1H-indol-3-yl)-[4-(2,6-dimethoxy-phenyl)-piperidin-1-yl]-methanone (preparation described herein), with (commercially available) 2-chloro-1-(4-methyl-piperazin-1-yl)-ethanone gave the title compound.

ES-MS m/e (%): 539.6 (M+H$^+$).

Example 56

[6-Chloro-1-(3,5-difluoro-benzyl)-1H-indol-3-yl]-[4-(2-methoxy-phenyl)-piperidin-1-yl]-methanone

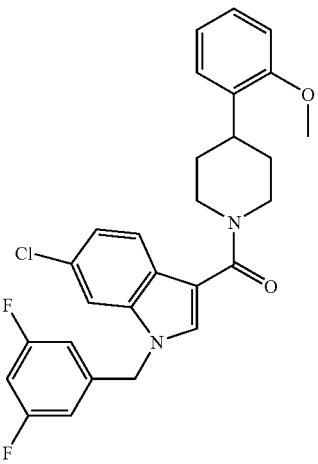

Following general procedure II, the alkylation of (6-chloro-1H-indol-3-yl)-[4-(2-methoxy-phenyl)-piperidin-1-yl]-methanone (preparation described herein), with (commercially available) 1-chloromethyl-3,5-difluoro-benzene gave the title compound.

ES-MS m/e (%): 495.2 (M+H$^+$).

Example 57

2-{6-Chloro-3-[4-(2-methoxy-phenyl)-piperidine-1-carbonyl]-indol-1-yl}-N,N-dimethyl-acetamide

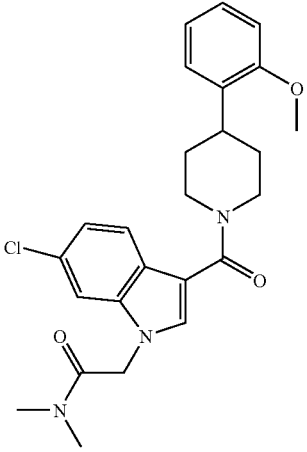

Following general procedure II, the alkylation of (6-chloro-1H-indol-3-yl)-[4-(2-methoxy-phenyl)-piperidin-1-yl]-methanone (preparation described herein), with (commercially available) 2-chloro-N,N-dimethyl-acetamide gave the title compound.

ES-MS m/e (%): 454.3 (M+H$^+$).

Example 58

2-{6-Chloro-3-[4-(2-methoxy-phenyl)-piperidine-1-carbonyl]-indol-1-yl}-1-(4-methyl-piperazin-1-yl)-ethanone

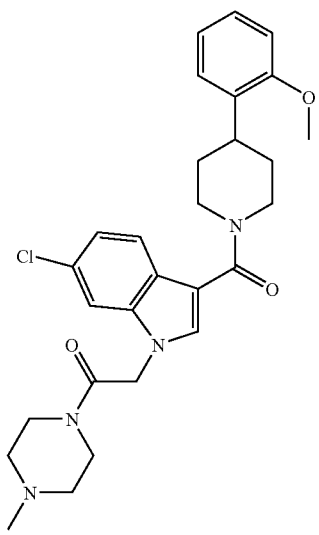

Following general procedure II, the alkylation of (6-chloro-1H-indol-3-yl)-[4-(2-methoxy-phenyl)-piperidin-1-yl]-methanone (preparation described herein), with (commercially available) 2-chloro-1-(4-methyl-piperazin-1-yl)-ethanone gave the title compound.

ES-MS m/e (%): 509.3 (M+H⁺).

Example 59

{6-Chloro-3-[4-(2-methoxy-phenyl)-piperidine-1-carbonyl]-indol-1-yl}-acetic acid tert-butyl ester

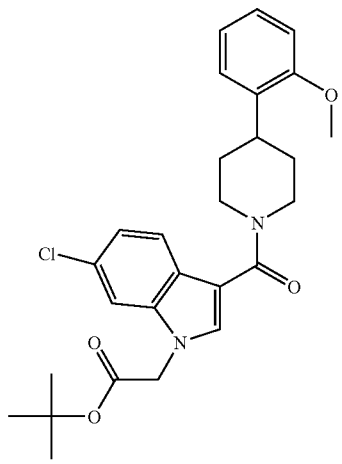

Following general procedure II, the alkylation of (6-chloro-1H-indol-3-yl)-[4-(2-methoxy-phenyl)-piperidin-1-yl]-methanone (preparation described herein), with (commercially available) bromo-acetic acid tert-butyl ester gave the title compound.

ES-MS m/e (%): 483.3 (M+H⁺).

Example 60

2-{6-Chloro-3-[4-cyano-4-(2-methoxy-phenyl)-piperidine-1-carbonyl]-indol-1-yl}-N,N-dimethyl-acetamide

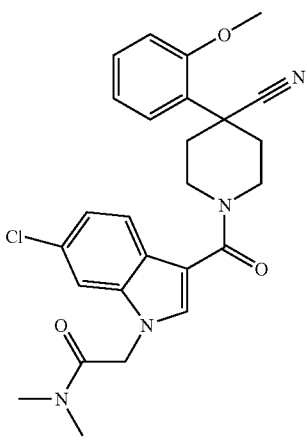

Amide coupling according to general procedure I:
Amine: 4-(2-Methoxy-phenyl)-piperidine-4-carbonitrile (described in WO2003053361),
Acid: 6-Chloro-1-dimethylcarbamoylmethyl-1H-indole-3-carboxylic acid,
ES-MS m/e (%): 479.1 (M+H⁺).

Example 61

2-{6-Chloro-3-[4-cyano-4-(2-fluoro-phenyl)-piperidine-1-carbonyl]-indol-1-yl}-N,N-dimethyl-acetamide

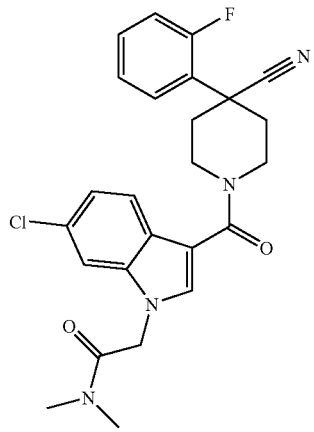

Amide coupling according to general procedure I:
Amine: 4-(2-Fluoro-phenyl)-piperidine-4-carbonitrile (described in *Tetrahedron* 2004, 4875),
Acid: 6-Chloro-1-dimethylcarbamoylmethyl-1H-indole-3-carboxylic acid,
ES-MS m/e (%): 467.1 (M+H⁺).

Example 62

2-{3-[4-(2,6-Dimethoxy-phenyl)-piperidine-1-carbonyl]-indol-1-yl}-N,N-dimethyl-acetamide

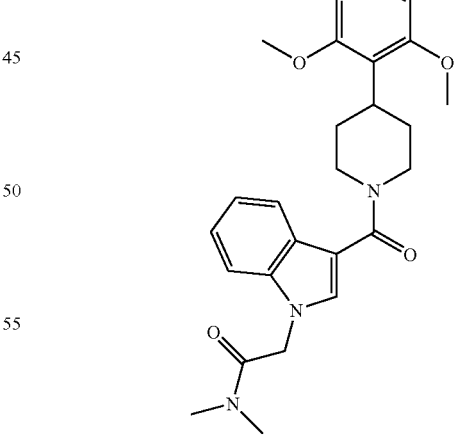

Following general procedure II, the alkylation of (6-chloro-1H-indol-3-yl)-[4-(2,6-dimethoxy-phenyl)-piperidin-1-yl]-methanone (preparation described herein), with (commercially available) 2-chloro-N,N-dimethyl-acetamide gave the title compound.

ES-MS m/e (%): 450.6 (M+H⁺).

Example 63

[6-Chloro-1-(2-methyl-pyridin-4-ylmethyl)-1H-indol-3-yl]-[4-(2,6-dimethoxy-phenyl)-piperidin-1-yl]-methanone

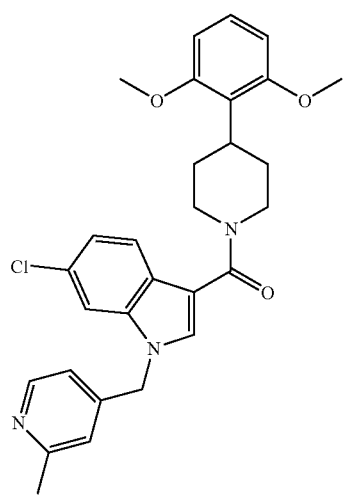

Following general procedure II, the alkylation of (6-chloro-1H-indol-3-yl)-[4-(2,6-dimethoxy-phenyl)-piperidin-1-yl]-methanone (preparation described herein), with methanesulfonic acid 2-methyl-pyridin-4-ylmethyl ester (prepared by mesylation of the commercially available (2-methyl-pyridin-4-yl)-methanol) gave the title compound.

ES-MS m/e (%): 504.1 (M+H$^+$).

Example 64

2-{3-[4-(2,6-Dimethoxy-phenyl)-piperidine-1-carbonyl]-indol-1-yl}-1-(4-methyl-piperazin-1-yl)-ethanone

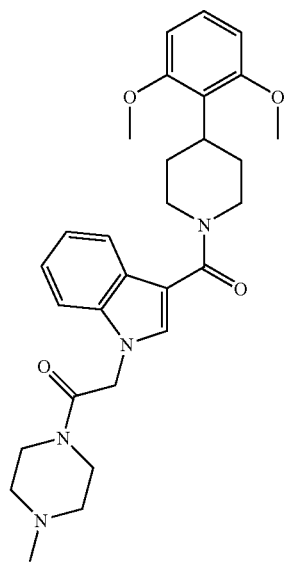

Following general procedure II, the alkylation of (6-chloro-1H-indol-3-yl)-[4-(2,6-dimethoxy-phenyl)-piperidin-1-yl]-methanone (preparation described herein), with (commercially available) 2-chloro-1-(4-methyl-piperazin-1-yl)-ethanone gave the title compound.

ES-MS m/e (%): 505.4 (M+H$^+$).

Example 65

2-{6-Chloro-3-[4-(2,6-dimethoxy-phenyl)-piperidine-1-carbonyl]-indol-1-yl}-N-(2-dimethylamino-ethyl)-acetamide {6-Chloro-3-[4-(2,6-dimethoxy-phenyl)-piperidine-1-carbonyl]-indol-1-yl}-acetic acid Following general procedure II, the alkylation of (6-chloro-1H-indol-3-yl)-[4-(2,6-dimethoxy-phenyl)-piperidin-1-yl]-methanone (preparation described herein), with (commercially available) bromo-acetic acid gave the title compound.

ES-MS m/e (%): 457.5 (M+H$^+$).

2-{6-Chloro-3-[4-(2,6-dimethoxy-phenyl)-piperidine-1-carbonyl]-indol-1-yl}-N-(2-dimethylamino-ethyl)-acetamide

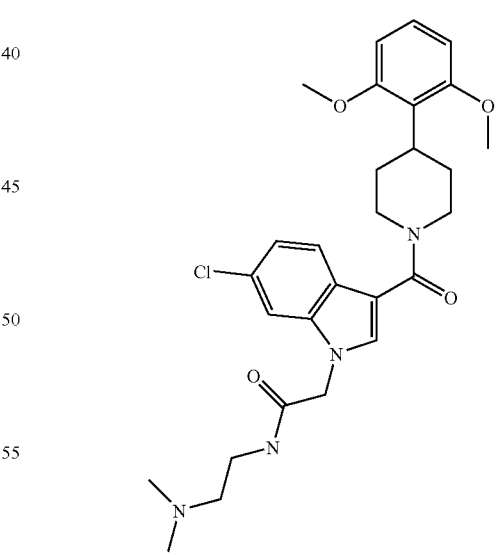

Analogous to general procedure I, the coupling of {6-chloro-3-[4-(2,6-dimethoxy-phenyl)-piperidine-1-carbonyl]-indol-1-yl}-acetic acid with (commercially available) N$^1$,N$^1$-dimethyl-ethane-1,2-diamine gave the title compound.

ES-MS m/e (%): 527.3 (M+H$^+$).

Example 66

2-{6-Chloro-3-[4-(2-isopropoxy-phenyl)-piperidine-1-carbonyl]-indol-1-yl}-N,N-dimethyl-acetamide

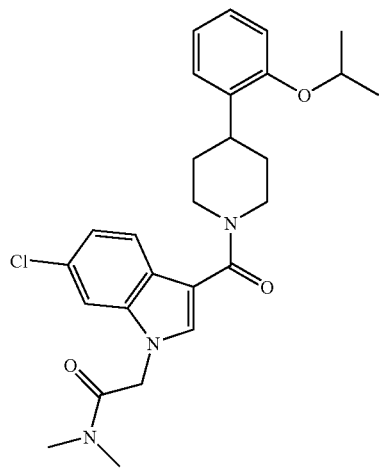

Following general procedure II, the alkylation of (6-chloro-1H-indol-3-yl)-[4-(2-isopropoxy-phenyl)-piperidin-1-yl]-methanone (preparation described herein), with (commercially available) 2-chloro-N,N-dimethyl-acetamide gave the title compound.

ES-MS m/e (%): 482.6 (M+H$^+$).

Example 67

2-{6-Chloro-3-[4-(2-isopropoxy-phenyl)-piperidine-1-carbonyl]-indol-1-yl}-1-(4-methyl-piperazin-1-yl)-ethanone

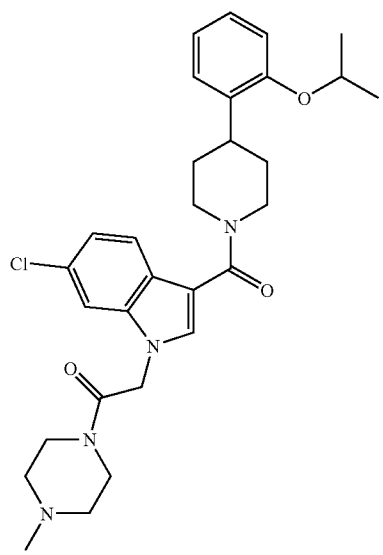

Following general procedure II, the alkylation of (6-chloro-1H-indol-3-yl)-[4-(2-isopropoxy-phenyl)-piperidin-1-yl]-methanone (preparation described herein), with (commercially available) 2-chloro-1-(4-methyl-piperazin-1-yl)-ethanone gave the title compound.

ES-MS m/e (%): 537.6 (M+H$^+$).

Example 68

2-{6-Chloro-3-[4-(2-methoxy-phenyl)-piperidine-1-carbonyl]-indol-1-yl}-1-piperazin-1-yl-ethanone {6-Chloro-3-[4-(2-methoxy-phenyl)-piperidine-1-carbonyl]-indol-1-yl}-acetic acid Following general procedure II, the alkylation of (6-chloro-1H-indol-3-yl)-[4-(2-methoxy-phenyl)-piperidin-1-yl]-methanone (preparation described herein), with (commercially available) bromo-acetic acid gave the title compound.

ES-MS m/e (%): 427.5 (M+H$^+$).

2-{6-Chloro-3-[4-(2-methoxy-phenyl)-piperidine-1-carbonyl]-indol-1-yl}-1-piperazin-1-yl-ethanone

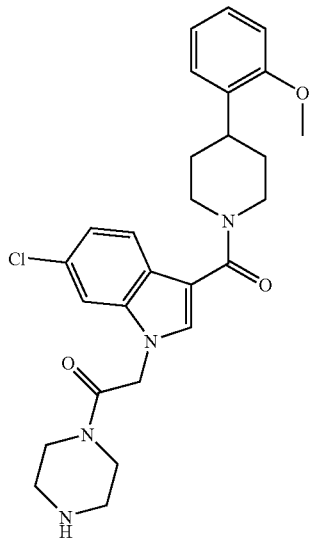

Analogous to general procedure I, the coupling of {6-chloro-3-[4-(2-methoxy-phenyl)-piperidine-1-carbonyl]-indol-1-yl}-acetic acid with (commercially available) piperazine-1-carboxylic acid tert-butyl ester gave, after treatment with TFA and neutralisation, the title compound.

ES-MS m/e (%): 495.5 (M+H$^+$).

Example 69

2-{6-Chloro-3-[4-(2,6-dimethoxy-phenyl)-piperidine-1-carbonyl]-indol-1-yl}-1-piperazin-1-yl-ethanone

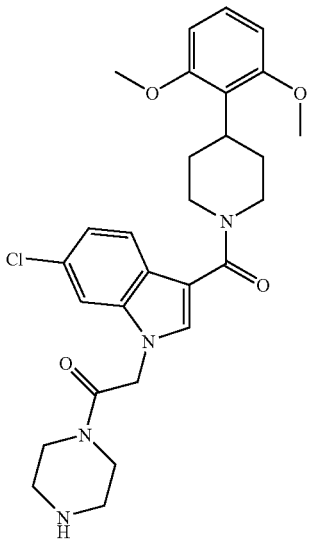

Analogous to general procedure I, the coupling of {6-chloro-3-[4-(2,6-dimethoxy-phenyl)-piperidine-1-carbonyl]-indol-1-yl}-acetic acid (prepared herein) with (commercially available) piperazine-1-carboxylic acid tert-butyl ester gave, after treatment with TFA and neutralisation, the title compound.

ES-MS m/e (%): 525.5 (M+H$^+$).

Example 70

(6-Chloro-1H-indol-3-yl)-[4-(2,3-dihydro-benzofuran-7-yl)-piperidin-1-yl]-methanone 4-(5-Bromo-2,3-dihydro-benzofuran-7-yl)-pyridine 4-Bromopyridine or hydrochloride salt thereof was dissolved in DME under argon and Pd(Ph$_3$P)$_4$ (3 mol %) was added. The mixture was stirred for 10 min at 50° C. To this solution was added (commercially available) 5-bromo-2,3-dihydrobenzo[b]furan-7-boronic acid dissolved in a minimum amount of EtOH/DME 1:2 followed by 2N Na$_2$CO$_3$. The reaction mixture was refluxed (110° C.) under stirring for 2 h. The flask was cooled to RT, the mixture was treated with sat. aq. NH$_4$Cl solution and extracted with CHCl$_3$. Evaporation and purification by SiO$_2$ gel chromatography (hexane/ethyl acetate: 4/1) gave the title compound in 76% yield.

ES-MS m/e (%): 275.9 (M+H$^+$).

1-Benzyl-4-(5-bromo-2,3-dihydro-benzofuran-7-yl)-1,2,3,6-tetrahydro-pyridine

To a solution of 4-(5-bromo-2,3-dihydro-benzofuran-7-yl)-pyridine in toluene was added benzyl bromide (1 eq.) and the reaction mixture was stirred under reflux for 14 h. Reaction was monitored by TLC (CH$_2$Cl$_2$/MeOH 95:5) and revealed total conversion to an intermediate. Complete evaporation of the solvent gave a white solid. The solid was dissolved in MeOH under argon and cooled down to 0° C., NaBH$_4$ (2.05 eq.) was added portion-wise (exothermic reaction) and the reaction mixture was stirred for 3 h at RT. Evaporation of MeOH, redissolution in CH$_2$Cl$_2$ and sequential washing with 1N NaHCO$_3$ and brine, followed by purification by SiO$_2$ gel chromatography (CH$_2$Cl$_2$/MeOH: 98/2) gave 71% yield of the title compound.

ES-MS m/e (%): 370.0 (M+H$^+$).

4-(2,3-Dihydro-benzofuran-7-yl)-piperidine

To a solution of 1-benzyl-4-(5-bromo-2,3-dihydro-benzofuran-7-yl)-1,2,3,6-tetrahydro-pyridine in EtOH and 4N HCl was added 40 wt % of 10% Pd/C catalyst. The reaction flask was charged with H$_2$ (3.5 bar) and then stirred overnight at 50° C. The reaction mixture was filtered over Celite under argon. The solvents were evaporated and the product was partitioned between CH$_2$Cl$_2$ and aq. K$_2$CO$_3$. The organic phase was dried over Na$_2$SO$_4$ and evaporated to give the title compound in 81% yield.

ES-MS m/e (%): 204.3 (M+H$^+$).

(6-Chloro-1H-indol-3-yl)-[4-(2,3-dihydro-benzofuran-7-yl)-piperidin-1-yl]-methanone

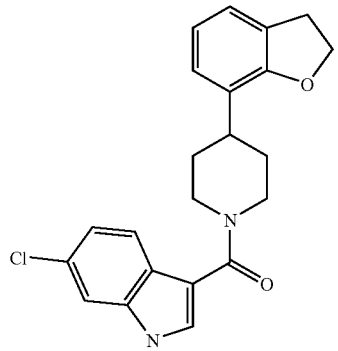

Following general procedure I, the coupling of 4-(2,3-dihydro-benzofuran-7-yl)-piperidine (described herein below) with 6-chloro-1H-indole-3-carboxylic acid gave the title compound.

ES-MS m/e (%): 381.1 (M+H$^+$).

Example 71

2-{6-Chloro-3-[4-(2,3-dihydro-benzofuran-7-yl)-piperidine-1-carbonyl]-indol-1-yl}-1-(4-methyl-piperazin-1-yl)-ethanone

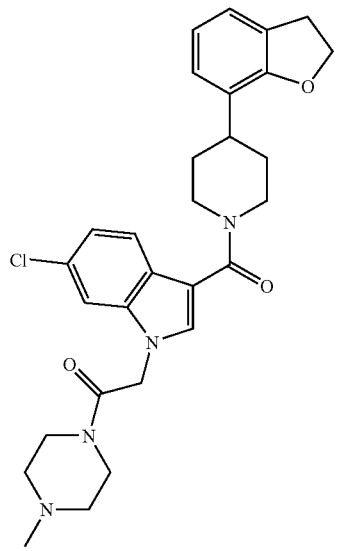

Following general procedure II, the alkylation of (6-chloro-1H-indol-3-yl)-[4-(2,3-dihydro-benzofuran-7-yl)-piperidin-1-yl]-methanone (preparation described herein), with (commercially available) 2-chloro-1-(4-methyl-piperazin-1-yl)-ethanone gave the title compound.

ES-MS m/e (%): 521.6 (M+H⁺).

Example 72

2-{6-Chloro-3-[4-(2,3-dihydro-benzofuran-7-yl)-piperidine-1-carbonyl]-indol-1-yl}-N,N-dimethyl-acetamide

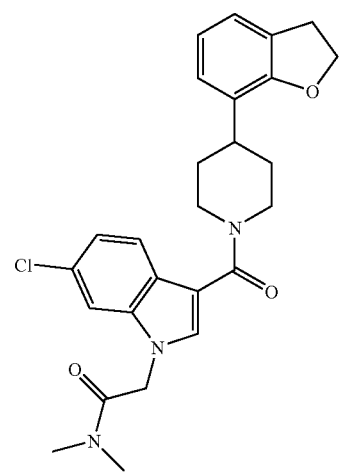

Following general procedure II, the alkylation of (6-chloro-1H-indol-3-yl)-[4-(2,3-dihydro-benzofuran-7-yl)-piperidin-1-yl]-methanone (preparation described herein), with (commercially available) 2-chloro-N,N-dimethyl-acetamide gave the title compound.

ES-MS m/e (%): 466.6 (M+H⁺).

Example 73

2-{6-Chloro-3-[4-(2,3-dihydro-benzofuran-7-yl)-piperidine-1-carbonyl]-indol-1-yl}-N-(2-dimethy-lamino-ethyl)-acetamide {6-Chloro-3-[4-(2,3-dihydro-benzofuran-7-yl)-piperidine-1-carbonyl]-indol-1-yl}-acetic acid Following general procedure II, the alkylation of (6-chloro-1H-indol-3-yl)-[4-(2,3-dihydro-benzofuran-7-yl)-piperidin-1-yl]-methanone (preparation described herein), with (commercially available) bromo-acetic acid gave the title compound.

ES-MS m/e (%): 437.1 (M−H⁺).

2-{6-Chloro-3-[4-(2,3-dihydro-benzofuran-7-yl)-piperidine-1-carbonyl]-indol-1-yl}-N-(2-dimethy-lamino-ethyl)-acetamide

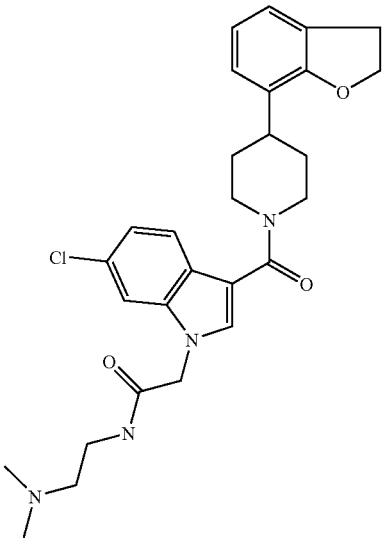

Analogous to general procedure I, the coupling of {6-chloro-3-[4-(2,3-dihydro-benzofuran-7-yl)-piperidine-1-carbonyl]-indol-1-yl}-acetic acid with (commercially available) N¹,N¹-dimethyl-ethane-1,2-diamine gave the title compound.

ES-MS m/e (%): 509.6 (M+H⁺).

Example 74

2-{6-Chloro-3-[4-(2,3-dihydro-benzofuran-7-yl)-piperidine-1-carbonyl]-indol-1-yl}-1-piperazin-1-yl-ethanone

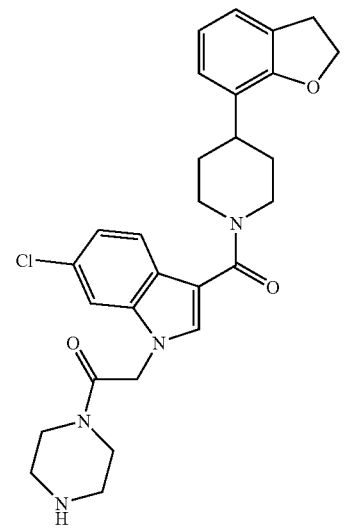

Analogous to general procedure I, the coupling of {6-chloro-3-[4-(2,3-dihydro-benzofuran-7-yl)-piperidine-1-carbonyl]-indol-1-yl}-acetic acid (prepared described herein) with (commercially available) piperazine-1-carboxylic acid tert-butyl ester gave, after treatment with TFA and neutralisation, the title compound.

ES-MS m/e (%): 507.0 (M+H⁺).

Example 75

2-{6-Chloro-3-[4-(2-methoxy-phenyl)-piperidine-1-carbonyl]-5-methyl-indol-1-yl}-N,N-dimethyl-acetamide

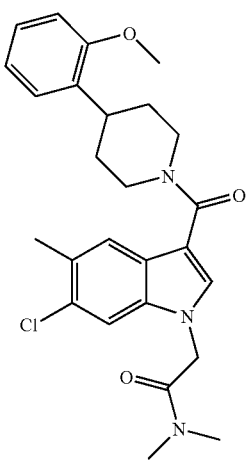

Amide coupling according to general procedure I:
Amine: 4-(2-Methoxy-phenyl)-piperidine (commercially available),
Acid: 6-Chloro-1-dimethylcarbamoylmethyl-5-methyl-1H-indole-3-carboxylic acid,
ES-MS m/e (%): 468.3 (M+H$^+$).

Example 76

2-{6-Chloro-3-[4-(2,3-dihydro-benzofuran-7-yl)-piperidine-1-carbonyl]-indol-1-yl}-N-methyl-acetamide

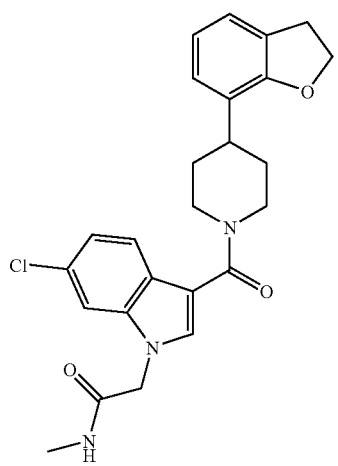

Following general procedure II, the alkylation of (6-chloro-1H-indol-3-yl)-[4-(2,3-dihydro-benzofuran-7-yl)-piperidin-1-yl]-methanone (preparation described herein), with (commercially available) 2-chloro-N-methyl-acetamide gave the title compound.
ES-MS m/e (%): 451.7 (M+H$^+$).

Example 77

N-(2-Amino-ethyl)-2-{6-chloro-3-[4-(2,3-dihydro-benzofuran-7-yl)-piperidine-1-carbonyl]-indol-1-yl}-acetamide

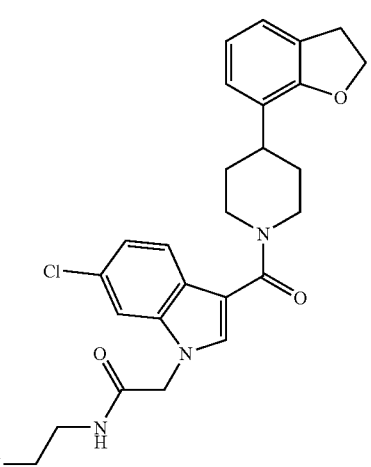

Analogous to general procedure I, the coupling of {6-chloro-3-[4-(2,3-dihydro-benzofuran-7-yl)-piperidine-1-carbonyl]-indol-1-yl}-acetic acid (prepared herein) with (commercially available) (2-amino-ethyl)-carbamic acid tert-butyl ester gave, after treatment with HCl and neutralisation, the title compound.
ES-MS m/e (%): 481.3 (M+H$^+$).

Example 78

2-{6-Chloro-3-[4-(2,3-dihydro-benzofuran-7-yl)-piperidine-1-carbonyl]-indol-1-yl}-acetamide

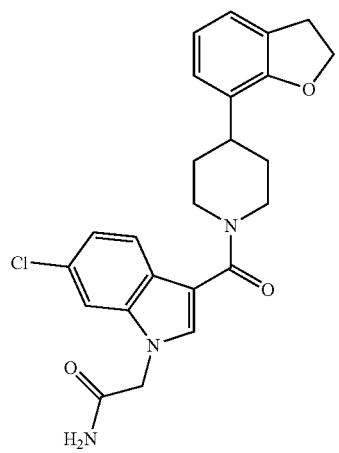

Analogous to general procedure I, the coupling of {6-chloro-3-[4-(2,3-dihydro-benzofuran-7-yl)-piperidine-1-carbonyl]-indol-1-yl}-acetic acid (prepared herein) with (commercially available) ammonia in THF, gave the title compound.
ES-MS m/e (%): 438.2 (M+H$^+$).

Example 79

2-{6-Chloro-3-[4-(2,3-dihydro-benzofuran-7-yl)-piperidine-1-carbonyl]-indol-1-yl}-N-(2-methylamino-ethyl)-acetamide

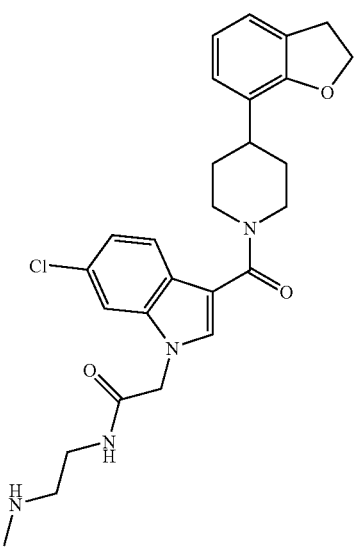

Analogous to general procedure I, the coupling of {6-chloro-3-[4-(2,3-dihydro-benzofuran-7-yl)-piperidine-1-carbonyl]-indol-1-yl}-acetic acid (prepared herein) with (commercially available) (2-amino-ethyl)-methyl-carbamic acid tert-butyl ester gave, after treatment with TFA and neutralisation, the title compound.
ES-MS m/e (%): 495.5 (M+H$^+$).

Example 80

2-{5,6-Dichloro-3-[4-(2-methoxy-phenyl)-piperidine-1-carbonyl]-indol-1-yl}-N,N-dimethyl-acetamide

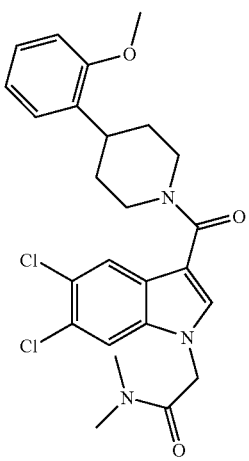

Amide coupling according to general procedure I:
Amine: 4-(2-Methoxy-phenyl)-piperidine (commercially available),
Acid: 5,6-Dichloro-1-dimethylcarbamoylmethyl-1H-indole-3-carboxylic acid,
ES-MS m/e (%): 488.5 (M+H$^+$).

Example 81

2-{6-Chloro-3-[4-(2,6-dimethoxy-phenyl)-piperidine-1-carbonyl]-indol-1-yl}-acetamide

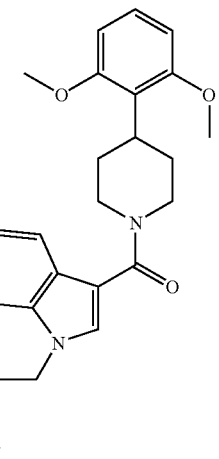

Analogous to general procedure I, the coupling of {6-chloro-3-[4-(2,6-dimethoxy-phenyl)-piperidine-1-carbonyl]-indol-1-yl}-acetic acid (prepared herein) with (commercially available) ammonia in THF gave the title compound.
ES-MS m/e (%): 456.2 (M+H$^+$).

Example 82

2-{6-Chloro-3-[4-(2,6-dimethoxy-phenyl)-piperidine-1-carbonyl]-indol-1-yl}-N-methyl-acetamide

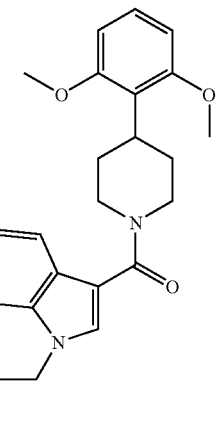

Analogous to general procedure II, the alkylation of (6-chloro-1H-indol-3-yl)-[4-(2,6-dimethoxy-phenyl)-piperidin-1-yl]-methanone (prepared herein) with (commercially available) 2-chloro-N-methyl-acetamide gave the title compound.
ES-MS m/e (%): 470.2 (M+H$^+$).

Example 83

2-{6-Chloro-3-[4-(2,6-dimethoxy-phenyl)-piperidine-1-carbonyl]-indol-1-yl}-N-(2-methylamino-ethyl)-acetamide

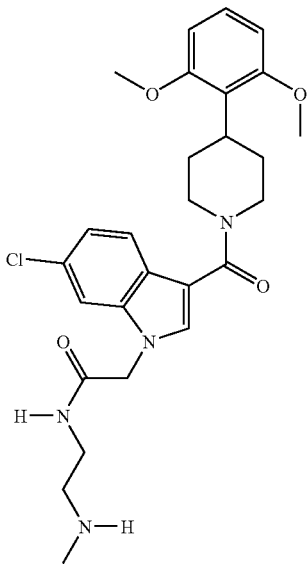

Analogous to general procedure I, the coupling of {6-chloro-3-[4-(2,6-dimethoxy-phenyl)-piperidine-1-carbonyl]-indol-1-yl}-acetic acid (prepared herein) with (commercially available) (2-amino-ethyl)-methyl-carbamic acid tert-butyl ester gave, after treatment with TFA and neutralisation, the title compound.

ES-MS m/e (%): 513.5 (M+H$^+$).

Example 84

N-(2-Amino-ethyl)-2-{6-chloro-3-[4-(2,6-dimethoxy-phenyl)-piperidine-1-carbonyl]-indol-1-yl}-acetamide

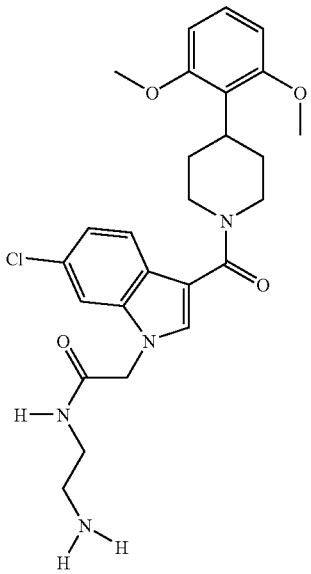

Analogous to general procedure I, the coupling of {6-chloro-3-[4-(2,6-dimethoxy-phenyl)-piperidine-1-carbonyl]-indol-1-yl}-acetic acid (prepared herein) with (commercially available) (2-amino-ethyl)-carbamic acid tert-butyl ester gave, after treatment with HCl and neutralisation, the title compound.

ES-MS m/e (%): 499.5 (M+H$^+$).

Example 85

(6-Chloro-1H-indol-3-yl)-[4-(2-trifluoromethoxy-phenyl)-piperidin-1-yl]-methanone 4-(2-Trifluoromethoxy-phenyl)-pyridine To a solution of (commercially available) (1-bromo-2-trifluoromethoxy-benzene) in DME (first degased with argon) under argon was added 3 mol % Pd(PPh$_3$)$_4$, pyridyl-4-boronic acid and 2N Na$_2$CO$_3$, the resulting reaction mixture was vigorously stirred under reflux. After 5 h at reflux, reaction as monitored by TLC showed completion. Two phases were separated, evaporation of most of the DME, redissolution of the residue in EtOAc and washing with aq. NaOH followed by evaporation gave a yellow oil. Flash Chromatography on SiO2 gel with a mixture of CH$_2$Cl$_2$/MeOH gave the title compound in 51% yield.

ES-MS m/e (%): 239.9 (M+H+).

1-Benzyl-4-(2-trifluoromethoxy-phenyl)-1,2,3,6-tetrahydro-pyridine

To a solution of 4-(2-trifluoromethoxy-phenyl)-pyridine in toluene was added (1 eq.) benzyl bromide, and reaction mixture was stirred under reflux for 2 h. Reaction was monitored by TLC (CH$_2$Cl$_2$/MeOH 95:5) and revealed total conversion to the first intermediate. Complete evaporation of solvent gave a white solid which was pure enough to carry out the next step. The white solid was dissolved in MeOH under argon and cooled down to 0° C., (4 eq.) NaBH$_4$ was added portion-wise (exothermic reaction). The reaction mixture was then stirred for 3 h at RT, reaction again monitored by TLC (CH$_2$Cl$_2$/MeOH 95:5) and revealed total conversion. Evaporation of MeOH, redissolution in CH$_2$Cl$_2$, and washing with 1N NaHCO$_3$ then brine, and evaporation, followed by SiO2 gel chromatography (CH$_2$Cl$_2$/MeOH) gave the title compound in 61% yield.

ES-MS m/e (%): 334.3 (M+H$^+$).

4-(2-Trifluoromethoxy-phenyl)-piperidine

To a solution of 1-benzyl-4-(2-trifluoromethoxy-phenyl)-1,2,3,6-tetrahydro-pyridine (described herein below) in EtOH was added (0.2 wt %) 10% Pd/C, followed by (5 eq.) TFA in a sealed tube. The reaction mixture was stirred at 50° C. under 3.0 bar of H$_2$ for 12 h. The reaction mixture was filtered over Celite and the filtrate evaporated down to dryness. Redissolution in EtOAc, washing with 1N NaHCO3 and concentration gave the crude product which was directly used for the next step.

ES-MS m/e (%): 246.6 (M+H⁺).

(6-Chloro-1H-indol-3-yl)-[4-(2-trifluoromethoxy-phenyl)-piperidin-1-yl]-methanone

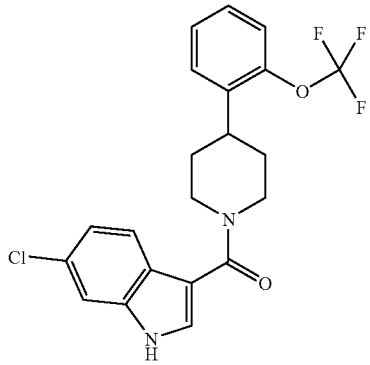

Following general procedure I, the coupling of 4-(2-trifluoromethoxy-phenyl)-piperidine with 6-chloro-1H-indole-3-carboxylic acid gave the title compound.

ES-MS m/e (%): 423.3 (M+H⁺).

Example 86

(6-Chloro-1H-indol-3-yl)-[4-(2-trifluoromethyl-phenyl)-piperidin-1-yl]-methanone

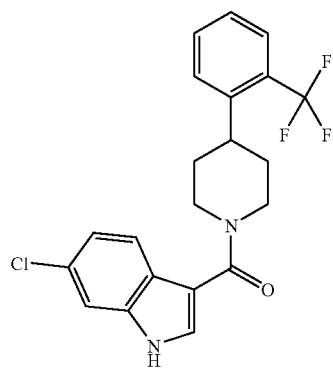

Following general procedure I, the coupling of (commercially available) 4-(2-trifluoromethyl-phenyl)-piperidine (described herein) with 6-chloro-1H-indole-3-carboxylic acid gave the title compound.

ES-MS m/e (%): 407.1 (M+H⁺).

Example 87

[6-Chloro-1-(2-dimethylamino-ethyl)-1H-indol-3-yl]-[4-(2,3-dihydro-benzofuran-7-yl)-piperidin-1-yl]-methanone

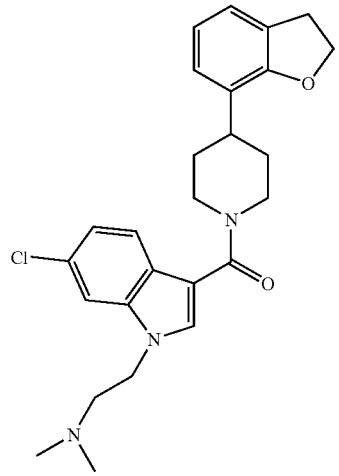

Analogous to general procedure II, the alkylation of (6-chloro-1H-indol-3-yl)-[4-(2,3-dihydro-benzofuran-7-yl)-piperidin-1-yl]-methanone (prepared herein) with (commercially available) (2-chloro-ethyl)-dimethyl-amine gave the title compound.

ES-MS m/e (%): 452.2 (M+H⁺).

Example 88

2-{6-Chloro-3-[4-(2-trifluoromethoxy-phenyl)-piperidine-1-carbonyl]-indol-1-yl}-1-(4-methyl-piperazin-1-yl)-ethanone

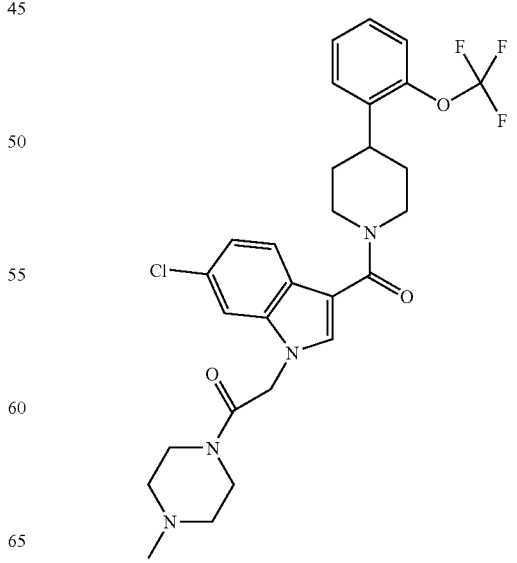

Following general procedure II, the alkylation of (6-chloro-1H-indol-3-yl)-[4-(2-trifluoromethoxy-phenyl)-piperidin-1-yl]-methanone (preparation described herein), with (commercially available) 2-chloro-1-(4-methyl-piperazin-1-yl)-ethanone gave the title compound.

ES-MS m/e (%): 563.3 (M+H$^+$).

Example 89

2-{6-Chloro-3-[4-(2-trifluoromethoxy-phenyl)-piperidine-1-carbonyl]-indol-1-yl}-N-(2-dimethylamino-ethyl)-acetamide {6-Chloro-3-[4-(2-trifluoromethoxy-phenyl)-piperidine-1-carbonyl]-indol-1-yl}-acetic acid Following general procedure II, the alkylation of (6-chloro-1H-indol-3-yl)-[4-(2-trifluoromethoxy-phenyl)-piperidin-1-yl]-methanone (preparation described herein), with (commercially available) bromo-acetic acid gave the title compound.

ES-MS m/e (%): 481.3 (M+H$^+$).

2-{6-Chloro-3-[4-(2-trifluoromethoxy-phenyl)-piperidine-1-carbonyl]-indol-1-yl}-N-(2-dimethylamino-ethyl)-acetamide

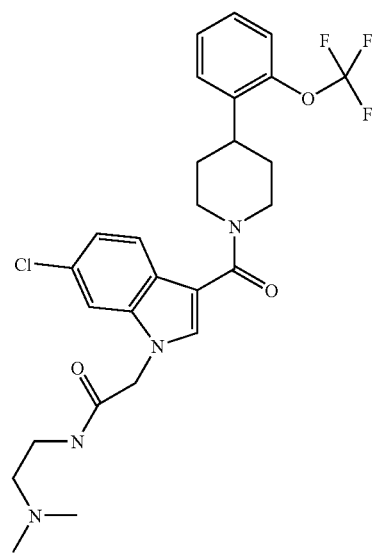

Analogous to general procedure I, the coupling of {6-chloro-3-[4-(2-trifluoromethoxy-phenyl)-piperidine-1-carbonyl]-indol-1-yl}-acetic acid (prepared herein) with (commercially available) N$^1$,N$^1$-dimethyl-ethane-1,2-diamine gave the title compound.

ES-MS m/e (%): 551.5 (M+H$^+$).

Example 90

2-{6-Chloro-3-[4-(2-trifluoromethoxy-phenyl)-piperidine-1-carbonyl]-indol-1-yl}-N-methyl-acetamide

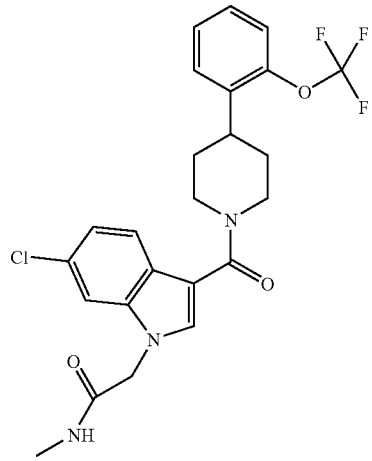

Analogous to general procedure I, the coupling of (6-chloro-1H-indol-3-yl)-[4-(2-trifluoromethoxy-phenyl)-piperidin-1-yl]-methanone (prepared herein) with (commercially available) 2-chloro-N-methyl-acetamide gave the title compound.

ES-MS m/e (%): 494.5 (M+H$^+$).

Example 91

2-{6-Chloro-3-[4-(2-trifluoromethoxy-phenyl)-piperidine-1-carbonyl]-indol-1-yl}-acetamide

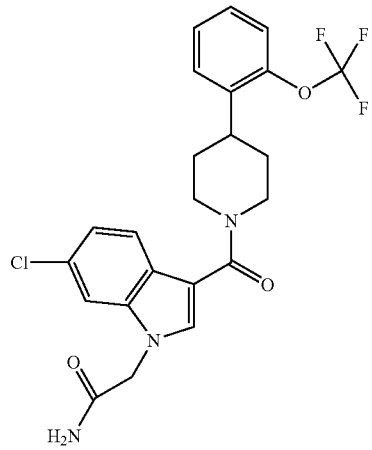

Analogous to general procedure I, the coupling of {6-chloro-3-[4-(2-trifluoromethoxy-phenyl)-piperidine-1-carbonyl]-indol-1-yl}-acetic acid (prepared herein) with (commercially available) ammonia in THF, gave the title compound.

ES-MS m/e (%): 480.3 (M+H$^+$).

Example 92

2-{6-Chloro-3-[4-(2-trifluoromethoxy-phenyl)-piperidine-1-carbonyl]-indol-1-yl}-1-piperazin-1-yl-ethanone

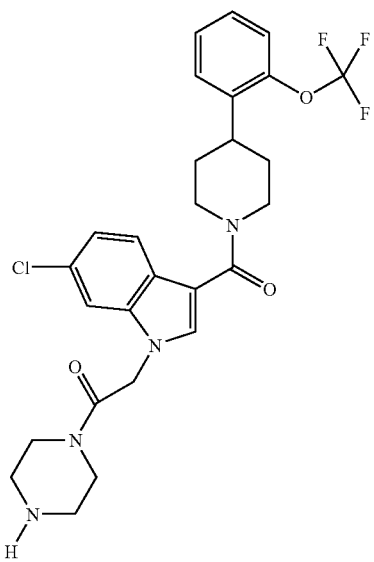

Analogous to general procedure I, the coupling of {6-chloro-3-[4-(2-trifluoromethoxy-phenyl)-piperidine-1-carbonyl]-indol-1-yl}-acetic acid (prepared described herein) with (commercially available) piperazine-1-carboxylic acid tert-butyl ester gave, after treatment with TFA and neutralisation, the title compound.

ES-MS m/e (%): 548.7 (M+H$^+$).

Example 93

2-{6-Chloro-3-[4-(2-trifluoromethoxy-phenyl)-piperidine-1-carbonyl]-indol-1-yl}-N-(2-methylamino-ethyl)-acetamide

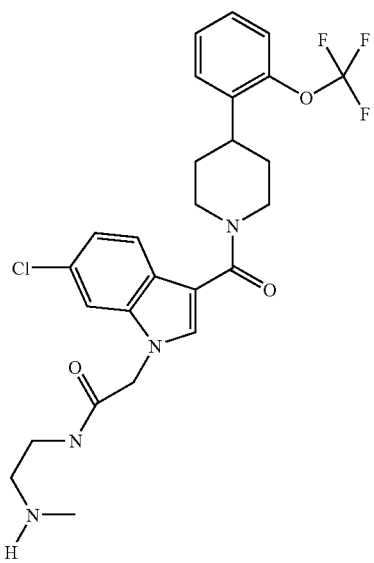

Analogous to general procedure I, the coupling of {6-chloro-3-[4-(2-trifluoromethoxy-phenyl)-piperidine-1-carbonyl]-indol-1-yl}-acetic acid (prepared described herein) with (commercially available) (2-amino-ethyl)-methyl-carbamic acid tert-butyl ester gave, after treatment with TFA and neutralisation, the title compound.

ES-MS m/e (%): 536.7 (M+H$^+$).

Example 94

N-(2-Amino-ethyl)-2-{6-chloro-3-[4-(2-trifluoromethoxy-phenyl)-piperidine-1-carbonyl]-indol-1-yl}-acetamide

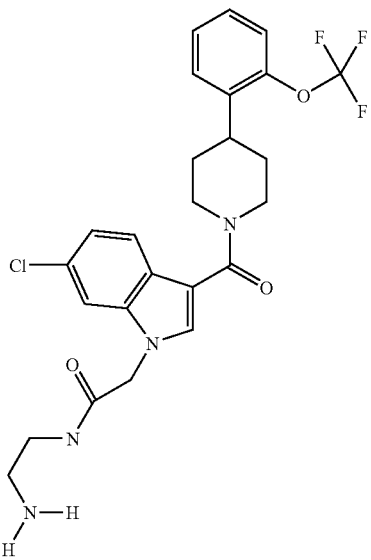

Analogous to general procedure I, the coupling of {6-chloro-3-[4-(2-trifluoromethoxy-phenyl)-piperidine-1-carbonyl]-indol-1-yl}-acetic acid (prepared described herein) with (commercially available) (2-amino-ethyl)-carbamic acid tert-butyl ester gave, after treatment with HCl and neutralisation, the title compound.

ES-MS m/e (%): 522.7 (M+H$^+$).

Example 95

2-{6-Chloro-3-[4-(2-trifluoromethoxy-phenyl)-piperidine-1-carbonyl]-indol-1-yl}-N,N-dimethyl-acetamide

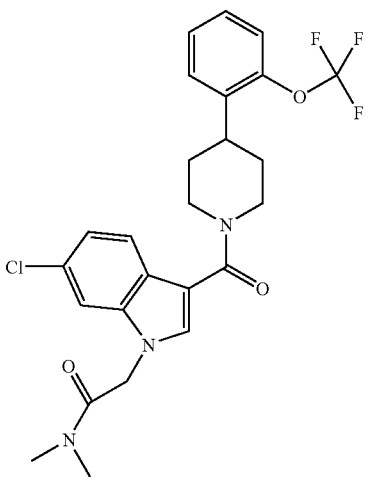

Analogous to general procedure II, the alkylation of (6-chloro-1H-indol-3-yl)-[4-(2-trifluoromethoxy-phenyl)- piperidin-1-yl]-methanone (prepared herein) with (commercially available) 2-chloro-N,N-dimethyl-acetamide gave the title compound.

ES-MS m/e (%): 508.4 (M+H⁺).

Example 96

2-{6-Chloro-3-[4-(2-trifluoromethyl-phenyl)-piperidine-1-carbonyl]-indol-1-yl}-N-methyl-acetamide

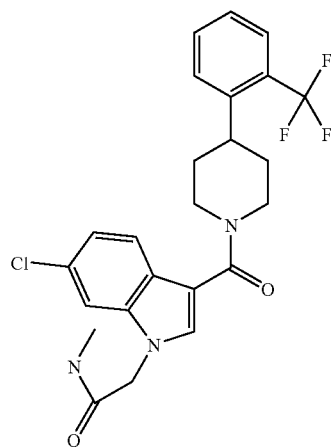

Analogous to general procedure II, the alkylation of (6-chloro-1H-indol-3-yl)-[4-(2-trifluoromethyl-phenyl)-piperidin-1-yl]-methanone (prepared herein) with (commercially available) 2-chloro-N-methyl-acetamide gave the title compound.

ES-MS m/e (%): 477.7 (M+H⁺).

Example 97

2-{6-Chloro-3-[4-(2-trifluoromethyl-phenyl)-piperidine-1-carbonyl]-indol-1-yl}-1-(4-methyl-piperazin-1-yl)-ethanone

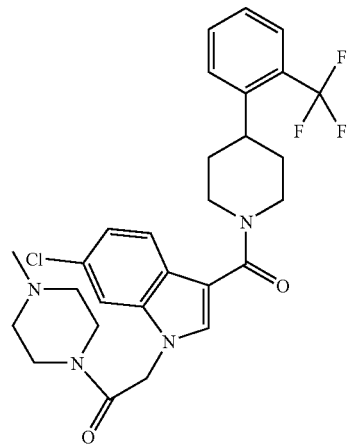

Analogous to general procedure II, the alkylation of (6-chloro-1H-indol-3-yl)-[4-(2-trifluoromethyl-phenyl)-piperidin-1-yl]-methanone (prepared herein) with (commercially available) 2-chloro-1-(4-methyl-piperazin-1-yl)-ethanone gave the title compound.

ES-MS m/e (%): 546.8 (M+H⁺).

Example 98

2-{6-Chloro-3-[4-(2-trifluoromethyl-phenyl)-piperidine-1-carbonyl]-indol-1-yl}-acetamide {6-Chloro-3-[4-(2-trifluoromethyl-phenyl)-piperidine-1-carbonyl]-indol-1-yl}-acetic acid Following general procedure II, the alkylation of (6-chloro-1H-indol-3-yl)-[4-(2-trifluoromethyl-phenyl)-piperidin-1-yl]-methanone (preparation described herein), with (commercially available) bromo-acetic acid gave the title compound.

ES-MS m/e (%): 481.3 (M+H⁺).

2-{6-Chloro-3-[4-(2-trifluoromethyl-phenyl)-piperidine-1-carbonyl]-indol-1-yl}-acetamide

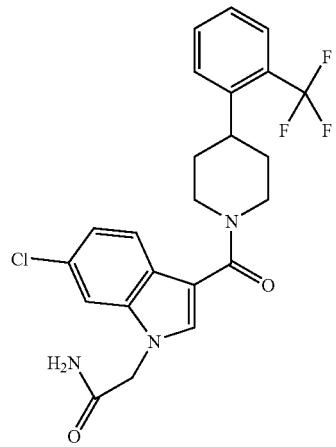

Analogous to general procedure I, the coupling of {6-chloro-3-[4-(2-trifluoromethyl-phenyl)-piperidine-1-carbonyl]-indol-1-yl}-acetic acid with (commercially available) ammonia in THF, gave the title compound.

ES-MS m/e (%): 464.6 (M+H⁺).

Example 99

2-{6-Chloro-3-[4-(2-trifluoromethyl-phenyl)-piperidine-1-carbonyl]-indol-1-yl}-1-piperazin-1-yl-ethanone hydrochloride

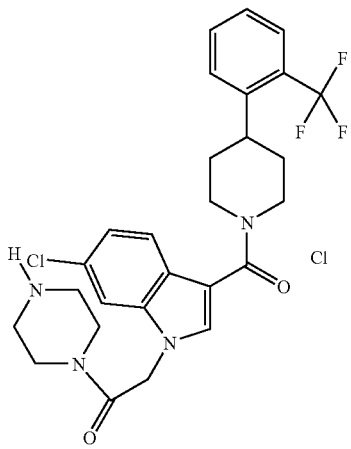

Analogous to general procedure I, the coupling of {6-chloro-3-[4-(2-trifluoromethyl-phenyl)-piperidine-1-carbonyl]-indol-1-yl}-acetic acid (prepared herein) with (commercially available) piperazine-1-carboxylic acid tert-butyl ester gave, after treatment with HCl, the title compound.

ES-MS m/e (%): 532.7 (M+H⁺).

Example 100

2-{6-Chloro-3-[4-(2-trifluoromethyl-phenyl)-piperidine-1-carbonyl]-indol-1-yl}-N-(2-methylamino-ethyl)-acetamide hydrochloride

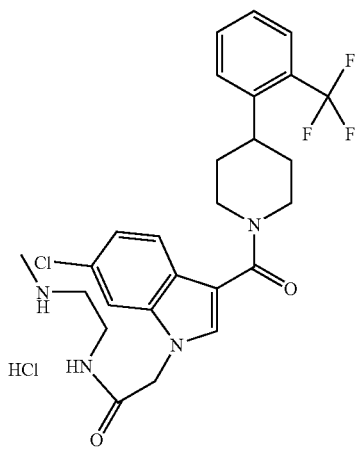

Analogous to general procedure I, the coupling of {6-chloro-3-[4-(2-trifluoromethyl-phenyl)-piperidine-1-carbonyl]-indol-1-yl}-acetic acid (prepared herein) with (commercially available) (2-amino-ethyl)-methyl-carbamic acid tert-butyl ester gave, after treatment with HCl the title compound.

ES-MS m/e (%): 521.3 (M+H⁺).

Example 101

N-(2-Amino-ethyl)-2-{6-chloro-3-[4-(2-trifluoromethyl-phenyl)-piperidine-1-carbonyl]-indol-1-yl}-acetamide hydrochloride

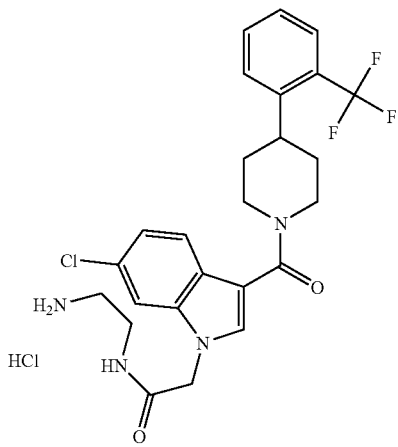

Analogous to general procedure I, the coupling of {6-chloro-3-[4-(2-trifluoromethyl-phenyl)-piperidine-1-carbonyl]-indol-1-yl}-acetic acid (prepared herein) with (commercially available) (2-amino-ethyl)-carbamic acid tert-butyl ester gave, after treatment with HCl, the title compound.

ES-MS m/e (%): 507.3 (M+H⁺).

Example 102

2-{6-Chloro-3-[4-(2-trifluoromethyl-phenyl)-piperidine-1-carbonyl]-indol-1-yl}-N,N-dimethyl-acetamide

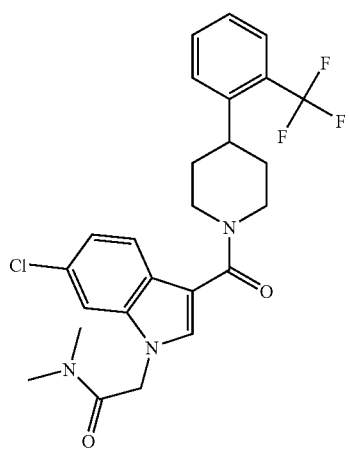

Analogous to general procedure I, the coupling of (6-chloro-1H-indol-3-yl)-[4-(2-trifluoromethyl-phenyl)-piperidin-1-yl]-methanone (prepared herein) with (commercially available) 2-chloro-N,N-dimethyl-acetamide gave the title compound.

ES-MS m/e (%): 491.7 (M+H⁺).

Example 103

N-(2-Amino-ethyl)-2-{6-chloro-3-[4-(2-trifluoromethyl-phenyl)-piperidine-1-carbonyl]-indol-1-yl}-acetamide hydrochloride

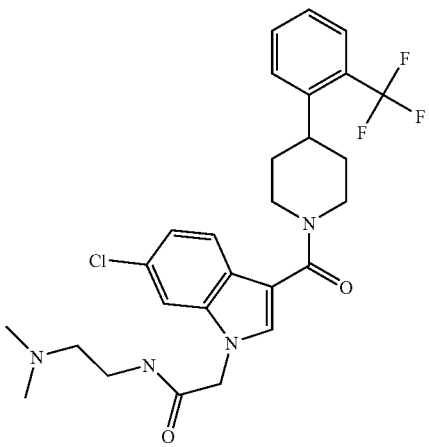

Analogous to general procedure I, the coupling of {6-chloro-3-[4-(2-trifluoromethyl-phenyl)-piperidine-1-carbonyl]-indol-1-yl}-acetic acid (prepared herein) with (commercially available) $N^1,N^1$-dimethyl-ethane-1,2-diamine, gave the title compound.

ES-MS m/e (%): 534.8 (M+H$^+$).

Example 104

[1-(2-Amino-ethyl)-6-chloro-1H-indol-3-yl]-[4-(2,3-dihydro-benzofuran-7-yl)-piperidin-1-yl]-methanone

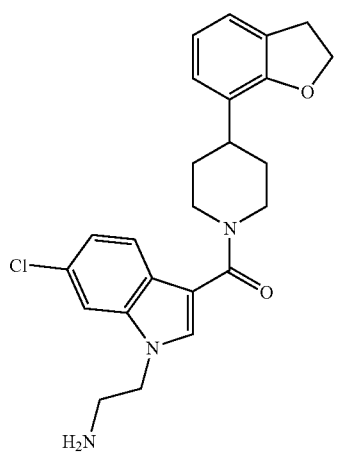

Following general procedure II, the alkylation of (6-chloro-1H-indol-3-yl)-[4-(2,3-dihydro-benzofuran-7-yl)-piperidin-1-yl]-methanone (preparation described herein), with (commercially available) 2-chloro-ethylamine gave the title compound.

ES-MS m/e (%): 424.5 (M+H$^+$).

Example 105

[1-(2-Amino-ethyl)-6-chloro-1H-indol-3-yl]-[4-(2-trifluoromethoxy-phenyl)-piperidin-1-yl]-methanone

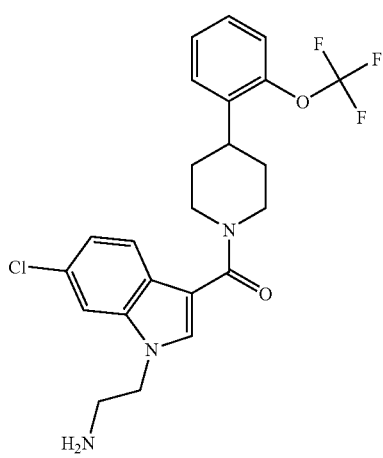

Analogous to general procedure II, the alkylation of (6-chloro-1H-indol-3-yl)-[4-(2-trifluoromethoxy-phenyl)-piperidin-1-yl]-methanone (prepared herein) with (commercially available) 2-chloro-ethylamine gave the title compound.

ES-MS m/e (%): 466.4 (M+H$^+$).

Example 106

2-{6-Chloro-3-[4-(2-methoxy-phenyl)-piperidine-1-carbonyl]-indol-1-yl}-N-methyl-acetamide

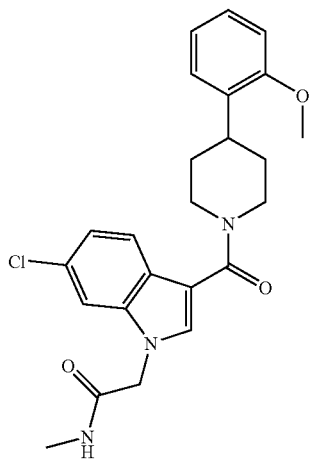

Following general procedure II, the alkylation of (6-Chloro-1H-indol-3-yl)-[4-(2-methoxy-phenyl)-piperidin-1-yl]-methanone (preparation described herein), with (commercially available) 2-chloro-N-methyl-acetamide gave the title compound.

ES-MS m/e (%): 440.4 (M+H$^+$).

Example 107

[6-Chloro-1-(2-methylamino-ethyl)-1H-indol-3-yl]-[4-(2,3-dihydro-benzofuran-7-yl)-piperidin-1-yl]-methanone

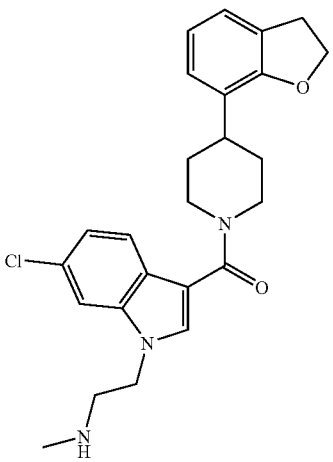

Following general procedure II, the alkylation of (6-chloro-1H-indol-3-yl)-[4-(2,3-dihydro-benzofuran-7-yl)-piperidin-1-yl]-methanone (preparation described herein), with (commercially available) (2-chloro-ethyl)-methyl-amine gave the title compound.

ES-MS m/e (%): 438.4 (M+H+).

Example 108

[6-Chloro-1-(2-dimethylamino-ethyl)-1H-indol-3-yl]-[4-(2-methoxy-phenyl)-piperidin-1-yl]-methanone

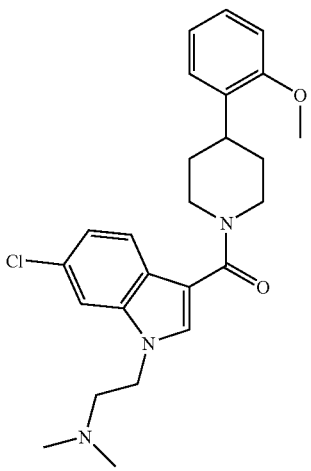

Following general procedure II, the alkylation of (6-chloro-1H-indol-3-yl)-[4-(2-methoxy-phenyl)-piperidin-1-yl]-methanone (preparation described herein), with (commercially available) (2-chloro-ethyl)-dimethyl-amine gave the title compound.

ES-MS m/e (%): 440.3 (M+H+).

Example 109

[6-Chloro-1-(2-methylamino-ethyl)-1H-indol-3-yl]-[4-(2-methoxy-phenyl)-piperidin-1-yl]-methanone

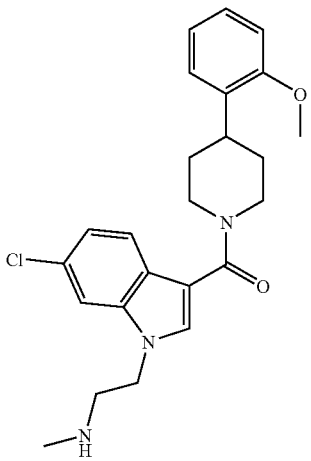

Following general procedure II, the alkylation of (6-chloro-1H-indol-3-yl)-[4-(2-methoxy-phenyl)-piperidin-1-yl]-methanone (preparation described herein), with (commercially available) (2-chloro-ethyl)-methyl-amine gave the title compound.

ES-MS m/e (%): 426.3 (M+H+).

Example 110

[1-(2-Amino-ethyl)-6-chloro-1H-indol-3-yl]-[4-(2-methoxy-phenyl)-piperidin-1-yl]-methanone

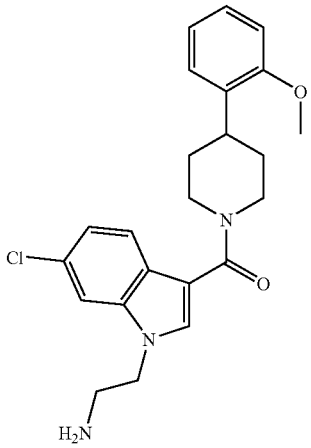

Following general procedure II, the alkylation of (6-chloro-1H-indol-3-yl)-[4-(2-methoxy-phenyl)-piperidin-1-yl]-methanone (preparation described herein), with (commercially available) 2-chloro-ethylamine gave the title compound.

ES-MS m/e (%): 412.3 (M+H+).

Example 111

2-{6-Chloro-3-[4-(2-fluoro-phenyl)-piperidine-1-carbonyl]-indol-1-yl}-N-methyl-acetamide (6-Chloro-1H-indol-3-yl)-[4-(2-fluoro-phenyl)-piperidin-1-yl]-methanone Following general procedure I, the coupling of (commercially available) 4-(2-fluoro-phenyl)-piperidine (described herein below) with 6-chloro-1H-indole-3-carboxylic acid gave the title compound.

ES-MS m/e (%): 357.3 (M+H+).

2-{6-Chloro-3-[4-(2-fluoro-phenyl)-piperidine-1-carbonyl]-indol-1-yl}-N-methyl-acetamide

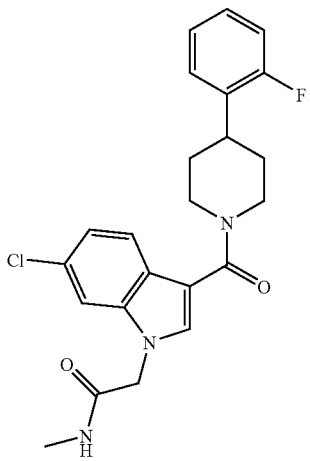

Following general procedure II, the alkylation of (6-chloro-1H-indol-3-yl)-[4-(2-fluoro-phenyl)-piperidin-1- yl]-methanone, with (commercially available) 2-chloro-N-methyl-acetamide gave the title compound.

ES-MS m/e (%): 428.2 (M+H$^+$).

Example 112

[1-(2-Amino-ethyl)-6-chloro-1H-indol-3-yl]-[4-(2-fluoro-phenyl)-piperidin-1-yl]-methanone

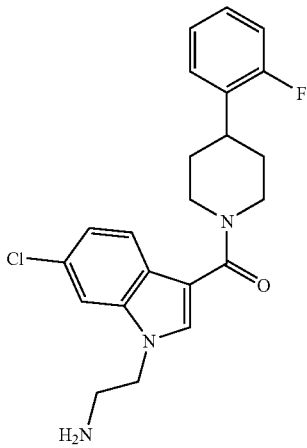

Following general procedure II, the alkylation of (6-chloro-1H-indol-3-yl)-[4-(2-fluoro-phenyl)-piperidin-1-yl]-methanone (preparation described herein), with (commercially available) 2-chloro-ethylamine gave the title compound.

ES-MS m/e (%): 400.1 (M+H$^+$).

Example 113

2-{6-Chloro-3-[4-(2-fluoro-phenyl)-piperidine-1-carbonyl]-indol-1-yl}-acetamide

{6-Chloro-3-[4-(2-fluoro-phenyl)-piperidine-1-carbonyl]-indol-1-yl}-acetic acid

Following general procedure II, the alkylation of (6-chloro-1H-indol-3-yl)-[4-(2-fluoro-phenyl)-piperidin-1-yl]-methanone (preparation described herein), with (commercially available) bromo-acetic acid gave the title compound.

ES-MS m/e (%): 413.0 (M−H$^+$).

2-{6-Chloro-3-[4-(2-fluoro-phenyl)-piperidine-1-carbonyl]-indol-1-yl}-acetamide

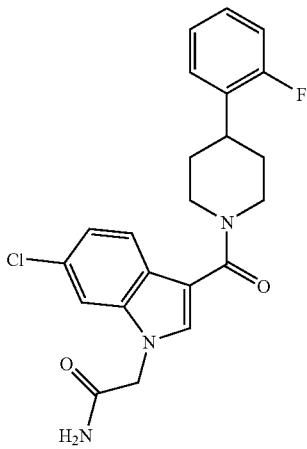

Following general procedure I, the coupling of {6-chloro-3-[4-(2-fluoro-phenyl)-piperidine-1-carbonyl]-indol-1-yl}-acetic acid, with (commercially available) ammonia in THF gave the title compound.

ES-MS m/e (%): 414.2 (M+H$^+$).

Example 114

2-{6-Chloro-3-[4-(2-fluoro-phenyl)-piperidine-1-carbonyl]-indol-1-yl}-N,N-dimethyl-acetamide

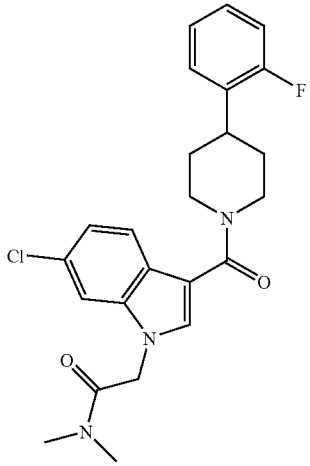

Following general procedure II, the alkylation of (6-chloro-1H-indol-3-yl)-[4-(2-fluoro-phenyl)-piperidin-1-yl]-methanone (preparation described herein below), with (commercially available) 2-chloro-N,N-dimethyl-acetamide gave the title compound. ES-MS m/e (%): 442.3 (M+H$^+$).

Example 115

[6-Chloro-1-(2-dimethylamino-ethyl)-1H-indol-3-yl]-[4-(2-fluoro-phenyl)-piperidin-1-yl]-methanone

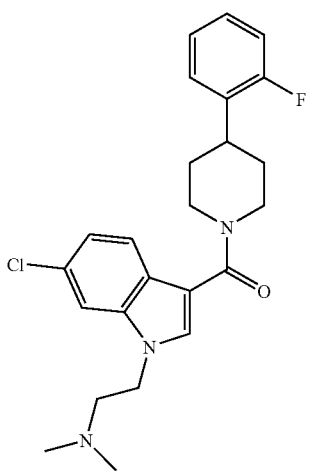

Following general procedure II, the alkylation of (6-chloro-1H-indol-3-yl)-[4-(2-fluoro-phenyl)-piperidin-1-yl]-methanone (preparation described herein), with (commercially available) (2-chloro-ethyl)-dimethyl-amine gave the title compound.

ES-MS m/e (%): 428.2 (M+H$^+$).

Example 116

2-{6-Chloro-3-[4-(2-fluoro-phenyl)-piperidine-1-carbonyl]-indol-1-yl}-1-(4-methyl-piperazin-1-yl)-ethanone

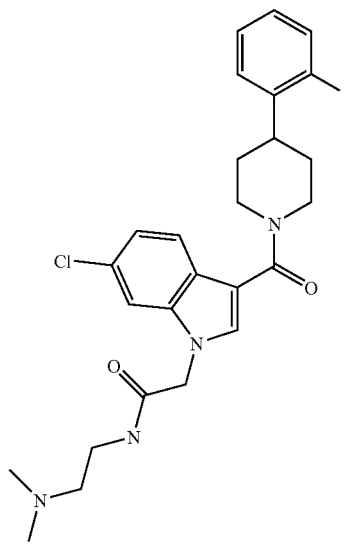

Following general procedure I, the coupling of {6-chloro-3-[4-(2-fluoro-phenyl)-piperidine-1-carbonyl]-indol-1-yl}-acetic acid (preparation described herein), with (commercially available) $N^1,N^1$-dimethyl-ethane-1,2-diamine gave the title compound.

ES-MS m/e (%): 485.2 (M+H$^+$).

Example 117

2-{6-Chloro-3-[4-(2-fluoro-phenyl)-piperidine-1-carbonyl]-indol-1-yl}-1-(4-methyl-piperazin-1-yl)-ethanone

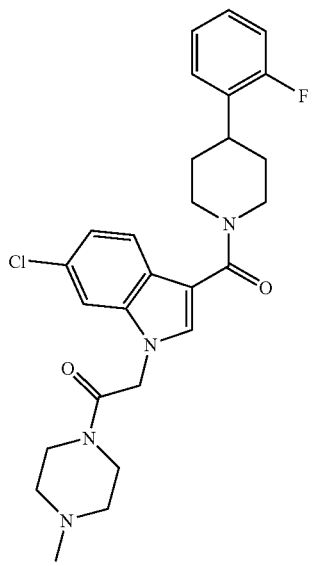

Following general procedure II, the alkylation of (6-chloro-1H-indol-3-yl)-[4-(2-fluoro-phenyl)-piperidin-1-yl]-methanone (preparation described herein), with (commercially available) 2-chloro-1-(4-methyl-piperazin-1-yl)-ethanone gave the title compound.

ES-MS m/e (%): 497.2 (M+H$^+$).

Example 118

2-{6-Chloro-3-[4-(2-fluoro-phenyl)-piperidine-1-carbonyl]-indol-1-yl}-1-piperazin-1-yl-ethanone hydrochloride

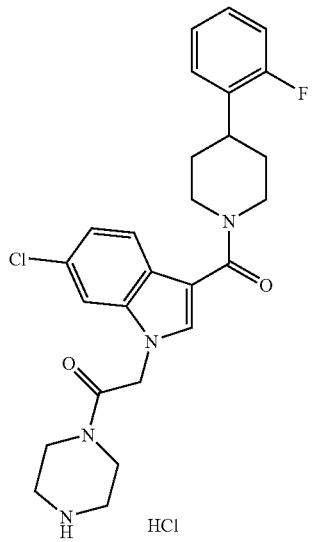

Following general procedure I, the coupling of {6-chloro-3-[4-(2-fluoro-phenyl)-piperidine-1-carbonyl]-indol-1-yl}-acetic acid (preparation described herein), with (commercially available) piperazine-1-carboxylic acid tert-butyl ester gave, after treatment with HCl, gave the title compound.

ES-MS m/e (%): 483.2 (M+H$^+$).

Example 119

2-{6-Chloro-3-[4-(2-fluoro-phenyl)-piperidine-1-carbonyl]-indol-1-yl}-N-(2-methylamino-ethyl)-acetamide hydrochloride

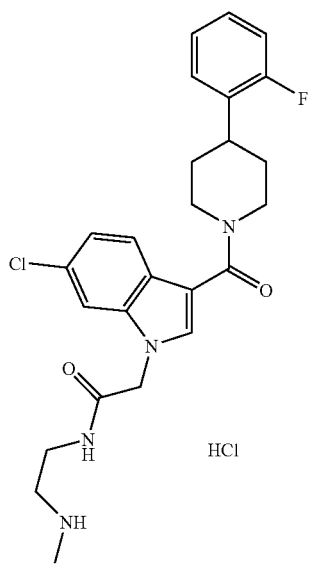

Following general procedure I, the coupling of {6-chloro-3-[4-(2-fluoro-phenyl)-piperidine-1-carbonyl]-indol-1-yl}-acetic acid (preparation described herein), with (commercially available) (2-amino-ethyl)-methyl-carbamic acid tert-butyl ester gave, after treatment with HCl, the title compound.

ES-MS m/e (%): 471.2 (M+H⁺).

Example 120

N-(2-Amino-ethyl)-2-{6-chloro-3-[4-(2-fluoro-phenyl)-piperidine-1-carbonyl]-indol-1-yl}-acetamide hydrochloride

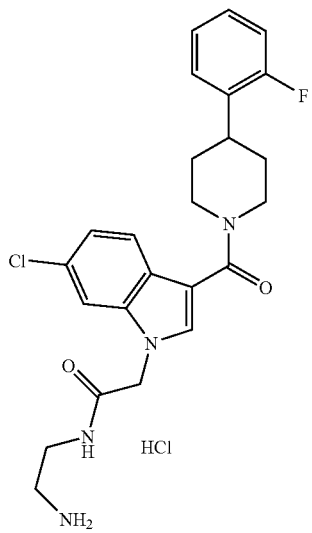

Following general procedure I, the coupling of {6-chloro-3-[4-(2-fluoro-phenyl)-piperidine-1-carbonyl]-indol-1-yl}-acetic acid (preparation described herein), with (commercially available) (2-amino-ethyl)-carbamic acid tert-butyl ester gave, after treatment with HCl the title compound.

ES-MS m/e (%): 457.2 (M+H⁺).

Example 121

(6-Chloro-1H-indol-3-yl)-(3,4,5,6-tetrahydro-2H-[4,4']bipyridinyl-1-yl)-methanone

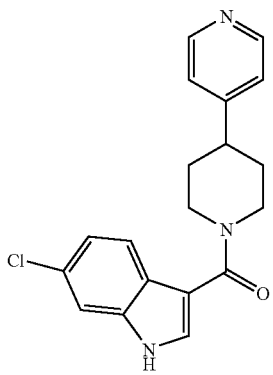

Following general procedure I, the coupling of (commercially available) 1,2,3,4,5,6-hexahydro-[4,4']bipyridinyl with 6-chloro-1H-indole-3-carboxylic acid gave the title compound.

ES-MS m/e (%): 340.1 (M+H⁺).

Example 122

2-[6-Chloro-3-(3,4,5,6-tetrahydro-2H-[4,4']bipyridinyl-1-carbonyl)-indol-1-yl]-N,N-dimethyl-acetamide

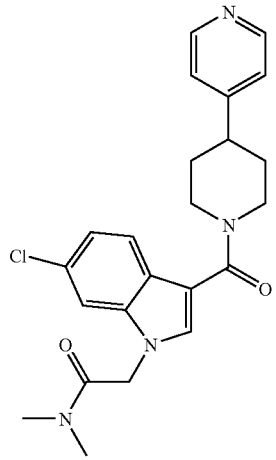

Following general procedure I, the coupling of (commercially available) 1,2,3,4,5,6-hexahydro-[4,4']bipyridinyl with 6-chloro-1-dimethylcarbamoylmethyl-1H-indole-3-carboxylic acid gave the title compound.

ES-MS m/e (%): 425.2 (M+H⁺).

Example 123

(6-Chloro-2-methyl-1H-indol-3-yl)-[4-(2-methoxy-phenyl)-piperidin-1-yl]-methanone

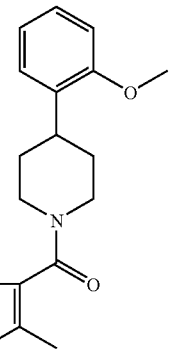

To a solution of 0.040 g (0.19 mmol) 6-chloro-2-methyl-1H-indole-3-carboxylic acid, 0.069 ml (0.40 mmol) N,N-diisopropylethylamine and 0.061 g (0.19 mmol) 2-(1H-benzotriazole-1-yl)-1,1,3,3-tetramethyluronium tetrafluoroborate in 1 ml dry N,N-dimethylformamide were added 0.038 g (0.20 mmol) 4-(2-methoxy-phenyl)-piperidine at room temperature. After stirring for 1 h the reaction mixture was quenched with 0.5 M aqueous sodium hydroxide solution (20 ml) and extracted with ethyl acetate (2×30 ml). The combined organic layers were washed with water (2×30 ml) and brine (1×30 ml), dried over sodium sulfate and concentrated in vacuo. The residue was purified by flash chromatography (n-heptane/ethyl acetate) to give the title compound (0.050 g; 69%) as a white solid.

MS m/e (%): 381 (M−H⁺, 100).

Example 124

(6-Chloro-1-methanesulfonyl-1H-indol-3-yl)-[4-(2-methoxy-phenyl)-piperidin-1-yl]-methanone

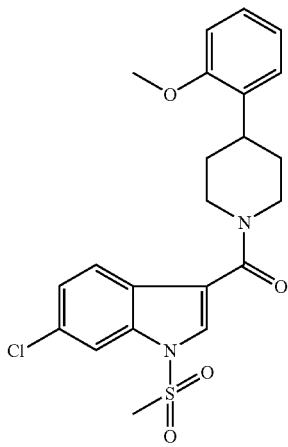

To a solution of 0.035 g (0.09 mmol) (6-chloro-1H-indol-3-yl)-[4-(2-methoxy-phenyl)-piperidin-1-yl]-methanone in 2 ml N,N-dimethylformamide were added 0.005 g (0.10 mmol) sodium hydride (50% in oil). After 45', 0.008 ml (0.10 mmol) methanesulfonyl chloride were added. The reaction mixture was quenched with water after 3 h and extracted with ethyl acetate (2×50 ml). The combined organic layers were washed with water (2×30 ml) and brine (1×30), dried over sodium sulfate and concentrated to dryness. The residue was chromatographed (loaded as a solution in toluene; Flashpac 5 g; n-heptane/ethyl acetate 100:0→75:25) to give the title compound (0.007 g; 17%) as a light yellow solid.

MS m/e (%): 447 (M+H$^+$, 100).

Example 125

2-{6-Chloro-3-[4-(5-fluoro-benzo[d]isoxazol-3-yl)-piperidine-1-carbonyl]-indol-1-yl}-N-methyl-acetamide

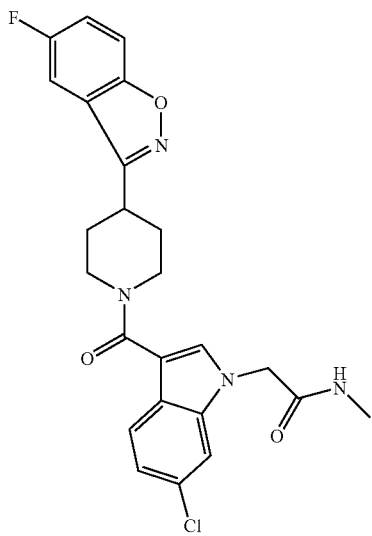

Following general procedure I, the coupling of (commercially available) 5-fluoro-3-piperidin-4-yl-benzo[d]isox- azole with 6-chloro-1-methylcarbamoylmethyl-1H-indole-3-carboxylic acid (prepared as described herein) gave the title compound.

ES-MS m/e (%): 469.1 (M+H$^+$).

Example 126

2-{6-Chloro-3-[4-(2-fluoro-phenyl)-4-hydroxy-piperidine-1-carbonyl]-indol-1-yl}-N-methyl-acetamide

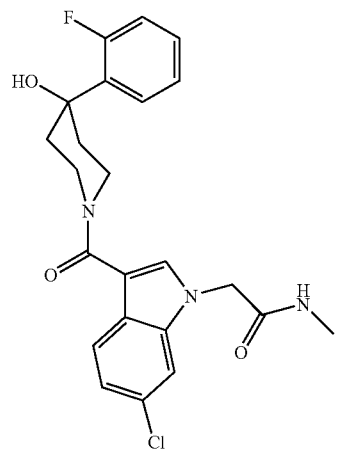

Following general procedure I, the coupling of 4-(2-fluoro-phenyl)-piperidin-4-ol (described in WO 2005118587) with 6-chloro-1-methylcarbamoylmethyl-1H-indole-3-carboxylic acid (prepared as described herein) gave the title compound.

ES-MS m/e (%): 444.1 (M+H$^+$).

Example 127

2-[6-Chloro-3-(3,4,5,6-tetrahydro-2H-[4,4']bipyridinyl-1-carbonyl)-indol-1-yl]-N-methyl-acetamide

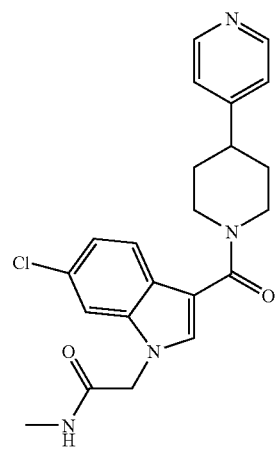

Following general procedure I, the coupling of (commercially available) 1,2,3,4,5,6-hexahydro-[4,4']bipyridinyl with 6-chloro-1-methylcarbamoylmethyl-1H-indole-3-carboxylic acid (prepared as described herein) gave the title compound.

ES-MS m/e (%): 411.2 (M+H$^+$).

Example 128

10-[4-(2-Methoxy-phenyl)-piperidine-1-carbonyl]-3,4-dihydro-1H-pyrazino[1,2-a]indole-2-carboxylic acid tert-butyl ester

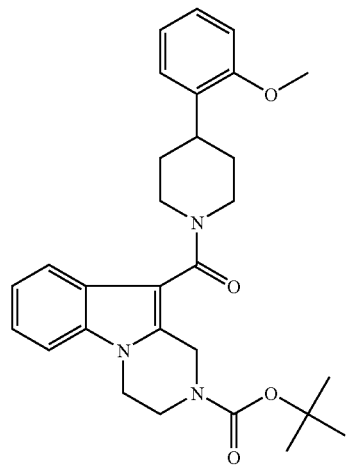

To a solution of 0.10 g (0.32 mmol) 3,4-dihydro-1H-pyrazino[1,2-a]indole-2,10-dicarboxylic acid 2-tert-butyl ester, 0.067 g (0.35 mmol) 4-(2-methoxyphenyl)-piperidine and 0.051 g (0.38 mmol) 1-hydroxybenzotriazole in 3.5 ml N,N-dimethylformamide were added 0.073 g (0.38 mmol) N-(3-dimethylaminopropyl)-N'-ethylcarbodiimide hydrochloride at room temperature. After stirring for 3 h the reaction mixture was diluted with saturated aqueous ammonium chloride solution and extracted with tert-butyl methyl ether (2×50 ml). The combined organic layers were washed with 1 M sodium hydroxide solution (1×30 ml) and water (1×30 ml), dried over sodium sulfate, concentrated in vacuo and purified by flash-chromatography (aminopropyl-modified silica gel, n-heptane/ethyl acetate) to give the title compound (0.087 g, 56%) as a light yellow solid.

MS m/e (%): 490 (M+H$^+$, 47).

Example 129

[4-(2-Methoxy-phenyl)-piperidin-1-yl]-(1,2,3,4-tetrahydro-pyrazino[1,2-a]indol-10-yl)-methanone hydrochloride

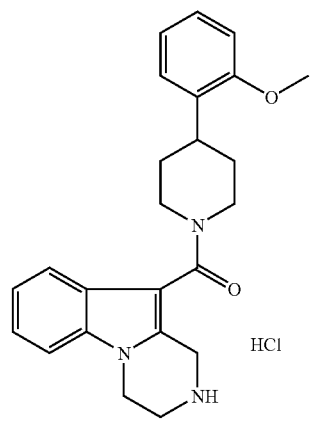

A mixture of 0.085 g (0.17 mmol) 10-[4-(2-methoxy-phenyl)-piperidine-1-carbonyl]-3,4-dihydro-1H-pyrazino[1,2-a]indole-2-carboxylic acid tert-butyl ester and 1.4 ml of a 1.25 M solution of hydrochloric acid (1.7 mmol) in methanol was stirred for 15 min at 50° C. The reaction mixture was concentrated in vacuo to give the title compound (0.072 g, 97%) as a light yellow solid.

MS m/e (%): 390 (M+H$^+$, 100).

Example 130

[4-(2-Methoxy-phenyl)-piperidin-1-yl]-(2-methyl-1,2,3,4-tetrahydro-pyrazino[1,2-a]indol-10-yl)-methanone

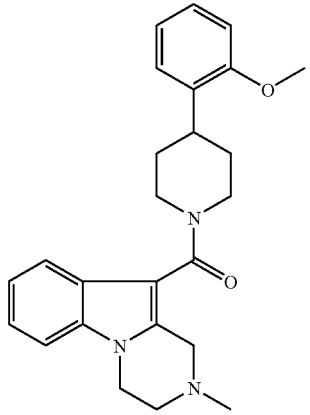

A solution of 0.040 g (0.094 mmol) [4-(2-methoxy-phenyl)-piperidin-1-yl]-(1,2,3,4-tetrahydro-pyrazino[1,2-a]indol-10-yl)-methanone hydrochloride, 0.026 ml (0.19 mmol) triethylamine and 0.023 g (0.77 mmol) paraformaldehyde in 2 ml methanol was heated at reflux for 1 h. The reaction mixture was cooled to 0° C. on an ice-water bath and treated with 0.0089 g (0.14 mmol) sodium cyanoborohydride. After completed addition the mixture was allowed to warm to room temperature and stirred for 2 h. Quenching with water and dilution with 2 M aqueous sodium carbonate solution was followed by extraction with dichloromethane (2×50 ml). The combined organic layers were dried over sodium sulfate, concentrated in vacuo and purified by flash-chromatography (aminopropyl-modified silica gel, n-heptane/ethyl acetate) to give the title compound (0.031 g, 82%) as an off-white solid.

MS m/e (%): 404 (M+H$^+$, 100).

Examples of Compounds of Formula I-c

Example 131

Benzyl-2-methyl-1H-indol-3-yl)-(4-phenyl-piperazin-1-yl)-methanone

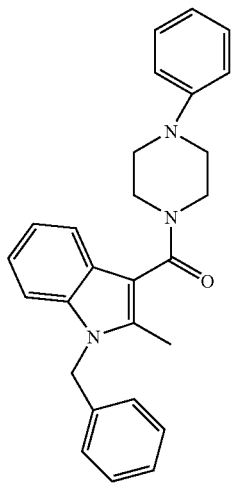

Amide coupling according to general procedure I:
Amine: 1-Phenyl-piperazine (commercially available),
Acid: 1-Benzyl-2-methyl-1H-indole-3-carboxylic acid,
ES-MS m/e (%): 410.6 (M+H⁺).

Example 132

Benzyl-2-methyl-1H-indol-3-yl)-[4-(2-methoxy-phenyl)-piperazin-1-yl]-methanone

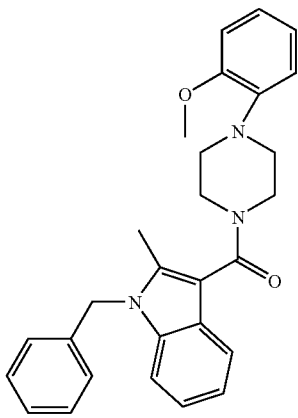

Amide coupling according to general procedure I:
Amine: 1-(2-Methoxy-phenyl)-piperazine (commercially available),
Acid: 1-Benzyl-2-methyl-1H-indole-3-carboxylic acid,
ES-MS m/e (%): 440.6 (M+H⁺).

Example 133

Benzyl-2-methyl-1H-indol-3-yl)-[4-(4-methoxy-phenyl)-piperazin-1-yl]-methanone

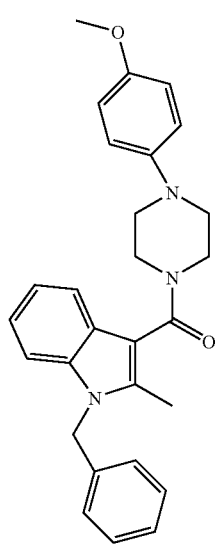

Amide coupling according to general procedure I:
Amine: 1-(4-Methoxy-phenyl)-piperazine (commercially available),
Acid: 1-Benzyl-2-methyl-1H-indole-3-carboxylic acid,
ES-MS m/e (%): 440.6 (M+H⁺).

Example 134

Benzyl-2-methyl-1H-indol-3-yl)-[4-(2-chloro-phenyl)-piperazin-1-yl]-methanone

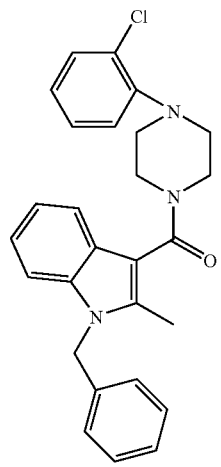

Amide coupling according to general procedure I:
Amine: 1-(2-Chloro-phenyl)-piperazine (commercially available),
Acid: 1-Benzyl-2-methyl-1H-indole-3-carboxylic acid,
ES-MS m/e (%): 444.5 (M+H⁺).

Example 135

Benzyl-2-methyl-1H-indol-3-yl)-[4-(4-chloro-phenyl)-piperazin-1-yl]-methanone

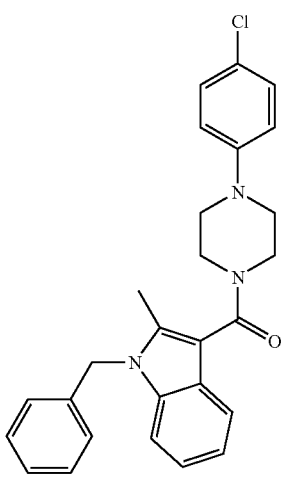

Amide coupling according to general procedure I:
Amine: 1-(4-Chloro-phenyl)-piperazine (commercially available),
Acid: 1-Benzyl-2-methyl-1H-indole-3-carboxylic acid,
ES-MS m/e (%): 444.5 (M+H⁺).

Example 136

(6-Chloro-1H-indol-3-yl)-(4-phenyl-piperazin-1-yl)-methanone

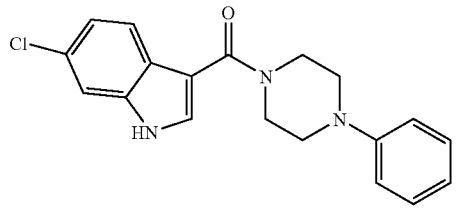

Amide coupling according to general procedure I:
Amine: 1-Phenyl-piperazine (commercially available),
Acid: 6-chloro-1H-indole-3-carboxylic acid,
ES-MS m/e (%): 340.4 (M+H$^+$).

Example 137

(6-Chloro-1H-indol-3-yl)-[4-(2-chloro-6-nitro-phenyl)-piperazin-1-yl]-methanone

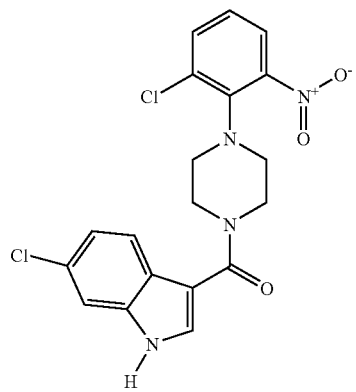

Following general procedure I, the coupling of (commercially available) 1-(2-chloro-6-nitro-phenyl)-piperazine with 6-chloro-1H-indole-3-carboxylic acid gave the title compound.
ES-MS m/e (%): 419.4 (M+H$^+$).

Example 138

(6-Chloro-1H-indol-3-yl)-[4-(2,6-dichloro-phenyl)-piperazin-1-yl]-methanone

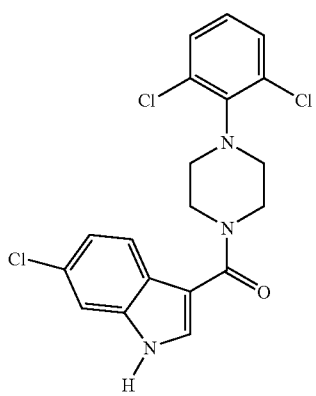

Following general procedure I, the coupling of (commercially available) 1-(2,6-dichloro-phenyl)-piperazine with 6-chloro-1H-indole-3-carboxylic acid gave the title compound.
ES-MS m/e (%): 408.4 (M+H$^+$).

Example 139

(6-Chloro-1H-indol-3-yl)-[4-(2,3-dihydro-benzo[1,4]dioxin-5-yl)-piperazin-1-yl]-methanone

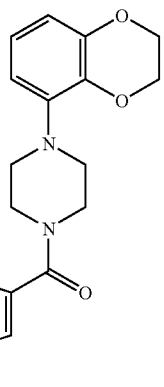

Following general procedure I, the coupling of (commercially available) 1-(2,3-dihydro-benzo[1,4]dioxin-5-yl)-piperazine with 6-chloro-1H-indole-3-carboxylic acid gave the title compound.
ES-MS m/e (%): 398.4 (M+H$^+$).

Example 140

(6-Chloro-1H-indol-3-yl)-[4-(2-nitro-4-trifluoromethyl-phenyl)-piperazin-1-yl]-methanone

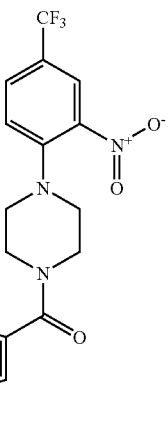

Following general procedure I, the coupling of (commercially available) 1-(2-nitro-4-trifluoromethyl-phenyl)-piperazine with 6-chloro-1H-indole-3-carboxylic acid gave the title compound.
ES-MS m/e (%): 453.4 (M+H$^+$).

Example 141

(6-Chloro-1H-indol-3-yl)-[4-(2-chloro-phenyl)-piperazin-1-yl]-methanone

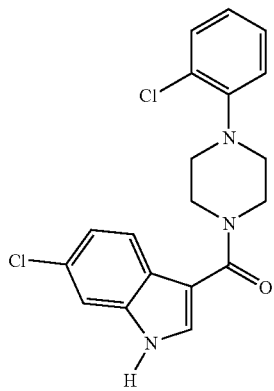

Following general procedure I, the coupling of (commercially available) 1-(2-chloro-phenyl)-piperazine, with 6-chloro-1H-indole-3-carboxylic acid gave the title compound ES-MS m/e (%): 374.4 (M+H$^+$).

Example 142

[4-(2-Amino-6-chloro-phenyl)-piperazin-1-yl]-(6-chloro-1H-indol-3-yl)-methanone

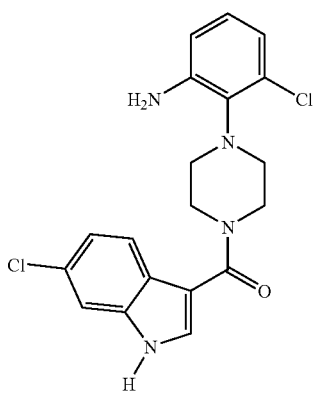

Following general procedure I, the coupling of 3-chloro-2-piperazin-1-yl-phenylamine (described in Tetrahedron Letters (2001), 42(9), 1645-1646), with 6-chloro-1H-indole-3-carboxylic acid gave the title compound ES-MS m/e (%): 389.4 (M+H$^+$).

Example 143

(6-Chloro-1H-indol-3-yl)-[4-(4-methoxy-phenyl)-piperazin-1-yl]-methanone

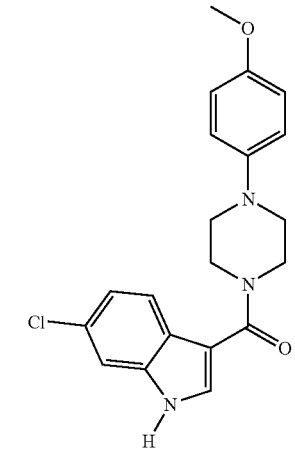

Following general procedure I, the coupling of (commercially available) 1-(4-methoxy-phenyl)-piperazine with 6-chloro-1H-indole-3-carboxylic acid gave the title compound ES-MS m/e (%): 370.4 (M+H$^+$).

Example 144

(6-Chloro-1H-indol-3-yl)-[4-(3-methoxy-phenyl)-piperazin-1-yl]-methanone

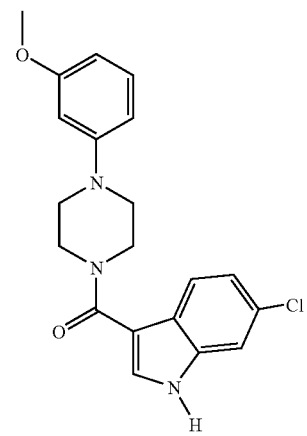

Following general procedure I, the coupling of (commercially available) 1-(3-methoxy-phenyl)-piperazine with 6-chloro-1H-indole-3-carboxylic acid gave the title compound ES-MS m/e (%): 370.4 (M+H$^+$).

Example 145

(6-Chloro-1H-indol-3-yl)-[4-(2-nitro-phenyl)-piperazin-1-yl]-methanone

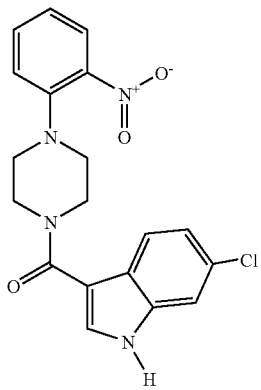

Following general procedure I, the coupling of (commercially available) 1-(2-nitro-phenyl)-piperazine with 6-chloro-1H-indole-3-carboxylic acid gave the title compound.

ES-MS m/e (%): 385.4 (M+H$^+$).

Example 146

(6-Chloro-1H-indol-3-yl)-[4-(2-methoxy-phenyl)-piperazin-1-yl]-methanone

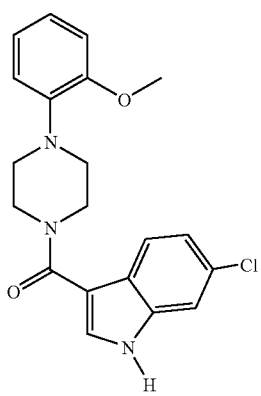

Following general procedure I, the coupling of (commercially available) 1-(2-methoxy-phenyl)-piperazine with 6-chloro-1H-indole-3-carboxylic acid gave the title compound.

ES-MS m/e (%): 370.4 (M+H$^+$).

Example 147

(6-Chloro-1H-indol-3-yl)-[4-(4-fluoro-phenyl)-piperazin-1-yl]-methanone

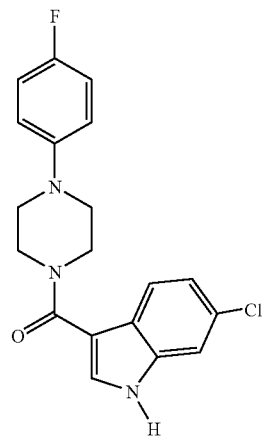

Following general procedure I, the coupling of (commercially available) 1-(4-fluoro-phenyl)-piperazine with 6-chloro-1H-indole-3-carboxylic acid gave the title compound ES-MS m/e (%): 358.4 (M+H$^+$).

Example 148

(6-Chloro-1H-indol-3-yl)-[4-(3-fluoro-phenyl)-piperazin-1-yl]-methanone

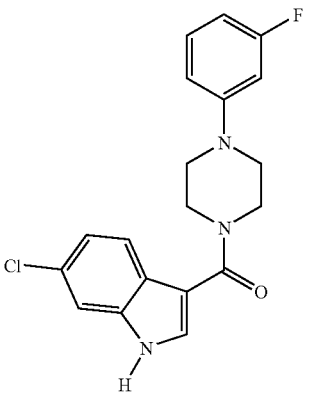

Following general procedure I, the coupling of (commercially available) 1-(3-fluoro-phenyl)-piperazine with 6-chloro-1H-indole-3-carboxylic acid gave the title compound.

ES-MS m/e (%): 358.4 (M+H$^+$).

Example 149

Chloro-4-[4-(6-chloro-1H-indole-3-carbonyl)-piperazin-1-yl]-benzonitrile

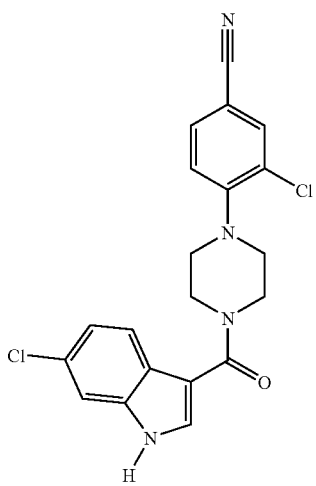

Following general procedure I, the coupling of (commercially available) 3-chloro-4-piperazin-1-yl-benzonitrile with 6-chloro-1H-indole-3-carboxylic acid gave the title compound ES-MS m/e (%): 399.4 (M+H$^+$).

Example 150

(6-Chloro-1H-indol-3-yl)-[4-(2-ethoxy-phenyl)-piperazin-1-yl]-methanone

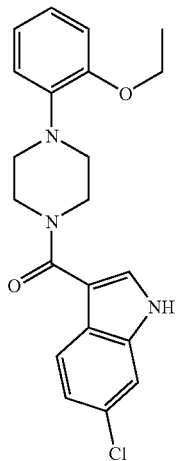

Amide coupling according to general procedure I:
Amine: 1-(2-Ethoxy-phenyl)-piperazine (commercially available),
Acid: 6-Chloro-1H-indole-3-carboxylic acid,
ES-MS m/e (%): 384.0 (M+H$^+$).

Example 151

2-{6-Chloro-3-[4-(2-methoxy-phenyl)-piperazine-1-carbonyl]-indol-1-yl}-N,N-dimethyl-acetamide

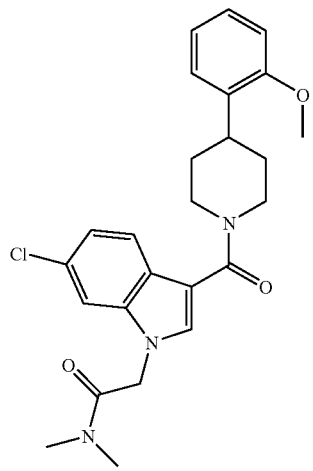

Following general procedure II, the alkylation of (6-chloro-1H-indol-3-yl)-[4-(2-methoxy-phenyl)-piperazin-1-yl]-methanone (preparation described herein), with (commercially available) 2-chloro-N,N-dimethyl-acetamide gave the title compound.

ES-MS m/e (%): 455.2 (M+H$^+$).

Example 152

2-{6-Chloro-3-[4-(2-ethoxy-phenyl)-piperazine-1-carbonyl]-indol-1-yl}-N,N-dimethyl-acetamide

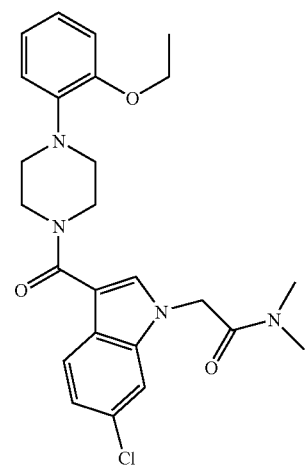

Amide coupling according to general procedure I:
Amine: 1-(2-Ethoxy-phenyl)-piperazine (commercially available),
Acid: 6-Chloro-1-dimethylcarbamoylmethyl-1H-indole-3-carboxylic acid,
ES-MS m/e (%): 469.1 (M+H$^+$).

Example 153

2-{6-Chloro-3-[4-(2-methoxy-phenyl)-piperazine-1-carbonyl]-indol-1-yl}-1-(4-methyl-piperazin-1-yl)-ethanone

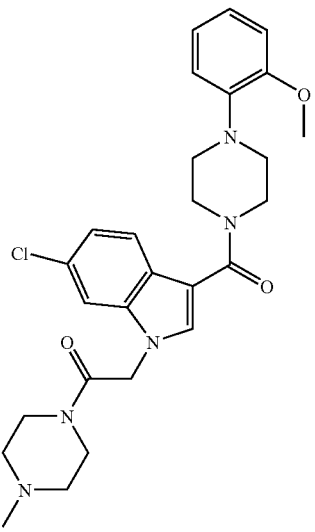

Following general procedure II, the alkylation of (6-chloro-1H-indol-3-yl)-[4-(2-methoxy-phenyl)-piperazin-1-yl]-methanone (preparation described herein), with (commercially available) 2-chloro-1-(4-methyl-piperazin-1-yl)-ethanone gave the title compound.

ES-MS m/e (%): 510.6 (M+H$^+$).

Example 154

2-{6-Chloro-3-[4-(2-ethoxy-phenyl)-piperazine-1-carbonyl]-indol-1-yl}-1-(4-methyl-piperazin-1-yl)-ethanone

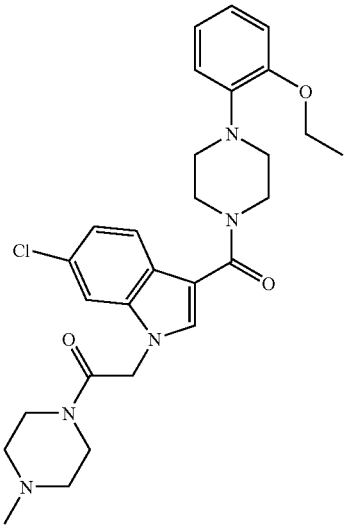

Following general procedure II, the alkylation of (6-chloro-1H-indol-3-yl)-[4-(2-ethoxy-phenyl)-piperazin-1-yl]-methanone (preparation described herein), with (commercially available) 2-chloro-1-(4-methyl-piperazin-1-yl)-ethanone gave the title compound.

ES-MS m/e (%): 524.6 (M+H$^+$).

Example 155

2-{6-Chloro-3-[4-(2-methoxy-phenyl)-piperazine-1-carbonyl]-indol-1-yl}-N-(2-dimethylamino-ethyl)-acetamide

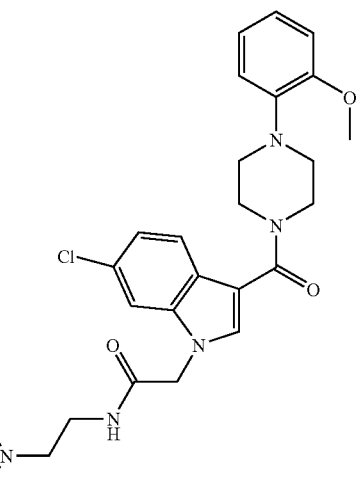

Analogous to general procedure I, the coupling of {6-chloro-3-[4-(2-methoxy-phenyl)-piperazine-1-carbonyl]-indol-1-yl}-acetic acid (prepared herein) with (commercially available) N$^1$,N$^1$-dimethyl-ethane-1,2-diamine gave the title compound.

ES-MS m/e (%): 499.6 (M+H$^+$).

Example 156

2-{6-Chloro-3-[4-(2-ethoxy-phenyl)-piperazine-1-carbonyl]-indol-1-yl}-N-(2-dimethylamino-ethyl)-acetamide

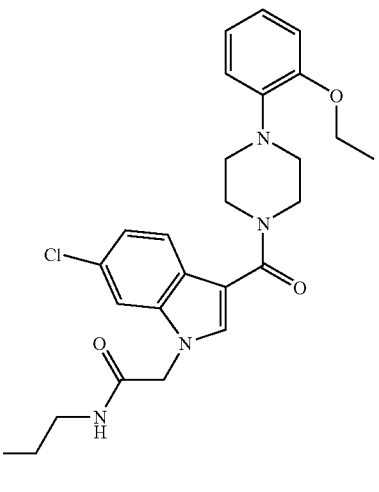

Analogous to general procedure I, the coupling of {6-chloro-3-[4-(2-ethoxy-phenyl)-piperazine-1-carbonyl]- indol-1-yl}-acetic acid (prepared herein) with (commercially available) $N^1,N^1$-dimethyl-ethane-1,2-diamine gave the title compound.
ES-MS m/e (%): 512.6 (M+H$^+$).

Example 157

2-{6-Chloro-3-[4-(2-methoxy-phenyl)-piperazine-1-carbonyl]-indol-1-yl}-acetamide

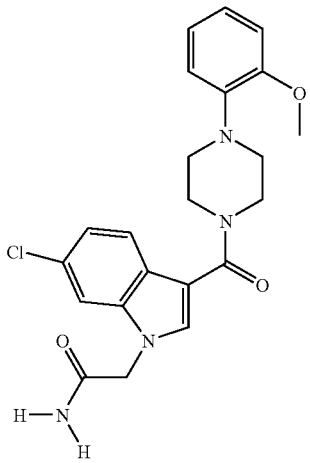

Analogous to general procedure I, the coupling of {6-chloro-3-[4-(2-methoxy-phenyl)-piperazine-1-carbonyl]-indol-1-yl}-acetic acid (prepared described herein) with (commercially available) ammonia in THF, gave the title compound.
ES-MS m/e (%): 427.5 (M+H$^+$).

Example 158

2-{6-Chloro-3-[4-(2-methoxy-phenyl)-piperidine-1-carbonyl]-5-methyl-indol-1-yl}-N,N-dimethyl-acetamide

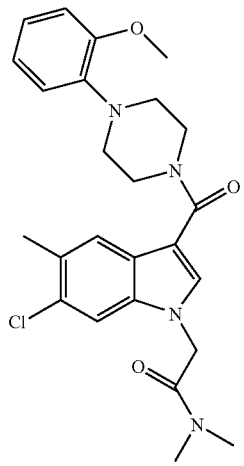

Amide coupling according to general procedure I:
Amine: 1-(2-Methoxy-phenyl)-piperazine (commercially available),
Acid: 6-Chloro-1-dimethylcarbamoylmethyl-5-methyl-1H-indole-3-carboxylic acid,
ES-MS m/e (%): 469.3 (M+H$^+$).

Example 159

2-{6-Chloro-3-[4-(2-methoxy-phenyl)-piperazine-1-carbonyl]-indol-1-yl}-1-piperazin-1-yl-ethanone hydrochloride

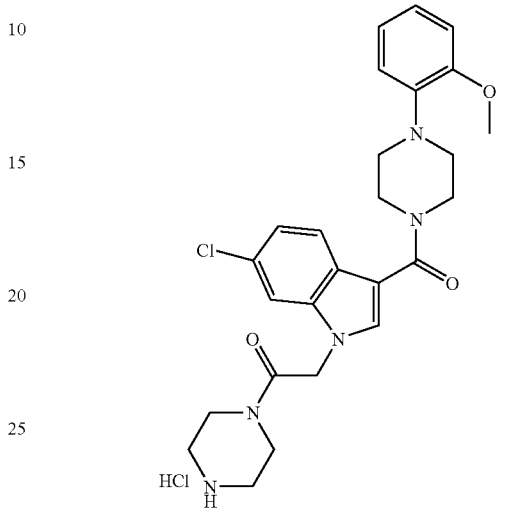

Analogous to general procedure I, the coupling of {6-chloro-3-[4-(2-methoxy-phenyl)-piperazine-1-carbonyl]-indol-1-yl}-acetic acid (prepared described herein) with (commercially available)) piperazine-1-carboxylic acid tert-butyl ester gave, after treatment with HCl, the title compound.
ES-MS m/e (%): 496.5 (M+H$^+$).

Example 160

2-{6-Chloro-3-[4-(2-methoxy-phenyl)-piperazine-1-carbonyl]-indol-1-yl}-N-(2-methylamino-ethyl)-acetamide hydrochloride

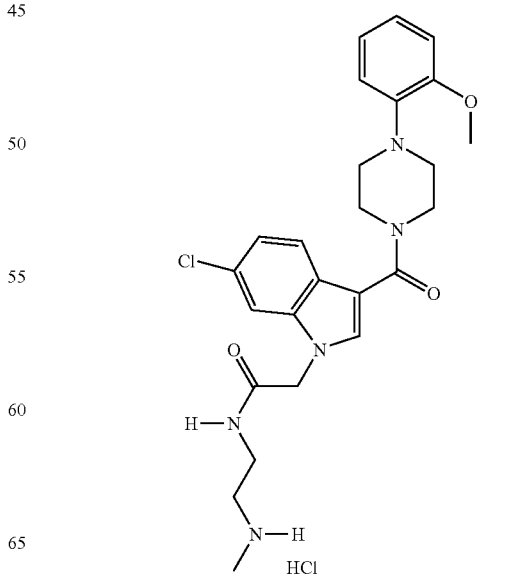

Analogous to general procedure I, the coupling of {6-chloro-3-[4-(2-methoxy-phenyl)-piperazine-1-carbonyl]-indol-1-yl}-acetic acid (prepared herein) with (commercially available) (2-amino-ethyl)-methyl-carbamic acid tert-butyl ester gave, after treatment with HCl, the title compound.

ES-MS m/e (%): 484.5 (M+H$^+$).

Example 161

N-(2-Amino-ethyl)-2-{6-chloro-3-[4-(2-methoxy-phenyl)-piperazine-1-carbonyl]-indol-1-yl}-acetamide hydrochloride {6-Chloro-3-[4-(2-methoxy-phenyl)-piperazine-1-carbonyl]-indol-1-yl}-acetic acid Following general procedure II, the alkylation of (6-chloro-1H-indol-3-yl)-[4-(2-methoxy-phenyl)-piperazin-1-yl]-methanone (preparation described herein), with (commercially available) bromo-acetic acid gave the title compound.

ES-MS m/e (%): 428.5 (M+H$^+$).

N-(2-Amino-ethyl)-2-{6-chloro-3-[4-(2-methoxy-phenyl)-piperazine-1-carbonyl]-indol-1-yl}-acetamide hydrochloride

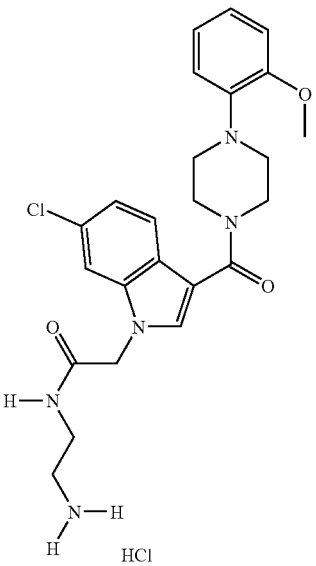

Analogous to general procedure I, the coupling of {6-chloro-3-[4-(2-methoxy-phenyl)-piperazine-1-carbonyl]-indol-1-yl}-acetic acid with (commercially available) (2-amino-ethyl)-carbamic acid tert-butyl ester gave, after treatment with HCl, the title compound.

ES-MS m/e (%): 470.6 (M+H$^+$).

Example 162

2-{6-Chloro-3-[4-(2-methoxy-phenyl)-piperazine-1-carbonyl]-indol-1-yl}-N-methyl-acetamide

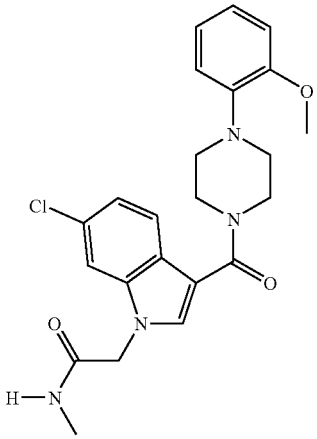

Following general procedure II, the alkylation of (6-chloro-1H-indol-3-yl)-[4-(2-methoxy-phenyl)-piperazin-1-yl]-methanone (preparation described herein), with (commercially available) 2-chloro-N-methyl-acetamide gave the title compound.

ES-MS m/e (%): 441.5 (M+H$^+$).

Example 163

[6-Chloro-1-(2-dimethylamino-ethyl)-1H-indol-3-yl]-[4-(2-methoxy-phenyl)-piperazin-1-yl]-methanone

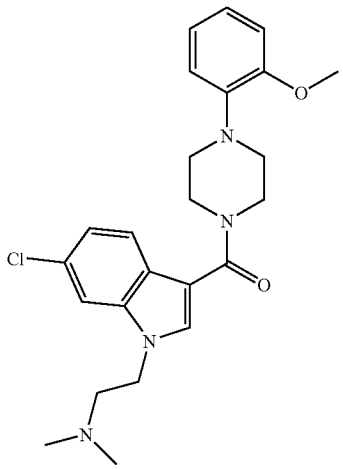

Analogous to general procedure II, the alkylation of (6-chloro-1H-indol-3-yl)-[4-(2-methoxy-phenyl)-piperazin-1-yl]-methanone (prepared herein) with (commercially available) (2-chloro-ethyl)-dimethyl-amine gave the title compound.

ES-MS m/e (%): 441.5 (M+H$^+$).

Example 164

[1-(2-Amino-ethyl)-6-chloro-1H-indol-3-yl]-[4-(2-methoxy-phenyl)-piperazin-1-yl]-methanone

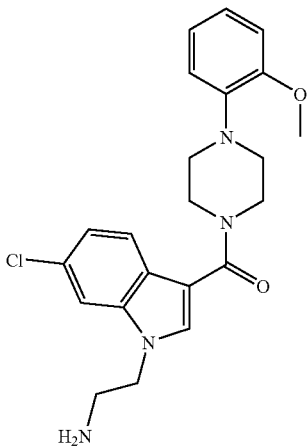

Analogous to general procedure II, the alkylation of (6-chloro-1H-indol-3-yl)-[4-(2-methoxy-phenyl)-piperazin-1-yl]-methanone (prepared herein) with (commercially available) 2-chloro-ethylamine gave the title compound.

ES-MS m/e (%): 413.4 (M+H$^+$).

Example 165

[6-Chloro-1-(2-methylamino-ethyl)-1H-indol-3-yl]-[4-(2-methoxy-phenyl)-piperazin-1-yl]-methanone

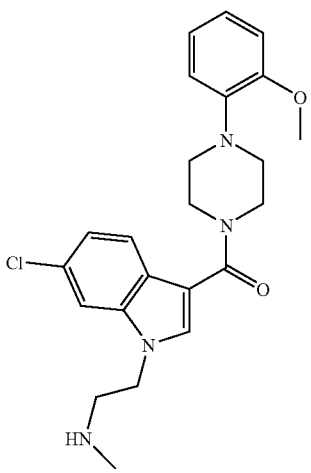

Analogous to general procedure II, the alkylation of (6-chloro-1H-indol-3-yl)-[4-(2-methoxy-phenyl)-piperazin-1-yl]-methanone (prepared herein) with (commercially available) (2-chloro-ethyl)-methyl-amine gave the title compound.

ES-MS m/e (%): 427.5 (M+H$^+$).

Example 166

[6-Chloro-1-(2-methylamino-ethyl)-1H-indol-3-yl]-[4-(2-ethoxy-phenyl)-piperazin-1-yl]-methanone

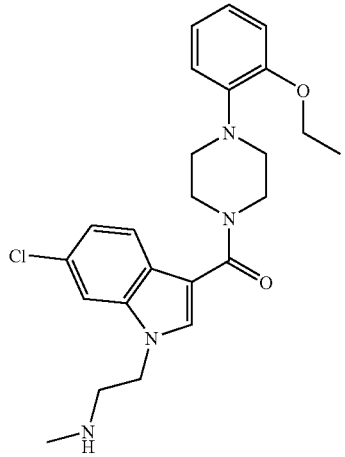

Following general procedure II, the alkylation of (6-chloro-1H-indol-3-yl)-[4-(2-ethoxy-phenyl)-piperazin-1-yl]-methanone (preparation described herein), with (commercially available) (2-chloro-ethyl)-methyl-amine gave the title compound.

ES-MS m/e (%): 441.5 (M+H$^+$).

Example 167

2-{6-Chloro-3-[4-(2-ethoxy-phenyl)-piperazine-1-carbonyl]-indol-1-yl}-N-(2-methylamino-ethyl)-acetamide {6-Chloro-3-[4-(2-ethoxy-phenyl)-piperazine-1-carbonyl]-indol-1-yl}-acetic acid Following general procedure II, the alkylation of (6-chloro-1H-indol-3-yl)-[4-(2-ethoxy-phenyl)-piperazin-1-yl]-methanone (preparation described herein), with (commercially available) bromo-acetic acid gave the title compound.

ES-MS m/e (%): 440.0 (M+H$^+$).

2-{6-Chloro-3-[4-(2-ethoxy-phenyl)-piperazine-1-carbonyl]-indol-1-yl}-N-(2-methylamino-ethyl)-acetamide

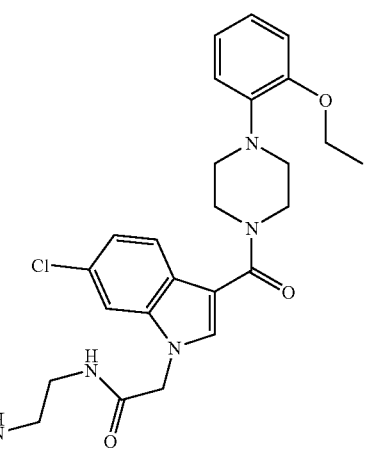

Analogous to general procedure I, the coupling of {6-chloro-3-[4-(2-ethoxy-phenyl)-piperazine-1-carbonyl]-indol-1-yl}-acetic acid with (commercially available) (2-amino-ethyl)-methyl-carbamic acid tert-butyl ester gave, after treatment with HCl and neutralisation, the title compound.

ES-MS m/e (%): 498.5 (M+H$^+$).

Example 168

[6-Chloro-1-(2-dimethylamino-ethyl)-1H-indol-3-yl]-[4-(2-ethoxy-phenyl)-piperazin-1-yl]-methanone

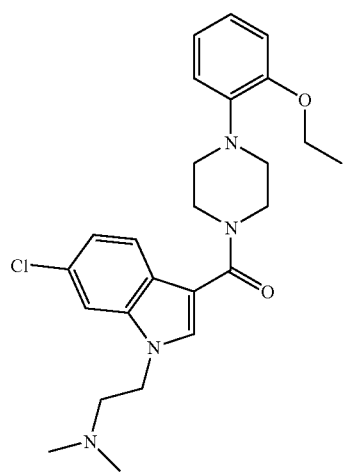

Following general procedure II, the alkylation of (6-chloro-1H-indol-3-yl)-[4-(2-ethoxy-phenyl)-piperazin-1-yl]-methanone (preparation described herein), with (commercially available) (2-chloro-ethyl)-dimethyl-amine gave the title compound.

ES-MS m/e (%): 455.3 (M+H$^+$).

Example 169

(6-Chloro-1H-indol-3-yl)-[4-(2-fluoro-phenyl)-piperazin-1-yl]-methanone

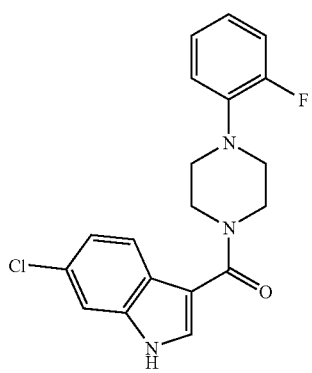

Following general procedure I, the coupling of (commercially available) 1-(2-fluoro-phenyl)-piperazine (described herein) with 6-chloro-1H-indole-3-carboxylic acid gave the title compound.

ES-MS m/e (%): 358.0 (M+H$^+$).

Example 170

[1-(2-Amino-ethyl)-6-chloro-1H-indol-3-yl]-[4-(2-fluoro-phenyl)-piperazin-1-yl]-methanone

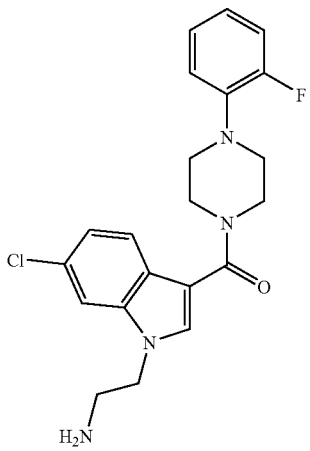

Following general procedure II, the alkylation of (6-chloro-1H-indol-3-yl)-[4-(2-fluoro-phenyl)-piperazin-1-yl]-methanone (preparation described herein), with (commercially available) 2-chloro-ethylamine gave the title compound.

ES-MS m/e (%): 401.2 (M+H$^+$).

Example 171

[6-Chloro-1-(2-dimethylamino-ethyl)-1H-indol-3-yl]-[4-(2-fluoro-phenyl)-piperazin-1-yl]-methanone

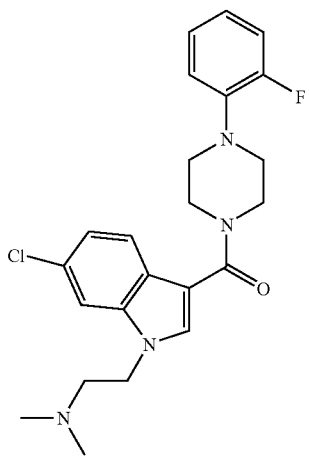

Following general procedure II, the alkylation of (6-chloro-1H-indol-3-yl)-[4-(2-fluoro-phenyl)-piperazin-1-yl]-methanone (preparation described herein), with (commercially available) (2-chloro-ethyl)-dimethyl-amine gave the title compound.

ES-MS m/e (%): 429.3 (M+H$^+$).

Example 172

2-{6-Chloro-3-[4-(2-fluoro-phenyl)-piperazine-1-carbonyl]-indol-1-yl}-1-(4-methyl-piperazin-1-yl)-ethanone

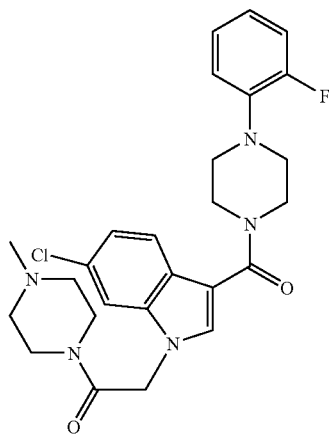

Following general procedure II, the alkylation of (6-chloro-1H-indol-3-yl)-[4-(2-fluoro-phenyl)-piperazin-1-yl]-methanone (preparation described herein), with (commercially available) 2-chloro-1-(4-methyl-piperazin-1-yl)-ethanone gave the title compound.

ES-MS m/e (%): 498.3 (M+H$^+$).

Example 173

2-{6-Chloro-3-[4-(2-fluoro-phenyl)-piperazine-1-carbonyl]-indol-1-yl}-N-(2-dimethylamino-ethyl)-acetamide

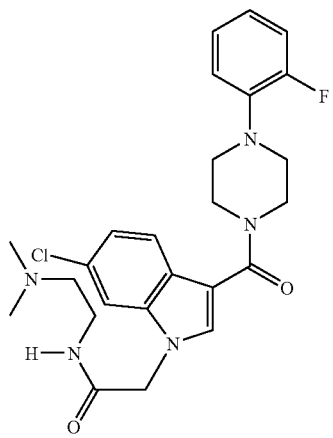

Following general procedure I, the coupling of {6-chloro-3-[4-(2-fluoro-phenyl)-piperazine-1-carbonyl]-indol-1-yl}-acetic acid, with (commercially available) N$^1$,N$^1$-dimethyl-ethane-1,2-diamine gave the title compound.

ES-MS m/e (%): 486.3 (M+H$^+$).

Example 174

2-{6-Chloro-3-[4-(2-fluoro-phenyl)-piperazine-1-carbonyl]-indol-1-yl}-N,N-dimethyl-acetamide

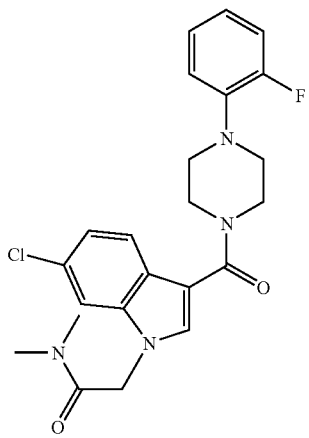

Following general procedure II, the alkylation of (6-chloro-1H-indol-3-yl)-[4-(2-fluoro-phenyl)-piperazin-1-yl]-methanone (preparation described herein), with (commercially available) 2-chloro-N,N-dimethyl-acetamide gave the title compound.

ES-MS m/e (%): 443.2 (M+H$^+$).

Example 175

2-{6-Chloro-3-[4-(2-fluoro-phenyl)-piperazine-1-carbonyl]-indol-1-yl}-acetamide

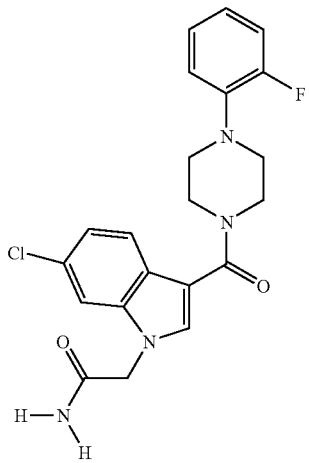

Following general procedure I, the coupling of {6-chloro-3-[4-(2-fluoro-phenyl)-piperazine-1-carbonyl]-indol-1-yl}-acetic acid (preparation described herein), with (commercially available) ammonia in THF gave the title compound.

ES-MS m/e (%): 415.2 (M+H$^+$).

Example 176

2-{6-Chloro-3-[4-(2-fluoro-phenyl)-piperazine-1-carbonyl]-indol-1-yl}-N-methyl-acetamide

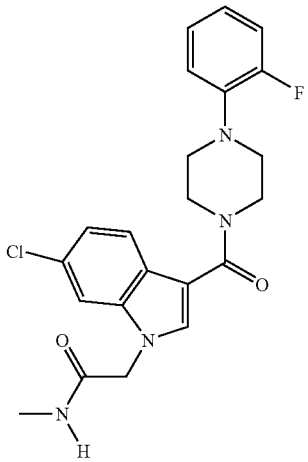

Following general procedure II, the alkylation of (6-chloro-1H-indol-3-yl)-[4-(2-fluoro-phenyl)-piperazin-1-yl]-methanone (preparation described herein), with (commercially available) 2-chloro-N-methyl-acetamide gave the title compound.

ES-MS m/e (%): 429.2 (M+H$^+$).

Example 177

2-{6-Chloro-3-[4-(2-fluoro-phenyl)-piperazine-1-carbonyl]-indol-1-yl}-1-piperazin-1-yl-ethanone {6-Chloro-3-[4-(2-fluoro-phenyl)-piperazine-1-carbonyl]-indol-1-yl}-acetic acid Following general procedure II, the alkylation of (6-chloro-1H-indol-3-yl)-[4-(2-fluoro-phenyl)-piperazin-1-yl]-methanone (preparation described herein), with (commercially available) bromo-acetic acid gave the title compound.

ES-MS m/e (%): 414.0 (M−H$^+$).

2-{6-Chloro-3-[4-(2-fluoro-phenyl)-piperazine-1-carbonyl]-indol-1-yl}-1-piperazin-1-yl-ethanone

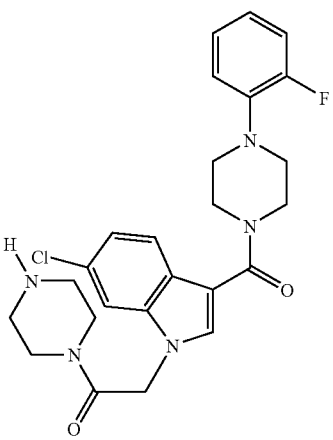

Following general procedure I, the coupling of {6-chloro-3-[4-(2-fluoro-phenyl)-piperazine-1-carbonyl]-indol-1-yl}-acetic acid, with (commercially available) piperazine-1-carboxylic acid tert-butyl ester gave, after treatment with HCl and neutralisation, gave the title compound.

ES-MS m/e (%): 484.2 (M+H$^+$).

Example 178

2-{6-Chloro-3-[4-(2-fluoro-phenyl)-piperazine-1-carbonyl]-indol-1-yl}-N-(2-methylamino-ethyl)-acetamide

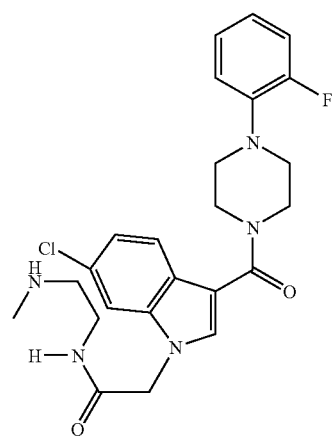

Following general procedure II, the alkylation of {6-chloro-3-[4-(2-fluoro-phenyl)-piperazine-1-carbonyl]-indol-1-yl}-acetic acid (preparation described herein), with (commercially available) (2-amino-ethyl)-methyl-carbamic acid tert-butyl ester gave, after treatment with HCl and neutralisation, the title compound.

ES-MS m/e (%): 472.2 (M+H$^+$).

Example 179

N-(2-Amino-ethyl)-2-{6-chloro-3-[4-(2-fluoro-phenyl)-piperazine-1-carbonyl]-indol-1-yl}-acetamide

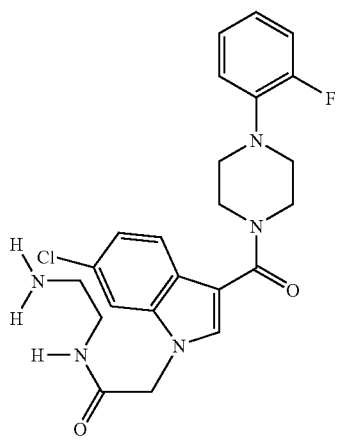

Following general procedure I, the coupling of {6-chloro-3-[4-(2-fluoro-phenyl)-piperazine-1-carbonyl]-indol-1-yl}-acetic acid (preparation described herein), with (commercially available) (2-amino-ethyl)-carbamic acid tert-butyl ester gave, after treatment with HCl and neutralisation, the title compound.

ES-MS m/e (%): 458.2 (M+H$^+$).

Example 180

2-{6-Chloro-3-[4-(2-methoxymethyl-phenyl)-piperazine-1-carbonyl]-indol-1-yl}-N-(2-dimethylamino-ethyl)-acetamide 4-(2-Methoxymethyl-phenyl)-piperazine-1-carboxylic acid tert-butyl ester A solution of (commercially available) 4-(2-hydroxymethyl-phenyl)-piperazine-1-carboxylic acid tert-butyl ester and (1 eq) MeI dissolved in THF was treated with NaH (2 eq) and stirred at RT for 2 h. After work-up, the crude solid was purified by SiO$_2$ chromatography (Ethyl acetate-Heptane 1:4) to give the title compound.

ES-MS m/e (%): 307.5 (M+H$^+$).

1-(2-Methoxymethyl-phenyl)-piperazine

A solution of 4-(2-methoxymethyl-phenyl)-piperazine-1-carboxylic acid tert-butyl ester (prepared as described herein below) in dioxan was treated with 4 eq. of 4M HCl in dioxane and stirred at RT for 16 h. After neutralization, the mixture was completely evaporated to give the crude title compound.

ES-MS m/e (%): 207.1 (M+H$^+$).

2-{6-Chloro-3-[4-(2-methoxymethyl-phenyl)-piperazine-1-carbonyl]-indol-1-yl}-N-(2-dimethylamino-ethyl)-acetamide

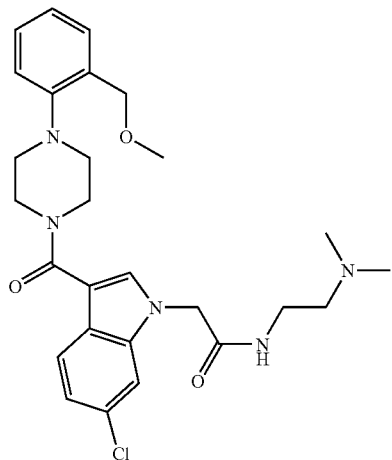

Following general procedure I, the coupling of 1-(2-methoxymethyl-phenyl)-piperazine, with 6-chloro-1-[(2-dimethylamino-ethylcarbamoyl)-methyl]-1H-indole-3-carboxylic acid (preparation described herein) gave the title compound.

ES-MS m/e (%): 512.3 (M+H$^+$).

Example 181

2-{6-Chloro-3-[4-(2-trifluoromethyl-phenyl)-piperazine-1-carbonyl]-indol-1-yl}-N-(2-dimethylamino-ethyl)-acetamide

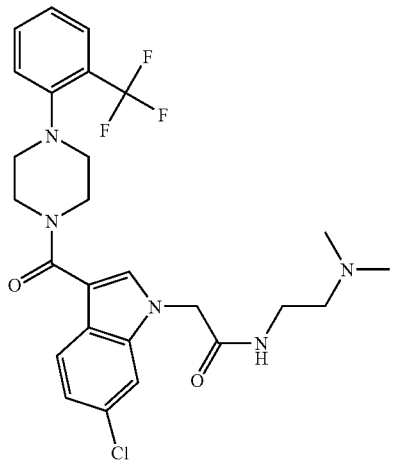

Following general procedure I, the coupling of (commercially available) 1-(2-trifluoromethyl-phenyl)-piperazine, with 6-chloro-1-[(2-dimethylamino-ethylcarbamoyl)-methyl]-1H-indole-3-carboxylic acid (preparation described herein) gave the title compound.

ES-MS m/e (%): 536.2 (M+H$^+$).

Example 182

2-[6-Chloro-3-(4-pyridin-2-yl-piperazine-1-carbonyl)-indol-1-yl]-N-(2-dimethylamino-ethyl)-acetamide

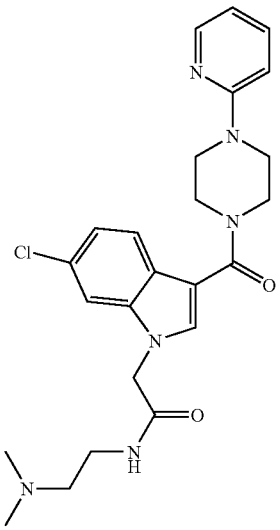

Following general procedure I, the coupling of (commercially available) 1-pyridin-2-yl-piperazine, with 6-chloro-1-[(2-dimethylamino-ethylcarbamoyl)-methyl]-1H-indole-3-carboxylic acid (preparation described herein) gave the title compound.

ES-MS m/e (%): 469.2 (M+H$^+$).

Example 183

2-[6-Chloro-3-(4-pyridin-2-yl-piperazine-1-carbonyl)-indol-1-yl]-N-(2-dimethylamino-ethyl)-acetamide

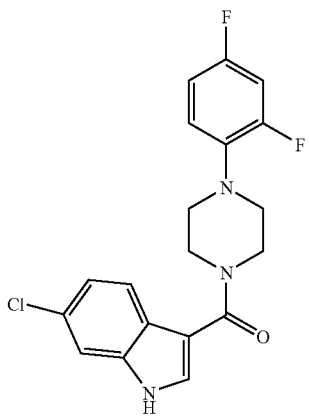

Following general procedure I, the coupling of (commercially available) 1-(2,4-difluoro-phenyl)-piperazine with 6-chloro-1H-indole-3-carboxylic acid gave the title compound.

ES-MS m/e (%): 376.1 (M+H$^+$).

Example 184

(6-Chloro-1H-indol-3-yl)-[4-(3-methyl-pyridin-2-yl)-piperazin-1-yl]-methanone

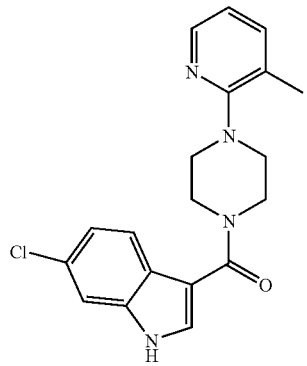

Following general procedure I, the coupling of (commercially available) 1-(3-methyl-pyridin-2-yl)-piperazine with 6-chloro-1H-indole-3-carboxylic acid gave the title compound.

ES-MS m/e (%): 355.1 (M+H$^+$).

Example 185

(6-Chloro-1H-indol-3-yl)-[4-(3,5-dichloro-pyridin-4-yl)-piperazin-1-yl]-methanone

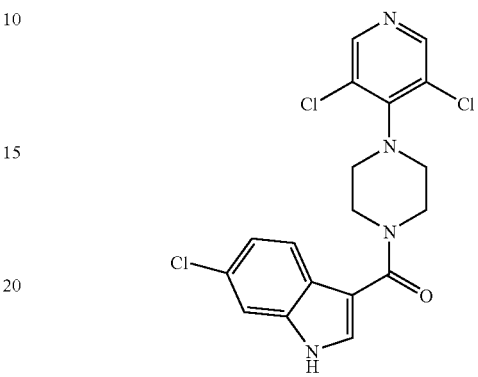

Following general procedure I, the coupling of (commercially available) 1-(3,5-dichloro-pyridin-4-yl)-piperazine with 6-chloro-1H-indole-3-carboxylic acid gave the title compound.

ES-MS m/e (%): 409.0 (M+H$^+$).

Example 186

(6-Chloro-1H-indol-3-yl)-[4-(3-trifluoromethyl-pyridin-2-yl)-piperazin-1-yl]-methanone

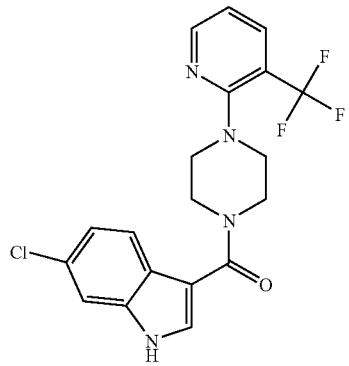

Following general procedure I, the coupling of (commercially available) 1-(3-trifluoromethyl-pyridin-2-yl)-piperazine with 6-chloro-1H-indole-3-carboxylic acid gave the title compound.

ES-MS m/e (%): 409.1 (M+H$^+$).

Example 187

2-[4-(6-Chloro-1H-indole-3-carbonyl)-piperazin-1-yl]-nicotinonitrile

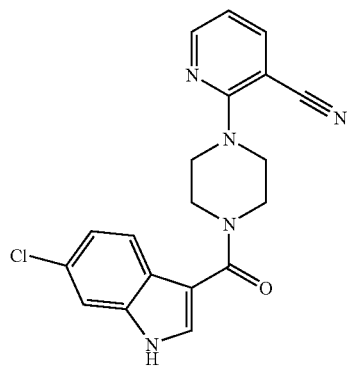

Following general procedure I, the coupling of (commercially available) 2-piperazin-1-yl-nicotinonitrile with 6-chloro-1H-indole-3-carboxylic acid gave the title compound.

ES-MS m/e (%): 366.1 (M+H$^+$).

Example 188

(6-Chloro-1H-indol-3-yl)-(4-pyridin-2-yl-piperazin-1-yl)-methanone

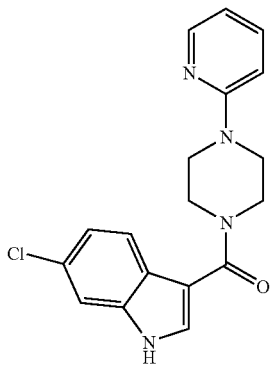

Following general procedure I, the coupling of (commercially available) 1-pyridin-2-yl-piperazine with 6-chloro-1H-indole-3-carboxylic acid gave the title compound.

ES-MS m/e (%): 341.1 (M+H$^+$).

Example 189

(6-Chloro-1H-indol-3-yl)-(4-thiazol-2-yl-piperazin-1-yl)-methanone

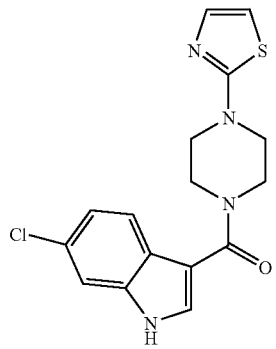

Following general procedure I, the coupling of (commercially available) 1-thiazol-2-yl-piperazine with 6-chloro-1H-indole-3-carboxylic acid gave the title compound.

ES-MS m/e (%): 347.0 (M+H$^+$).

Example 190

2-{6-Chloro-3-[4-(2,4-difluoro-phenyl)-piperazine-1-carbonyl]-indol-1-yl}-N-methyl-acetamide

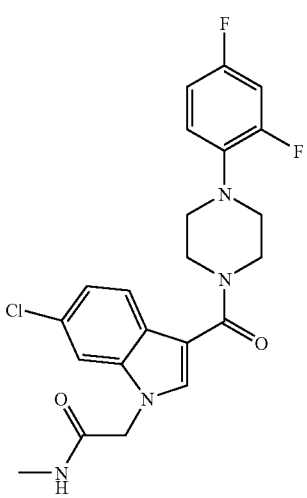

Following general procedure I, the coupling of (commercially available) 1-(2,4-difluoro-phenyl)-piperazine, with 6-chloro-1-methylcarbamoylmethyl-1H-indole-3-carboxylic acid (prepared as described herein below) gave the title compound.

ES-MS m/e (%): 447.1 (M+H$^+$).

Example 191

2-[6-Chloro-3-(2,3,5,6-tetrahydro-[1,2']bipyrazinyl-4-carbonyl)-indol-1-yl]-N-methyl-acetamide

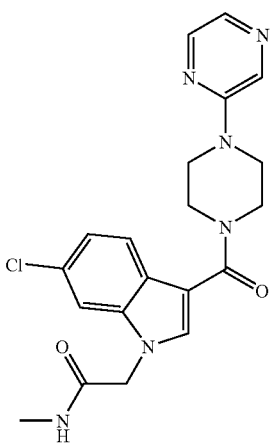

Following general procedure I, the coupling of (commercially available) 3,4,5,6-tetrahydro-2H-[1,2']bipyrazinyl, with 6-chloro-1-methylcarbamoylmethyl-1H-indole-3-carboxylic acid (prepared as described herein) gave the title compound.

ES-MS m/e (%): 413.1 (M+H$^+$).

Example 192

2-{6-Chloro-3-[4-(3-methyl-pyridin-2-yl)-piperazine-1-carbonyl]-indol-1-yl}-N-methyl-acetamide

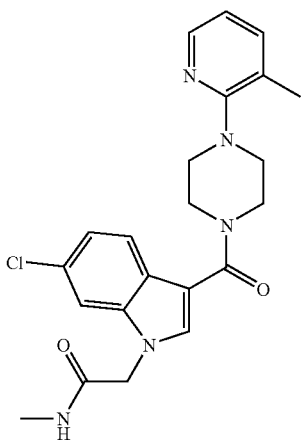

Following general procedure I, the coupling of (commercially available) 1-(3-methyl-pyridin-2-yl)-piperazine with 6-chloro-1-methylcarbamoylmethyl-1H-indole-3-carboxylic acid (prepared as described herein) gave the title compound.

ES-MS m/e (%): 426.2 (M+H$^+$).

Example 193

2-{6-Chloro-3-[4-(3,5-dichloro-pyridin-4-yl)-piperazine-1-carbonyl]-indol-1-yl}-N-methyl-acetamide

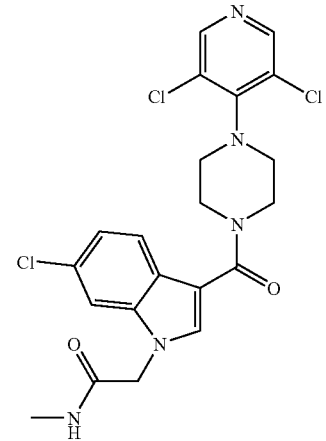

Following general procedure I, the coupling of (commercially available) 1-(3,5-dichloro-pyridin-4-yl)-piperazine with 6-chloro-1-methylcarbamoylmethyl-1H-indole-3-carboxylic acid (prepared as described herein) gave the title compound.

ES-MS m/e (%): 480.1 (M+H$^+$).

Example 194

2-[6-Chloro-3-(4-pyridin-2-yl-piperazine-1-carbonyl)-indol-1-yl]-N-methyl-acetamide

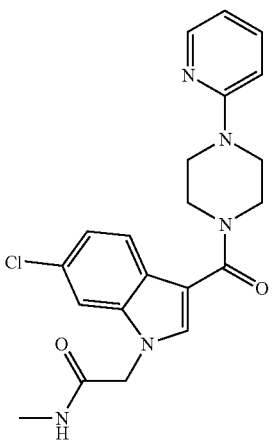

Following general procedure I, the coupling of (commercially available) 1-pyridin-2-yl-piperazine with 6-chloro-1-methylcarbamoylmethyl-1H-indole-3-carboxylic acid (prepared as described herein) gave the title compound.

ES-MS m/e (%): 412.1 (M+H$^+$).

Example 195

2-[6-Chloro-3-(4-thiazol-2-yl-piperazine-1-carbonyl)-indol-1-yl]-N-methyl-acetamide

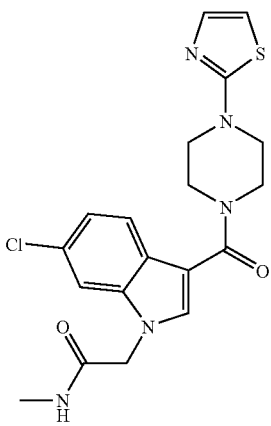

Following general procedure I, the coupling of (commercially available) 1-thiazol-2-yl-piperazine with 6-chloro-1-methylcarbamoylmethyl-1H-indole-3-carboxylic acid (prepared as described herein) gave the title compound.

ES-MS m/e (%): 418.1 (M+H$^+$).

Example 196

2-{6-Chloro-3-[4-(3-trifluoromethyl-pyridin-2-yl)-piperazine-1-carbonyl]-indol-1-yl}-N-methyl-acetamide

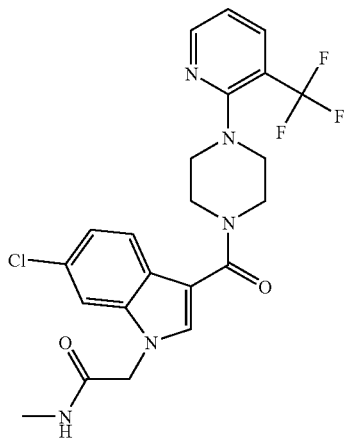

Following general procedure I, the coupling of (commercially available) 1-(3-trifluoromethyl-pyridin-2-yl)-piperazine with 6-chloro-1-methylcarbamoylmethyl-1H-indole-3-carboxylic acid (prepared as described herein) gave the title compound.

ES-MS m/e (%): 480.1 (M+H$^+$).

Example 197

2-{6-Chloro-3-[4-(3-cyano-pyridin-2-yl)-piperazine-1-carbonyl]-indol-1-yl}-N-methyl-acetamide

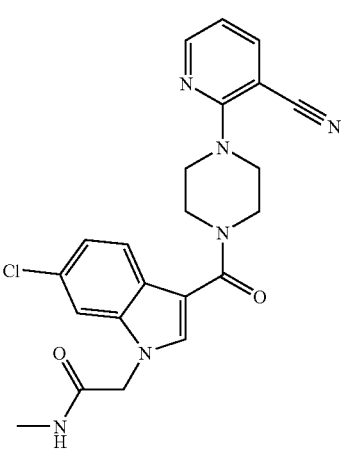

Following general procedure I, the coupling of (commercially available) 2-piperazin-1-yl-nicotinonitrile with 6-chloro-1-methylcarbamoylmethyl-1H-indole-3-carboxylic acid (prepared as described herein) gave the title compound.

ES-MS m/e (%): 437.1 (M+H$^+$).

Example 198

[1-((S)-2-Amino-propyl)-6-chloro-1H-indol-3-yl]-[4-(2-fluoro-phenyl)-piperazin-1-yl]-methanone

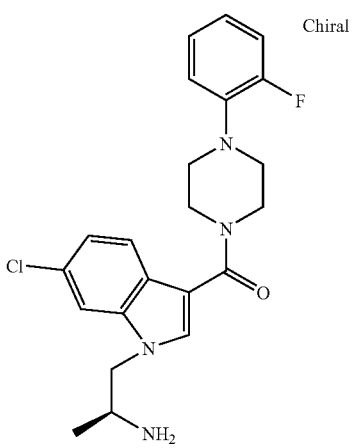

Following general procedure II, the alkylation of (6-chloro-1H-indol-3-yl)-[4-(2-fluoro-phenyl)-piperazin-1-yl]-methanone (preparation described herein), with methanesulfonic acid (S)-2-tert-butoxycarbonylamino-propyl ester (described in WO 2005100321) gave, after treatment with TFA and subsequent neutralization, the title compound.

ES-MS m/e (%): 415.2 (M+H$^+$).

Example 199

(6-Chloro-1-(S)-1-piperidin-3-ylmethyl-1H-indol-3-yl)-[4-(2-fluoro-phenyl)-piperazin-1-yl]-methanone

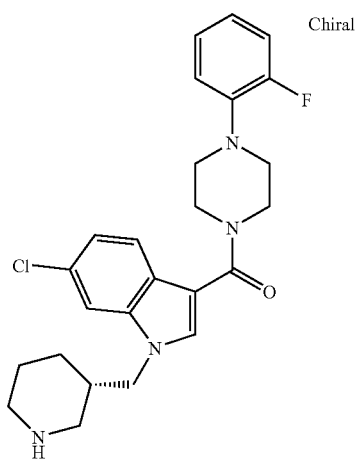

In analogy to the reaction conditions used in general procedure II, the alkylation of (6-chloro-1H-indol-3-yl)-[4-(2-fluoro-phenyl)-piperazin-1-yl]-methanone (preparation described herein), with methanesulfonic acid (S)-3-methanesulfonyloxymethyl-piperidine-1-carboxylic acid tert-butyl ester (described in JP 2001278872), followed by treatment with TFA and subsequent neutralisation, gave the title compound in 56% yield.

ES-MS m/e (%): 455.3 (M+H$^+$).

Example 200

(6-Chloro-1-(S)-1-pyrrolidin-2-ylmethyl-1H-indol-3-yl)-[4-(2-fluoro-phenyl)-piperazin-1-yl]-methanone

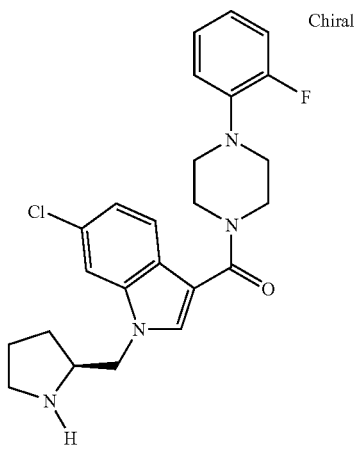

In analogy to the preparation of (6-chloro-1-(S)-1-piperidin-3-ylmethyl-1H-indol-3-yl)-[4-(2-fluoro-phenyl)-piperazin-1-yl]-methanone (described herein), the alkylation of (6-chloro-1H-indol-3-yl)-[4-(2-fluoro-phenyl)-piperazin-1-yl]-methanone (preparation described herein), with (S)-2-methanesulfonyloxymethyl-pyrrolidine-1-carboxylic acid tert-butyl ester (described in Tetrahedron: Asymmetry (1997), 8(13), 2209-2213), followed by treatment with TFA and subsequent neutralisation, gave the title compound in 55% yield.

ES-MS m/e (%): 441.3 (M+H$^+$).

Example 201

(6-Chloro-1-(RS)-1-pyrrolidin-3-ylmethyl-1H-indol-3-yl)-[4-(2-fluoro-phenyl)-piperazin-1-yl]-methanone

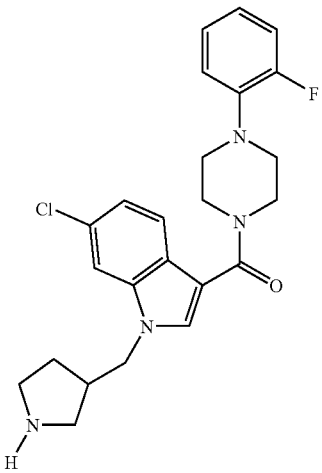

In analogy to the preparation of (6-chloro-1-(S)-1-piperidin-3-ylmethyl-1H-indol-3-yl)-[4-(2-fluoro-phenyl)-piperazin-1-yl]-methanone (described herein), the alkylation of (6-chloro-1H-indol-3-yl)-[4-(2-fluoro-phenyl)-piperazin-1-yl]-methanone (preparation described herein), with (RS)-3-methanesulfonyloxymethyl-pyrrolidine-1-carboxylic acid tert-butyl ester (described in WO 9742189), followed by treatment with TFA and subsequent neutralisation, gave the title compound in 51% yield.

ES-MS m/e (%): 441.3 (M+H$^+$).

Example 202

[6-Chloro-1-((S)-1-methyl-piperidin-3-ylmethyl)-1H-indol-3-yl]-[4-(2-fluoro-phenyl)-piperazin-1-yl]-methanone

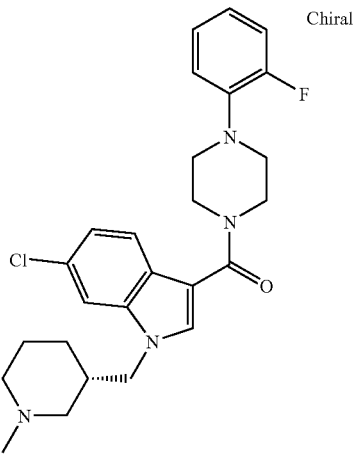

A solution of (6-chloro-1-(S)-1-piperidin-3-ylmethyl-1H-indol-3-yl)-[4-(2-fluoro-phenyl)-piperazin-1-yl]-methanone (preparation described herein below) in MeOH was treated with aq. H$_2$CO (1.5 eq) and AcOH (1.1 eq) and stirred for 15 min at RT, then treated with NaCNBH$_3$ (1.1 eq) and stirred at RT for 1 h. Concentration and purification by prep HPLC gave the desired product in 71% yield.

ES-MS m/e (%): 469.3 (M+H$^+$).

Example 203

[6-Chloro-1-((S)-1-methyl-pyrrolidin-2-ylmethyl)-1H-indol-3-yl]-[4-(2-fluoro-phenyl)-piperazin-1-yl]-methanone

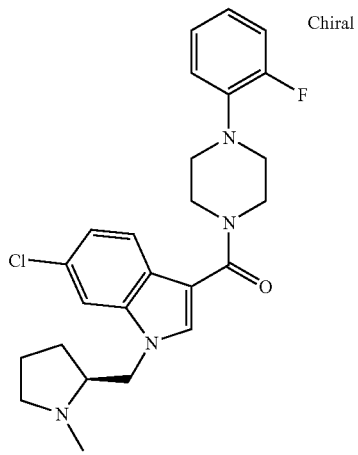

(6-Chloro-1-(S)-1-pyrrolidin-2-ylmethyl-1H-indol-3-yl)-[4-(2-fluoro-phenyl)-piperazin-1-yl]-methanone (preparation described herein), was treated with a 37% aq. solution of formaldehyde (1.05 eq.), acetic acid (1.05 eq.) and sodium cyanoborohydride (1.0 eq.) in MeOH at RT for 2 h to give after purification by prep. HPLC the title compound in 62% yield.

ES-MS m/e (%): 455.3 (M+H$^+$).

Example 204

[6-Chloro-1-((RS)-1-methyl-pyrrolidin-3-ylmethyl)-1H-indol-3-yl]-[4-(2-fluoro-phenyl-piperazin-1-yl]-methanone

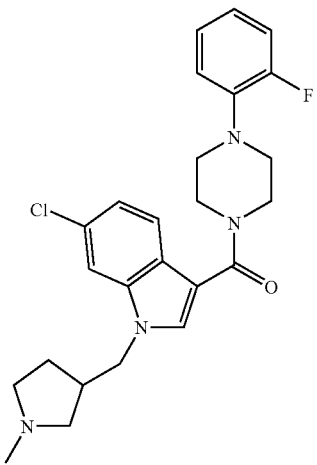

Following the procedure described in the preparation of (6-chloro-1-(S)-1-pyrrolidin-2-ylmethyl-1H-indol-3-yl)-[4-(2-fluoro-phenyl)-piperazin-1-yl]-methanone (described herein), the alkylation of (6-chloro-1-(RS)-1-pyrrolidin-3-ylmethyl-H-indol-3-yl)-[4-(2-fluoro-phenyl)-piperazin-1-yl]-methanone (preparation described herein) gave the title compound in 64% yield.

ES-MS m/e (%): 455.3 (M+H$^+$).

Example 205

2-{6-Chloro-3-[4-(2,4-difluoro-phenyl)-piperazine-1-carbonyl]-indol-1-yl}-N,N-dimethyl-acetamide

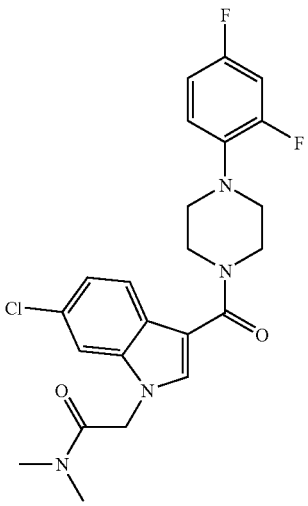

Following general procedure I, the coupling of (commercially available) 1-(2,4-difluoro-phenyl)-piperazine, with 6-chloro-1-dimethylcarbamoylmethyl-1H-indole-3-carboxylic acid gave the title compound.

ES-MS m/e (%): 461.2 (M+H$^+$).

Example 206

2-[6-Chloro-3-(2,3,5,6-tetrahydro-[1,2']bipyrazinyl-4-carbonyl)-indol-1-yl]-N,N-dimethyl-acetamide

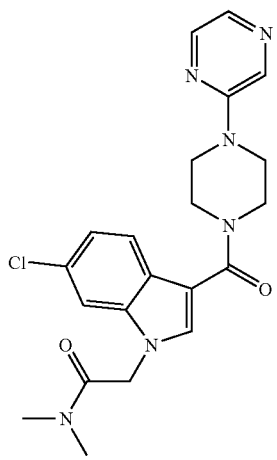

Following general procedure I, the coupling of (commercially available) 3,4,5,6-tetrahydro-2H-[1,2']bipyrazinyl, with 6-chloro-1-dimethylcarbamoylmethyl-1H-indole-3-carboxylic acid (prepared as described herein) gave the title compound.

ES-MS m/e (%): 427.2 (M+H$^+$).

Example 207

2-{6-Chloro-3-[4-(3-methyl-pyridin-2-yl)-piperazine-1-carbonyl]-indol-1-yl}-N,N-dimethyl-acetamide

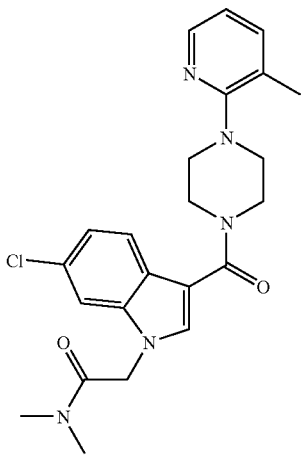

Following general procedure I, the coupling of (commercially available) 1-(3-methyl-pyridin-2-yl)-piperazine with 6-chloro-1-dimethylcarbamoylmethyl-1H-indole-3-carboxylic acid (prepared as described herein) gave the title compound.

ES-MS m/e (%): 440.2 (M+H$^+$).

Example 208

2-{6-Chloro-3-[4-(3,5-dichloro-pyridin-4-yl)-piperazine-1-carbonyl]-indol-1-yl}-N,N-dimethyl-acetamide

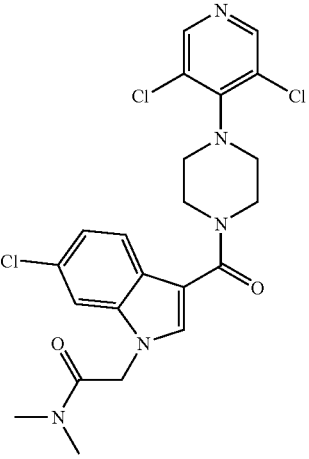

Following general procedure I, the coupling of (commercially available) 1-(3,5-dichloro-pyridin-4-yl)-piperazine with 6-chloro-1-dimethylcarbamoylmethyl-1H-indole-3-carboxylic acid (prepared as described herein) gave the title compound.

ES-MS m/e (%): 494.1 (M+H$^+$).

Example 209

2-[6-Chloro-3-(4-pyridin-2-yl-piperazine-1-carbonyl)-indol-1-yl]-N-methyl-acetamide

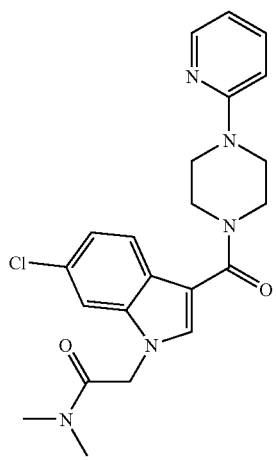

Following general procedure I, the coupling of (commercially available) 1-pyridin-2-yl-piperazine with 6-chloro-1-dimethylcarbamoylmethyl-1H-indole-3-carboxylic acid (prepared as described herein) gave the title compound.

ES-MS m/e (%): 426.2 (M+H$^+$).

Example 210

2-[6-Chloro-3-(4-thiazol-2-yl-piperazine-1-carbonyl)-indol-1-yl]-N,N-dimethyl-acetamide

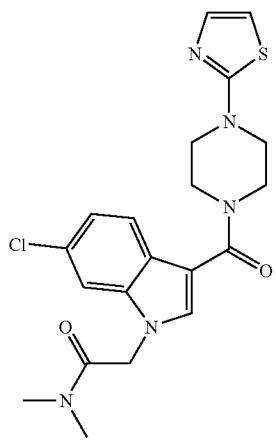

Following general procedure I, the coupling of (commercially available) 1-thiazol-2-yl-piperazine with 6-chloro-1-dimethylcarbamoylmethyl-1H-indole-3-carboxylic acid (prepared as described herein) gave the title compound.

ES-MS m/e (%): 432.2 (M+H$^+$).

Example 211

2-{6-Chloro-3-[4-(3-trifluoromethyl-pyridin-2-yl)-piperazine-1-carbonyl]-indol-1-yl}-N,N-dimethyl-acetamide

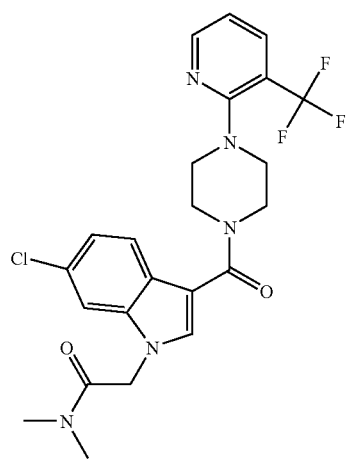

Following general procedure I, the coupling of (commercially available) 1-(3-trifluoromethyl-pyridin-2-yl)-piperazine with 6-chloro-1-dimethylcarbamoylmethyl-1H-indole-3-carboxylic acid gave the title compound.

ES-MS m/e (%): 494.2 (M+H$^+$).

Example 212

2-{6-Chloro-3-[4-(3-cyano-pyridin-2-yl)-piperazine-1-carbonyl]-indol-1-yl}-N,N-dimethyl-acetamide

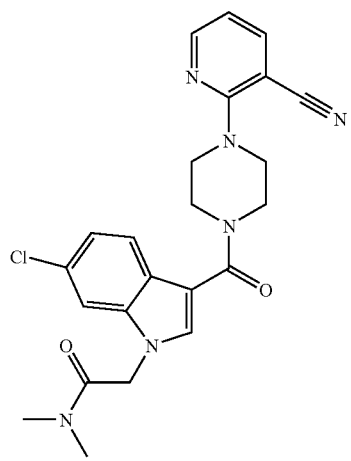

Following general procedure I, the coupling of (commercially available) 2-piperazin-1-yl-nicotinonitrile with 6-chloro-1-dimethylcarbamoylmethyl-1H-indole-3-carboxylic acid (prepared as described herein) gave the title compound.

ES-MS m/e (%): 451.2 (M+H$^+$).

Example 213

2-[6-Chloro-3-(4-pyrimidin-2-yl-piperazine-1-carbonyl)-indol-1-yl]-N,N-dimethyl-acetamide

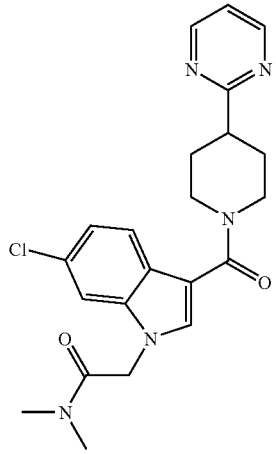

Following general procedure I, the coupling of (commercially available) 2-piperidin-4-yl-pyrimidine with 6-chloro-1-dimethylcarbamoylmethyl-1H-indole-3-carboxylic acid (prepared as described herein) gave the title compound.

ES-MS m/e (%): 427.2 (M+H$^+$).

Example 214

(6-Chloro-1-(R)-1-pyrrolidin-2-ylmethyl-1H-indol-3-yl)-[4-(2-fluoro-phenyl)-piperazin-1-yl]-methanone

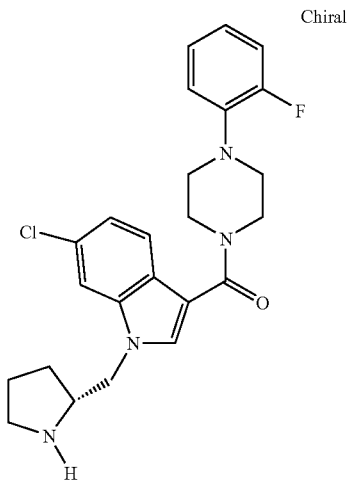

In analogy to the preparation of (6-chloro-1-(S)-1-piperidin-3-ylmethyl-1H-indol-3-yl)-[4-(2-fluoro-phenyl)-piperazin-1-yl]-methanone (described herein), the alkylation of (6-chloro-1H-indol-3-yl)-[4-(2-fluoro-phenyl)-piperazin-1-yl]-methanone (preparation described herein), with (R)-2- methanesulfonyloxymethyl-pyrrolidine-1-carboxylic acid tert-butyl ester (described in Tetrahedron: Asymmetry (1997), 8(13), 2209-2213), followed by treatment with TFA and subsequent neutralisation, gave the title compound in 26% yield.

ES-MS m/e (%): 441.3 (M+H⁺).

Example 215

[6-Chloro-1-((R)-1-methyl-pyrrolidin-2-ylmethyl)-1H-indol-3-yl]-[4-(2-fluoro-phenyl)-piperazin-1-yl]-methanone

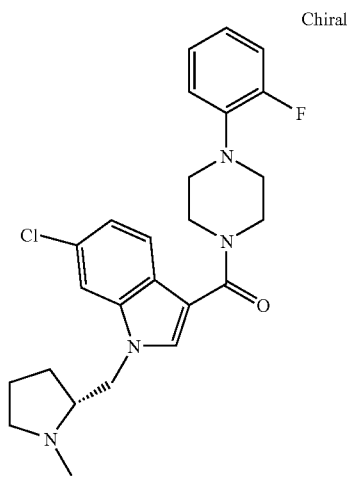

Chiral

Following the procedure described in the preparation of [6-chloro-1-((S)-1-methyl-pyrrolidin-2-ylmethyl)-1H-indol-3-yl]-[4-(2-fluoro-phenyl)-piperazin-1-yl]-methanone, the alkylation of (6-chloro-1-(R)-1-pyrrolidin-2-ylmethyl-1H-indol-3-yl)-[4-(2-fluoro-phenyl)-piperazin-1-yl]-methanone (preparation described herein) gave the title compound.

ES-MS m/e (%): 455.3 (M+H⁺)

Example 216

(6-Chloro-2-methyl-1H-indol-3-yl)-[4-(2-methoxy-phenyl)-piperazin-1-yl]-methanone

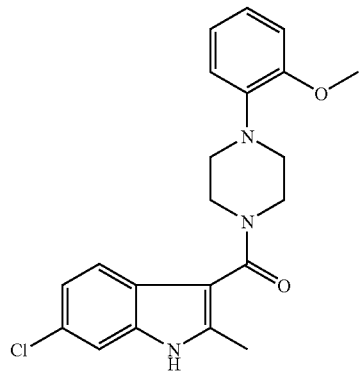

The title compound was obtained as a white solid in 16% yield according to the procedure described for the preparation of (6-chloro-2-methyl-1H-indol-3-yl)-[4-(2-methoxy-phenyl)-piperidin-1-yl]-methanone using 1-(2-methoxy-phenyl)-piperazine instead of 4-(2-methoxy-phenyl)-piperidine.

MS m/e (%): 382 (M−H⁺, 100).

Example 217

N-(2-{6-Chloro-3-[4-(2-fluoro-phenyl)-piperazine-1-carbonyl]-indol-1-yl}-ethyl)-acetamide

[1-(2-Amino-ethyl)-6-chloro-1H-indol-3-yl]-[4-(2-fluoro-phenyl)-piperazin-1-yl]-methanone To a solution of (6-chloro-1H-indol-3-yl)-[4-(2-fluoro-phenyl)-piperazin-1-yl]-methanone in dry DMF under argon at 0° C. was added (1.1 eq) NaH. The reaction mixture was stirred for 1 h at 0° C. 2,2-Dioxo-2λ⁶-[1,2,3]oxathiazolidine-3-carboxylic acid tert-butyl ester (1.1 eq) (described in WO 2003037327) was added, and the reaction mixture was stirred for 2 h at RT. After evaporation of DMF, redissolution in dioxan, addition of 5 eq. of HCl (4.0M solution in dioxane) and a few drops of water, the reaction mixture was stirred for 2 h at 50° C.; LC-MS showed complete conversion to the crude product.

Concentration in vacuo, redissolution in EtOAc, and washing with 1N NaHCO₃, gave after concentration, the crude product which was purified by SiO₂ gel chromatography with CH₂Cl₂/MeOH to give the title compound in 55% yield.

ES-MS m/e (%): 401.2 (M+H⁺).

N-(2-{6-Chloro-3-[4-(2-fluoro-phenyl)-piperazine-1-carbonyl]-indol-1-yl}-ethyl)-acetamide

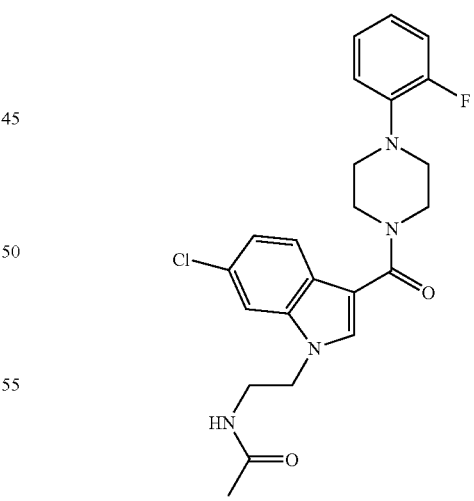

[1-(2-Amino-ethyl)-6-chloro-1H-indol-3-yl]-[4-(2-fluoro-phenyl)-piperazin-1-yl]-methanone, was treated with acetylchloride (1.05 eq) and triethylamine (1.05 eq) in CH₂Cl₂ under argon at RT for 2 h to give after purification by prep. HPLC the title compound.

ES-MS m/e (%): 443.2 (M+H⁺).

Example 218

N-(2-{6-Chloro-3-[4-(2-fluoro-phenyl)-piperazine-1-carbonyl]-indol-1-yl}-ethyl)-methanesulfonamide

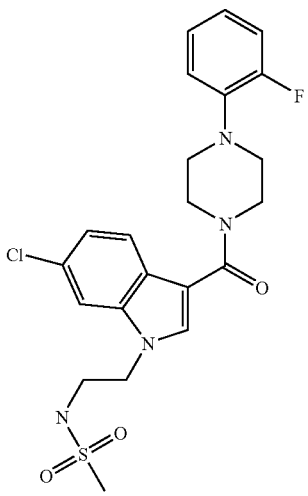

[1-(2-Amino-ethyl)-6-chloro-1H-indol-3-yl]-[4-(2-fluoro-phenyl)-piperazin-1-yl]-methanone (preparation described herein), was treated with mesylchloride (1.05 eq) and triethylamine (1.05 eq) in $CH_2Cl_2$ under argon at RT to give after purification by prep. HPLC the title compound.

ES-MS m/e (%): 479.1 (M+H$^+$).

Example 219

N-(2-{6-Chloro-3-[4-(2-fluoro-phenyl)-piperazine-1-carbonyl]-indol-1-yl}-ethyl)-N-methyl-acetamide

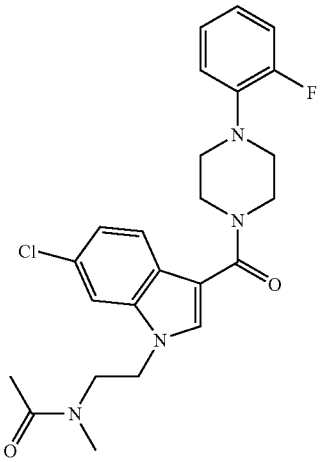

N-(2-{6-Chloro-3-[4-(2-fluoro-phenyl)-piperazine-1-carbonyl]-indol-1-yl}-ethyl)-acetamide (preparation described herein) was treated with NaH (1.05 eq), MeI (1.05 eq) in dry DMF under argon at RT for 2 h to give after purification by prep. HPLC the title compound.

ES-MS m/e (%): 457.1 (M+H$^+$).

Example 220

N-(2-{6-Chloro-3-[4-(2-fluoro-phenyl)-piperazine-1-carbonyl]-indol-1-yl}-ethyl)-N-methyl-acetamide

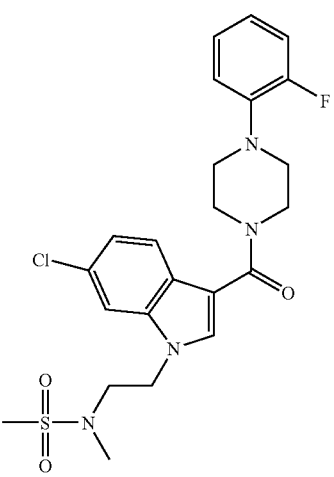

N-(2-{6-Chloro-3-[4-(2-fluoro-phenyl)-piperazine-1-carbonyl]-indol-1-yl}-ethyl-methanesulfonamide (preparation described herein), was treated with NaH (1.05 eq), MeI (1.05 eq) in dry DMF under argon at RT for 2 h to give after purification by prep. HPLC the title compound.

ES-MS m/e (%): 493.1 (M+H$^+$).

Example 221

2-{6-Chloro-3-[4-(6-chloro-pyridin-2-yl)-piperazine-1-carbonyl]-indol-1-yl}-N-methyl-acetamide

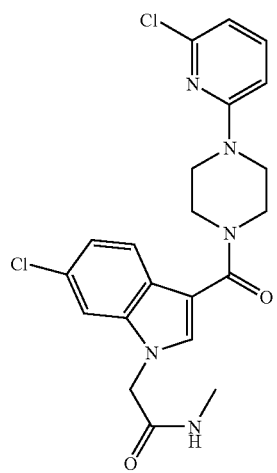

Following general procedure I, the coupling of (commercially available) 1-(6-chloro-pyridin-2-yl)-piperazine, with 6-chloro-1-methylcarbamoylmethyl-1H-indole-3-carboxylic acid (prepared as described herein) gave the title compound.

ES-MS m/e (%): 446.1 (M+H$^+$).

Example 222

2-{6-Chloro-3-[4-(5-trifluoromethyl-pyridin-2-yl)-piperazine-1-carbonyl]-indol-1-yl}-N-methyl-acetamide

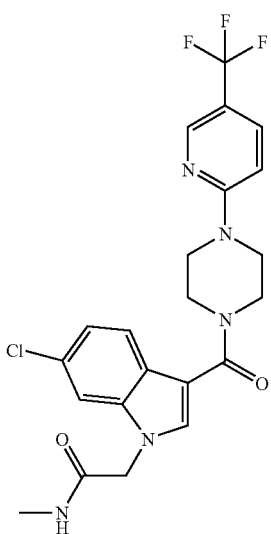

Following general procedure I, the coupling of (commercially available) 1-(5-trifluoromethyl-pyridin-2-yl)-piperazine, with 6-chloro-1-methylcarbamoylmethyl-1H-indole-3-carboxylic acid (prepared as described herein) gave the title compound.

ES-MS m/e (%): 480.1 (M+H$^+$).

Example 223

2-[6-Chloro-3-(4-thieno[2,3-c]pyridin-7-yl-piperazine-1-carbonyl)-indol-1-yl]-N-methyl-acetamide

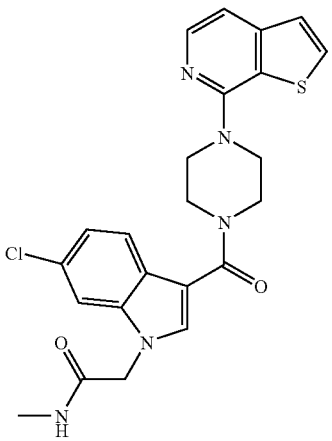

Following general procedure I, the coupling of (commercially available) 7-piperazin-1-yl-thieno[2,3-c]pyridine, with 6-chloro-1-methylcarbamoylmethyl-1H-indole-3-carboxylic acid (prepared as described herein) gave the title compound.

ES-MS m/e (%): 468.1 (M+H$^+$).

Example 224

2-[6-Chloro-3-(4-thieno[3,2-c]pyridin-4-yl-piperazine-1-carbonyl)-indol-1-yl]-N-methyl-acetamide

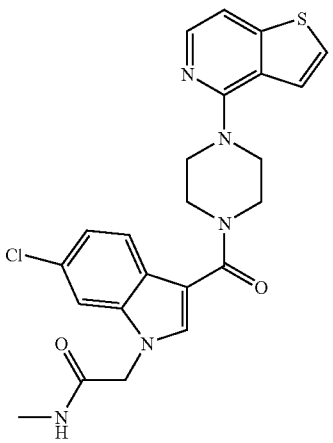

Following general procedure I, the coupling of (commercially available) 4-piperazin-1-yl-thieno[3,2-c]pyridine with 6-chloro-1-methylcarbamoylmethyl-1H-indole-3-carboxylic acid (prepared as described herein) gave the title compound.

ES-MS m/e (%): 468.1 (M+H$^+$).

Example 225

2-{6-Chloro-3-[4-(3-iodo-pyridin-2-yl)-piperazine-1-carbonyl]-indol-1-yl}-N-methyl-acetamide

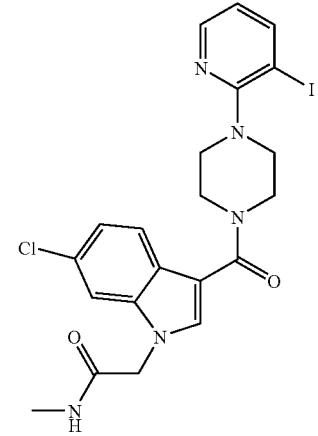

Following general procedure I, the coupling of (commercially available) 1-(3-iodo-pyridin-2-yl)-piperazine with 6-chloro-1-methylcarbamoylmethyl-1H-indole-3-carboxylic acid gave the title compound.

ES-MS m/e (%): 538.0 (M+H$^+$).

Example 226

2-{6-Chloro-3-[4-(3-chloro-5-trifluoromethyl-pyridin-2-yl)-piperazine-1-carbonyl]-indol-1-yl}-N-methyl-acetamide

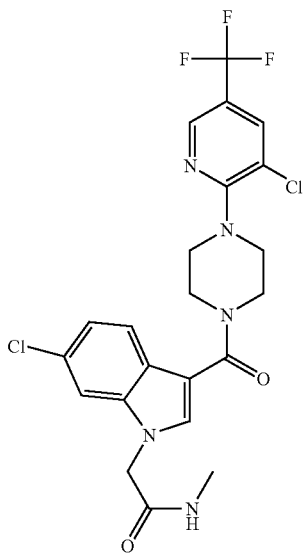

Following general procedure I, the coupling of (commercially available) 1-(3-chloro-5-trifluoromethyl-pyridin-2-yl)-piperazine with 6-chloro-1-methylcarbamoylmethyl-1H-indole-3-carboxylic acid (prepared as described herein) gave the title compound.

ES-MS m/e (%): 514.1 (M+H$^+$).

Example 227

2-[4-(6-Chloro-1-methylcarbamoylmethyl-1H-indole-3-carbonyl)-piperazin-1-yl]-nicotinic acid

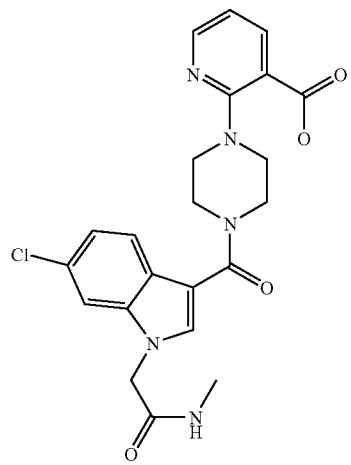

Following general procedure I, the coupling of (commercially available) 2-piperazin-1-yl-nicotinic acid with 6-chloro-1-methylcarbamoylmethyl-1H-indole-3-carboxylic acid (prepared as described herein) gave the title compound.

ES-MS m/e (%): 456.1 (M+H$^+$).

Example 228

2-{6-Chloro-3-[4-(2,4-difluoro-phenyl)-piperazine-1-carbonyl]-indol-1-yl}-N-(2-dimethylamino-ethyl)-acetamide

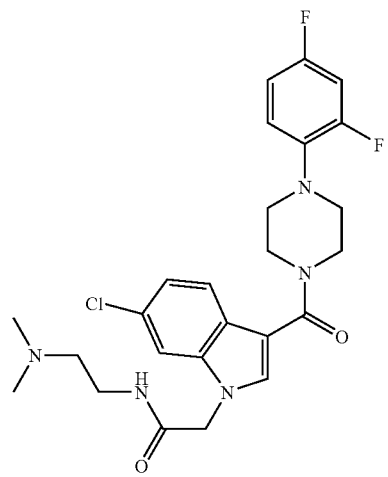

Following general procedure I, the coupling of (commercially available) 1-(2,4-difluoro-phenyl)-piperazine with 6-chloro-1-[(2-dimethylamino-ethylcarbamoyl)-methyl]-1H-indole-3-carboxylic acid (prepared as described herein) gave the title compound.

ES-MS m/e (%): 504.3 (M+H$^+$).

Example 229

2-{6-Chloro-3-[4-(4-fluoro-2-methanesulfonyl-phenyl)-piperazine-1-carbonyl]-indol-1-yl}-N-methyl-acetamide

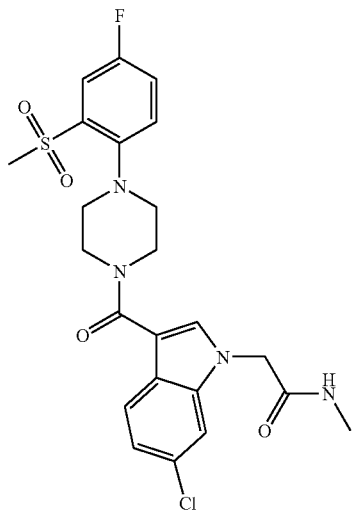

Following general procedure I, the coupling of (commercially available) 1-(4-fluoro-2-methanesulfonyl-phenyl)-piperazine with 6-chloro-1-methylcarbamoylmethyl-1H-indole-3-carboxylic acid (prepared as described herein) gave the title compound.

ES-MS m/e (%): 506.9 (M+H$^+$).

Example of a Compound of Formula I-d

Example 230

(6-Chloro-1H-indol-3-yl)-[4-(2-methoxy-phenyl)-4-oxy-piperazin-1-yl]-methanone

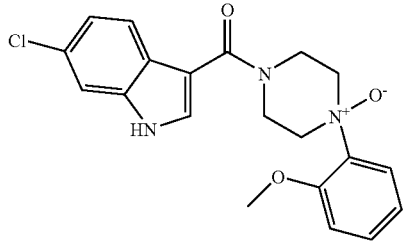

Amide coupling according to general procedure I:
Amine: 1-(2-Methoxy-phenyl)-piperazine 1-oxide (described in EP126480),
Acid: 6-chloro-1H-indole-3-carboxylic acid,
ES-MS m/e (%): 386.4 (M+H$^+$).

The invention claimed is:
1. A compound of formula I:

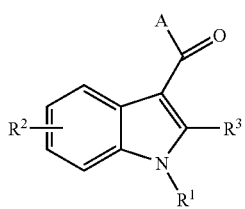

wherein:
R$^1$ is C$_{1-6}$-alkyl substituted by NR$^i$R$^{ii}$,
—(CH$_2$)$_m$—R$^a$ wherein R$^a$ is:
NR$^i$R$^{ii}$, or
5 to 6 membered-heterocycloalkyl, aryl, or 5 or 6 membered heteroaryl each of which is optionally substituted by one or more B,
or —(CH$_2$)$_n$—(CO)—R$^b$ or —(CH$_2$)$_n$—(SO$_2$)—R$^b$, wherein R$^b$ is:
C$_{1-6}$-alkyl,
C$_{1-6}$-alkoxy,
NR$^i$R$^{ii}$, or
5 to 6 membered-heterocycloalkyl, aryl, or 5 or 6 membered heteroaryl each of which is optionally substituted by one or more B,
or R$^1$ and R$^3$ together with the indole ring to which they are attached form a piperazinyl, which is optionally substituted by =O, C(O)O—C$_{1-6}$-alkyl or C$_{1-6}$-alkyl;
there is one or more R$^2$, wherein each R$^2$ is the same or different, R$^2$ is one or more H, halo, or C$_{1-6}$-alkyl;
R$^3$ is H, or
C$_{1-6}$-alkyl;
A is

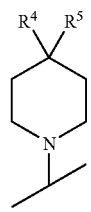

wherein
R$^4$ is aryl selected from the group consisting of phenyl, naphthyl, phenanthryl, fluorenyl, indenyl, pentalenyl, azulenyl, biphenyl, aminodiphenyl, diphenylsulfidyl, diphenylsulfonyl, and diphenylisopropylidenyl,
5 or 6 membered heteroaryl selected from the group consisting of imidazolyl, oxazolyl, thiazolyl, pyrazinyl, pyrrolyl, pyrazinyl, pyridinyl, pyrimidinyl, and furanyl,
or a 9 or 10-membered bicyclic heteroaryl ring selected from the group consisting of indolyl, thieno[2,3-c]pyridinyl, thieno[3,2-c]pyridinyl, benzoxazolyl, and benzisoxazolyl,
each of which is optionally substituted by halo, C$_{1-6}$-alkyl, C$_{1-6}$-alkoxy, C$_{1-6}$-haloalkyl, nitro, hydroxyl, or C$_{1-6}$-haloalkoxy, or by an oxo or dioxo bridge;
R$^5$ is H, OH, or CN;
B is halo, C$_{1-6}$-alkyl optionally substituted by CN, halo or C$_{1-6}$-alkoxy, or C$_{1-6}$-alkoxy;
R$^i$ and R$^{ii}$ are each independently H, C$_{1-6}$-alkyl, C$_{1-6}$-alkyl-NR$^{iii}$R$^{iv}$, —C(O)—C$_{1-6}$-alkyl or —S(O)$_2$—C$_{1-6}$-alkyl;
R$^{iii}$ and R$^{iv}$ are each independently H or C$_{1-6}$-alkyl;
m is 1 to 6; and
n is 0 to 4;
wherein;
5 or 6 membered heteroaryl is selected from the group consisting of oxazolyl, thiazolyl, pyrazinyl, pyrrolyl, pyridinyl, pyrimidinyl, and furanyl; and
an oxo or dioxo bridge is selected from the group consisting of

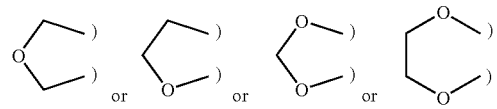

or a pharmaceutically acceptable salt thereof.
2. The compound of claim 1, wherein:
R$^1$ is —(CH$_2$)$_m$—R$^a$ wherein R$^a$ is:
NR$^i$R$^{ii}$, or
aryl, or 5 or 6 membered heteroaryl each of which is optionally substituted by one or more halo, C$_{1-6}$-alkyl, or C$_{1-6}$-alkoxy,
or —(CH$_2$)$_n$—(CO)—R$^b$ or —(CH$_2$)$_n$—(SO$_2$)—R$^b$, wherein R$^b$ is:
C$_{1-6}$-alkyl,
C$_{1-6}$-alkoxy,
NR$^i$R$^{ii}$, or 5 to 6 membered-heterocycloalkyl, or 5 or 6 membered heteroaryl each of which is optionally substituted by one or more halo, $C_{1-6}$-alkyl, or $C_{1-6}$-alkoxy, or $R^1$ and $R^3$ together with the indole ring to which they are attached form a piperazinyl, which is optionally substituted by $C(O)O-C_{1-6}$-alkyl or $C_{1-6}$-alkyl;

there is one or more $R^2$, wherein each $R^2$ is the same or different, $R^2$ is one or more H, halo or $C_{1-6}$-alkyl;

$R^3$ is H or $C_{1-6}$-alkyl;

$R^4$ is —NH(CO)$R^e$, wherein $R^e$ is $C_{1-6}$-alkoxy or aryl which is optionally substituted by halo, or aryl selected from the group consisting of phenyl, naphthyl, phenanthryl, fluorenyl, indenyl, pentalenyl, azulenyl, biphenyl, aminodiphenyl, diphenylsulfidyl, diphenylsulfonyl, and diphenylisopropylidenyl, or a 9 or 10-membered bicyclic heteroaryl ring selected from the group consisting of indolyl, thieno[2,3-c]pyridinyl, thieno[3,2-c]pyridinyl, benzoxazolyl, and benzisoxazolyl, each of which is optionally substituted by halo, $C_{1-6}$-alkyl, $C_{1-6}$-alkoxy, $C_{1-6}$-haloalkyl, nitro, hydroxyl, or $C_{1-6}$-haloalkoxy or by an oxo or dioxo bridge;

$R^5$ is H, OH or CN;

$R^i$ and $R^{ii}$ are each independently H, $C_{1-6}$-alkyl, or $C_{1-6}$-alkyl-$NR^{iii}R^{iv}$;

$R^{iii}$ and $R^{iv}$ are each independently H or $C_{1-6}$-alkyl;

m is 1 to 6; and n is 0 to 4;

wherein an oxo or dioxo bridge is selected from the group consisting of

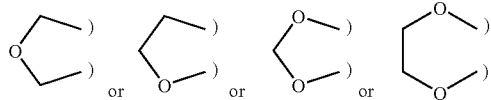

or a pharmaceutically acceptable salt thereof.

3. The compound of claim 1, which is selected from the group consisting of:
   (1-Benzyl-2-methyl-1H-indol-3-yl)-(4-phenyl-piperidin-1-yl)-methanone;
   2-{6-Chloro-3-[4-(2,6-dimethoxy-phenyl)-piperidine-1-carbonyl]-indol-1-yl}-N,N-dimethyl-acetamide;
   2-{6-Chloro-3-[4-(2,6-dimethoxy-phenyl)-piperidine-1-carbonyl]-indol-1-yl}-1-pyridin-2-yl-ethanone;
   (6-Chloro-1-pyridin-4-ylmethyl-1H-indol-3-yl)-[4-(2,6-dimethoxy-phenyl)-piperidin-1-yl]-methanone;
   (6-Chloro-1-pyridin-3-ylmethyl-1H-indol-3-yl)-[4-(2,6-dimethoxy-phenyl)-piperidin-1-yl]-methanone;
   (6-Chloro-1-pyridin-2-ylmethyl-1H-indol-3-yl)-[4-(2,6-dimethoxy-phenyl)-piperidin-1-yl]-methanone;
   [6-Chloro-1-(6-chloro-pyridin-3-ylmethyl)-1H-indol-3-yl]-[4-(2,6-dimethoxy-phenyl)-piperidin-1-yl]-methanone;
   {6-Chloro-3-[4-(2,6-dimethoxy-phenyl)-piperidine-1-carbonyl]-indol-1-yl}-acetic acid tert-butyl ester;
   (6-Chloro-1-pyrazin-2-ylmethyl-1H-indol-3-yl)-[4-(2,6-dimethoxy-phenyl)-piperidin-1-yl]-methanone;
   [6-Chloro-1-(3,5-difluoro-benzyl)-1H-indol-3-yl]-[4-(2,6-dimethoxy-phenyl)-piperidin-1-yl]-methanone; and
   [6-Chloro-1-(2-dimethylamino-ethyl)-1H-indol-3-yl]-[4-(2,6-dimethoxy-phenyl)-piperidin-1-yl]-methanone.

4. The compound of claim 1, which is selected from the group consisting of:
   2-{6-Chloro-3-[4-(2,6-dimethoxy-phenyl)-piperidine-1-carbonyl]-indol-1-yl}-1-(4-methyl-piperazin-1-yl)-ethanone;
   [6-Chloro-1-(3,5-difluoro-benzyl)-1H-indol-3-yl]-[4-(2-methoxy-phenyl)-piperidin-1-yl]-methanone;
   2-{6-Chloro-3-[4-(2-methoxy-phenyl)-piperidine-1-carbonyl]-indol-1-yl}-N,N-dimethyl-acetamide;
   2-{6-Chloro-3-[4-(2-methoxy-phenyl)-piperidine-1-carbonyl]-indol-1-yl}-1-(4-methyl-piperazin-1-yl)-ethanone;
   {6-Chloro-3-[4-(2-methoxy-phenyl)-piperidine-1-carbonyl]-indol-1-yl}-acetic acid tert-butyl ester;
   2-{6-Chloro-3-[4-cyano-4-(2-methoxy-phenyl)-piperidine-1-carbonyl]-indol-1-yl}-N,N-dimethyl-acetamide;
   2-{6-Chloro-3-[4-cyano-4-(2-fluoro-phenyl)-piperidine-1-carbonyl]-indol-1-yl}-N,N-dimethyl-acetamide;
   2-{3-[4-(2,6-Dimethoxy-phenyl)-piperidine-1-carbonyl]-indol-1-yl}-N,N-dimethyl-acetamide;
   [6-Chloro-1-(2-methyl-pyridin-4-ylmethyl)-1H-indol-3-yl]-[4-(2,6-dimethoxy-phenyl)-piperidin-1-yl]-methanone;
   2-{6-Chloro-3-[4-(2-isopropoxy-phenyl)-piperidine-1-carbonyl]-indol-1-yl}-N,N-dimethyl-acetamide;
   2-{6-Chloro-3-[4-(2-isopropoxy-phenyl)-piperidine-1-carbonyl]-indol-1-yl}-1-(4-methyl-piperazin-1-yl)-ethanone; and
   2-{6-Chloro-3-[4-(2,6-dimethoxy-phenyl)-piperidine-1-carbonyl]-indol-1-yl}-1-piperazin-1-yl-ethanone.

5. The compound of claim 1, which is selected from the group consisting of:
   2-{6-Chloro-3-[4-(2,3-dihydro-benzofuran-7-yl)-piperidine-1-carbonyl]-indol-1-yl}-1-(4-methyl-piperazin-1-yl)-ethanone;
   2-{6-Chloro-3-[4-(2,3-dihydro-benzofuran-7-yl)-piperidine-1-carbonyl]-indol-1-yl}-N,N-dimethyl-acetamide;
   2-{6-Chloro-3-[4-(2,3-dihydro-benzofuran-7-yl)-piperidine-1-carbonyl]-indol-1-yl}-N-methyl-acetamide;
   2-{5,6-Dichloro-3-[4-(2-methoxy-phenyl)-piperidine-1-carbonyl]-indol-1-yl}-N,N-dimethyl-acetamide;
   2-{6-Chloro-3-[4-(2,6-dimethoxy-phenyl)-piperidine-1-carbonyl]-indol-1-yl}-acetamide;
   2-{6-Chloro-3-[4-(2,6-dimethoxy-phenyl)-piperidine-1-carbonyl]-indol-1-yl}-N-methyl-acetamide;
   N-(2-Amino-ethyl)-2-{6-chloro-3-[4-(2,6-dimethoxy-phenyl)-piperidine-1-carbonyl]-indol-1-yl}-acetamide;
   [6-Chloro-1-(2-dimethylamino-ethyl)-1H-indol-3-yl]-[4-(2,3-dihydro-benzofuran-7-yl)-piperidin-1-yl]-methanone;
   2-{6-Chloro-3-[4-(2-trifluoromethoxy-phenyl)-piperidine-1-carbonyl]-indol-1-yl}-1-(4-methyl-piperazin-1-yl)-ethanone;
   2-{6-Chloro-3-[4-(2-trifluoromethoxy-phenyl)-piperidine-1-carbonyl]-indol-1-yl}-N-methyl-acetamide;
   2-{6-Chloro-3-[4-(2-trifluoromethoxy-phenyl)-piperidine-1-carbonyl]-indol-1-yl}-N,N-dimethyl-acetamide; and
   2-{6-Chloro-3-[4-(2-trifluoromethyl-phenyl)-piperidine-1-carbonyl]-indol-1-yl}-N-methyl-acetamide.

6. The compound of claim 1, which is selected from the group consisting of:
   2-{6-Chloro-3-[4-(2-trifluoromethyl-phenyl)-piperidine-1-carbonyl]-indol-1-yl}-1-(4-methyl-piperazin-1-yl)-ethanone;

2-{6-Chloro-3-[4-(2-trifluoromethyl-phenyl)-piperidine-1-carbonyl]-indol-1-yl}-N,N-dimethyl-acetamide;
2-{6-Chloro-3-[4-(2-methoxy-phenyl)-piperidine-1-carbonyl]-indol-1-yl}-N-methyl-acetamide;
[6-Chloro-1-(2-methylamino-ethyl)-1H-indol-3-yl]-[4-(2,3-dihydro-benzofuran-7-yl)-piperidin-1-yl]-methanone;
[6-Chloro-1-(2-dimethylamino-ethyl)-1H-indol-3-yl]-[4-(2-methoxy-phenyl)-piperidin-1-yl]-methanone;
2-{6-Chloro-3-[4-(2-fluoro-phenyl)-piperidine-1-carbonyl]-indol-1-yl}-N-methyl-acetamide;
2-{6-Chloro-3-[4-(2-fluoro-phenyl)-piperidine-1-carbonyl]-indol-1-yl}-N,N-dimethyl-acetamide;
[6-Chloro-1-(2-dimethylamino-ethyl)-1H-indol-3-yl]-[4-(2-fluoro-phenyl)-piperidin-1-yl]-methanone;
2-{6-Chloro-3-[4-(2-fluoro-phenyl)-piperidine-1-carbonyl]-indol-1-yl}-1-(4-methyl-piperazin-1-yl)-ethanone; and
2-{6-Chloro-3-[4-(2-fluoro-phenyl)-piperidine-1-carbonyl]-indol-1-yl}-1-piperazin-1-yl-ethanone or hydrochloride salt thereof.

7. A compound of claim 1, which is
2-[6-Chloro-3-(3,4,5,6-tetrahydro-2H-[4,4']bipyridinyl-1-carbonyl)-indol-1-yl]-N,N-dimethyl-acetamide.

8. A pharmaceutical composition comprising a therapeutically effective amount of a compound of formula I

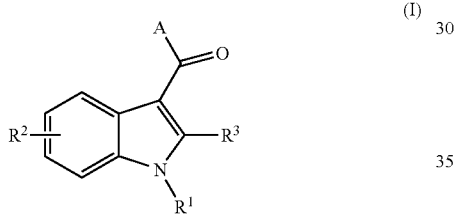

(I)

wherein
$R^1$ is $C_{1-6}$-alkyl substituted by CN, $C_{1-6}$-alkoxy, OH, halo, or $NR^iR^{ii}$,
$C_{2-6}$-alkyl,
aryl, 5 or 6 membered heteroaryl or sulfonylaryl each of which is optionally substituted by one or more B,
—$(CH_2)_m$—$R^a$ wherein $R^a$ is:
CN,
$OR^i$,
$NR^iR^{ii}$, or
$C_{3-6}$-cycloalkyl, 4 to 7 membered-heterocycloalkyl, aryl, or 5 or 6 membered heteroaryl each of which is optionally substituted by one or more B,
or —$(CH_2)_n$—(CO)—$R^b$ or —$(CH_2)_n$—$(SO_2)$—$R^b$, wherein $R^b$ is:
$C_{1-6}$-alkyl,
$C_{1-6}$-alkoxy,
$C_{3-6}$-cycloalkyl,
—$(CH_2)_m$—$NR^{iii}R^{iv}$,
$NR^iR^{ii}$, or
$C_{3-6}$-cycloalkyl, 4 to 7 membered-heterocycloalkyl, aryl, or 5 or 6 membered heteroaryl each of which is optionally substituted by one or more B,
or $R^1$ and $R^3$ together with the indole ring to which they are attached form a piperazinyl, which is optionally substituted by =O, C(O)O—$C_{1-6}$-alkyl or $C_{1-6}$-alkyl;
there is one or more $R^2$, wherein each $R^2$ is the same or different, $R^2$ is one or more H, OH, halo, CN, nitro, $C_{1-6}$-alkoxy, —O—$CH_2$—$C_{2-6}$-alkenyl, benzyloxy, $C_{1-6}$-haloalkoxy, or $C_{1-6}$-alkyl optionally substituted by —$NR^{iii}R^{iv}$ or halo,
or two $R^2$ together with the indole ring to which they are attached form an oxo or dioxo bridge;
$R^3$ is H,
F,
—(CO)—$R^c$, wherein $R^c$ is:
$C_{1-6}$-alkyl,
—$(CH_2)_n$—$NR^iR^{ii}$,
—$(CH_2)_n$—$NR^{iii}R^{iv}$, or
5 or 6 membered heterocycloalkyl optionally substituted by $C_{1-6}$-alkyl,
or $C_{1-6}$-alkyl which is optionally substituted by
halo,
$NR^iR^{ii}$,
$NR^{iii}R^{iv}$,
—O(CO)—$C_{1-6}$-alkyl,
or —NH(CO)$R^d$, wherein $R^d$ is $C_{1-6}$-alkyl optionally substituted by halo or nitro, or $R^d$ is aryl or a 5 or 6 membered heteroaryl, each of which is optionally substituted by halo, nitro, $C_{1-6}$-alkyl or $C_{1-6}$-haloalkyl;
A is

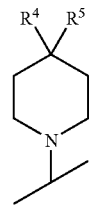

(b)

wherein
$R^4$ is aryl selected from the group consisting of phenyl, naphthyl, phenanthryl, fluorenyl, indenyl, pentalenyl, azulenyl, biphenyl, aminodiphenyl, diphenylsulfidyl, diphenylsulfonyl, and diphenylisopropylidenyl,
5 or 6 membered heteroaryl selected from the group consisting of imidazolyl, oxazolyl, thiazolyl, pyrazinyl, pyrrolyl, pyrazinyl, pyridinyl, pyrimidinyl, and furanyl,
or a 9 or 10-membered bicyclic heteroaryl ring selected from the group consisting of indolyl, thieno[2,3-c]pyridinyl, thieno[3,2-c]pyridinyl, benzoxazolyl, and benzisoxazolyl,
each of which is optionally substituted by CN, halo, $C_{1-6}$-alkyl, $C_{1-6}$-alkoxy, $C_{1-6}$-haloalkyl, nitro, hydroxyl, $NR^iR^{ii}$, $NR^{iii}R^{iv}$, $C_{1-6}$-alkoxy-$C_{1-6}$-alkylene, $S(O)_2$—$C_{1-6}$-alkyl, or $C_{1-6}$-haloalkoxy, or by an oxo or dioxo bridge;
$R^5$ is H, OH, CN, $COOR^{iii}$ or $CONR^{iii}R^{iv}$;
B is halo,
CN,
$NR^iR^{ii}$,
$C_{1-6}$-alkyl optionally substituted by CN, halo or $C_{1-6}$-alkoxy,
$C_{1-6}$-haloalkyl,
$C_{1-6}$-alkoxy,
$C_{1-6}$-haloalkoxy,
$C_{3-6}$-cycloalkyl,
—C(O)O—$C_{1-6}$-alkyl,
—C(O)$NR^iR^{ii}$, —C(O)—$C_{1-6}$-alkyl,
—S(O)$_2$—$C_{1-6}$-alkyl,
—S(O)$_2$—NR$^i$R$^{ii}$, or
(CR$^{iii}$R$^{iv}$)$_n$-phenyl, or (CR$^{iii}$R$^{iv}$)$_n$-5 or 6 membered heteroaryl wherein the phenyl or 5 or 6 membered heteroaryl moiety is optionally substituted by one or more substituent(s) selected from the group consisting of:
halo, CN, NR$^i$R$^{ii}$, $C_{1-6}$-alkyl optionally substituted by CN or $C_{1-6}$-alkoxy, $C_{1-6}$-alkoxy, $C_{1-6}$-haloalkoxy, $C_{3-6}$-cycloalkyl, —C(O)O—$C_{1-6}$-alkyl, —C(O)—NR$^i$R$^{ii}$, —C(O)—$C_{1-6}$-alkyl, —S(O)$_2$—$C_{1-6}$-alkyl, and —S(O)$_2$—NR$^i$R$^{ii}$;

R$^i$ and R$^{ii}$ are each independently H, $C_{1-6}$-alkyl, $C_{1-6}$-alkyl-NR$^{iii}$R$^{iv}$, —(CO)O—$C_{1-6}$-alkyl, —C(O)—NR$^{iii}$R$^{iv}$, —C(O)—$C_{1-6}$-alkyl, —S(O)$_2$—$C_{1-6}$-alkyl or —S(O)$_2$—NR$^{iii}$R$^{iv}$;

R$^{iii}$ and R$^{iv}$ are each independently H or $C_{1-6}$-alkyl;
m is 1 to 6; and
n is 0 to 4;

wherein 4 to 7 membered heterocycloalkyl is selected from the group consisting of oxetanyl, tetrahydro-furanyl, piperidinyl, pyrrolidinyl, morpholinyl, and piperazinyl;

5 or 6 membered heteroaryl is selected from the group consisting of oxazolyl, thiazolyl, pyrazinyl, pyrrolyl, pyridinyl, pyrimidinyl, and furanyl; and an oxo or dioxo bridge is selected from the group consisting of

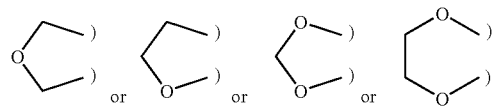

or a pharmaceutically acceptable salt thereof and a pharmaceutically acceptable carrier.

* * * * *